(12) United States Patent
Kline

(10) Patent No.: US 10,657,780 B1
(45) Date of Patent: May 19, 2020

(54) SYSTEM, METHOD, AND APPARATUS FOR MIXING, BLENDING, DISPENSING, MONITORING, AND LABELING PRODUCTS

(71) Applicant: TransparenSee LLC, Marietta, GA (US)

(72) Inventor: Michael J. Kline, Corono Del Mar, CA (US)

(73) Assignee: TRANSPARENSEE LLC, Marietta, GA (US)

( * ) Notice: Subject to any disclaimer, the term of this patent is extended or adjusted under 35 U.S.C. 154(b) by 270 days.

(21) Appl. No.: 15/691,428

(22) Filed: Aug. 30, 2017

Related U.S. Application Data

(63) Continuation of application No. 14/609,247, filed on Jan. 29, 2015, now abandoned.

(51) Int. Cl.
| | |
|---|---|
| *G08B 7/06* | (2006.01) |
| *G08B 3/10* | (2006.01) |
| *B65D 25/56* | (2006.01) |
| *G08B 5/22* | (2006.01) |

(52) U.S. Cl.
CPC .............. *G08B 7/06* (2013.01); *B65D 25/56* (2013.01); *G08B 3/10* (2013.01); *G08B 5/22* (2013.01)

(58) Field of Classification Search
CPC ..................................................... B65D 25/56
USPC ........................................................ 700/231
See application file for complete search history.

(56) References Cited

U.S. PATENT DOCUMENTS

| | | | |
|---|---|---|---|
| 4,512,431 A | 4/1985 | Bloomfield | |
| 4,534,818 A | 8/1985 | Kreager et al. | |
| 6,161,059 A | 12/2000 | Tedesco et al. | |
| 6,413,000 B1 | 7/2002 | Borcherds et al. | |
| 6,751,525 B1 | 6/2004 | Crisp, III | |
| 7,493,267 B1 | 2/2009 | Walker et al. | |
| 7,627,496 B2 | 12/2009 | Walker et al. | |
| 7,757,896 B2 | 7/2010 | Carpenter et al. | |
| 8,340,815 B2 | 12/2012 | Peters et al. | |
| 8,364,520 B1 | 1/2013 | Eichorn et al. | |
| 8,392,019 B2 | 3/2013 | Segal et al. | |
| 8,489,450 B2 | 7/2013 | Agarwal | |
| 8,601,938 B2 | 12/2013 | Huber et al. | |
| 8,616,250 B2 | 12/2013 | Herbert | |

(Continued)

FOREIGN PATENT DOCUMENTS

| | | |
|---|---|---|
| CA | 2912016 A1 | 11/2014 |
| JP | 09050426 A  * | 2/1997 |

(Continued)

OTHER PUBLICATIONS

International Patent Application No. PCT/US2015/040939: International Search Report and Written Opinion dated Dec. 31, 2015, 13 pages.

(Continued)

*Primary Examiner* — Emilio J Saavedra

(74) *Attorney, Agent, or Firm* — BakerHostetler

(57) ABSTRACT

Systems, methods, and apparatus are disclosed that enable certain establishments that serve self-serve food and/or serve food via vending machines, to comply with recently issued FDA rules for providing calorie content and Nutrition Facts information to consumers. The calorie content and/or Nutrition Facts may be displayed on an electronic display, printed on a label, and/or provided via an audible signal, and/or may be provided in real time.

18 Claims, 18 Drawing Sheets

(56) References Cited

U.S. PATENT DOCUMENTS

| | | |
|---|---|---|
| 8,656,690 B2 | 2/2014 | Bierschenk et al. |
| 8,744,618 B2 | 6/2014 | Peters et al. |
| 8,755,932 B2 | 6/2014 | Peters et al. |
| 8,787,006 B2 | 7/2014 | Golko et al. |
| 8,788,341 B1 | 7/2014 | Patel et al. |
| 9,155,330 B1 | 10/2015 | Shtivelman |
| 9,527,716 B2 | 12/2016 | Kline et al. |
| 9,633,504 B2 | 4/2017 | Kline et al. |
| 9,701,530 B2 | 7/2017 | Kline et al. |
| 10,121,132 B2 | 11/2018 | Salvucci et al. |
| 10,319,001 B2 | 6/2019 | Kline et al. |
| 2002/0173875 A1 | 11/2002 | Wallace et al. |
| 2003/0055727 A1 | 3/2003 | Walker et al. |
| 2003/0208409 A1 | 11/2003 | Mault |
| 2004/0049427 A1 | 3/2004 | Tami et al. |
| 2004/0065700 A1 | 4/2004 | Milian |
| 2004/0118733 A1 | 6/2004 | Pauli |
| 2004/0137078 A1 | 7/2004 | Najafi et al. |
| 2004/0241759 A1 | 12/2004 | Tozer et al. |
| 2004/0249711 A1 | 12/2004 | Walker et al. |
| 2005/0048461 A1 | 3/2005 | Lahteenmaki |
| 2005/0193896 A1 | 9/2005 | McGill |
| 2005/0210834 A1 | 9/2005 | Kamineni |
| 2005/0226970 A1* | 10/2005 | Gordon ............... B65D 5/4212 426/231 |
| 2005/0273387 A1 | 12/2005 | Previdi |
| 2006/0027597 A1 | 2/2006 | Chow et al. |
| 2006/0081653 A1* | 4/2006 | Boland .................. A47J 31/40 222/243 |
| 2006/0247824 A1 | 11/2006 | Walker et al. |
| 2006/0278093 A1 | 12/2006 | Biderman et al. |
| 2007/0027576 A1 | 2/2007 | Juds et al. |
| 2007/0050083 A1 | 3/2007 | Signorelli et al. |
| 2007/0078561 A1 | 4/2007 | Sansone |
| 2007/0100649 A1 | 5/2007 | Walker et al. |
| 2007/0110880 A1 | 5/2007 | Thomas et al. |
| 2007/0156523 A1 | 7/2007 | Liu et al. |
| 2007/0255450 A1 | 11/2007 | Mazur et al. |
| 2008/0077455 A1 | 3/2008 | Gilboa |
| 2009/0065520 A1 | 3/2009 | Peters et al. |
| 2009/0065570 A1 | 3/2009 | Peters et al. |
| 2009/0069931 A1 | 3/2009 | Peters et al. |
| 2009/0070234 A1 | 3/2009 | Peters et al. |
| 2009/0138817 A1 | 5/2009 | Oron et al. |
| 2009/0176526 A1* | 7/2009 | Altman ............... G06F 19/3475 455/556.1 |
| 2009/0177318 A1 | 7/2009 | Sizemore |
| 2009/0222300 A1 | 9/2009 | Guith et al. |
| 2009/0222301 A1 | 9/2009 | Phillips et al. |
| 2009/0222339 A1 | 9/2009 | Antao et al. |
| 2009/0222340 A1 | 9/2009 | Insolia et al. |
| 2010/0131096 A1 | 5/2010 | Koyano |
| 2010/0169313 A1 | 7/2010 | Kenedy et al. |
| 2010/0200110 A1 | 8/2010 | Segiet et al. |
| 2010/0280895 A1 | 11/2010 | Mottola |
| 2010/0286819 A1 | 11/2010 | Walker et al. |
| 2011/0038474 A1 | 2/2011 | Omiya |
| 2011/0049180 A1 | 3/2011 | Carpenter et al. |
| 2011/0121032 A1 | 5/2011 | Deo et al. |
| 2011/0168290 A1 | 7/2011 | Breitenbach et al. |
| 2011/0282723 A1 | 11/2011 | Phillips et al. |
| 2012/0053426 A1 | 3/2012 | Webster et al. |
| 2012/0055718 A1* | 3/2012 | Chen .................. G06F 19/3475 177/3 |
| 2012/0150613 A1 | 6/2012 | Insolia et al. |
| 2012/0190386 A1 | 7/2012 | Anderson |
| 2012/0325844 A1 | 12/2012 | Quartarone et al. |
| 2012/0325845 A1 | 12/2012 | Newman et al. |
| 2013/0002724 A1 | 1/2013 | Heinrich et al. |
| 2013/0025529 A1 | 1/2013 | Key |
| 2013/0027060 A1 | 1/2013 | Tralshawala et al. |
| 2013/0035787 A1 | 2/2013 | Canter |
| 2013/0037565 A1 | 2/2013 | Newman |
| 2013/0044042 A1 | 2/2013 | Olsson et al. |
| 2013/0079117 A1 | 3/2013 | Maskatia et al. |
| 2013/0079926 A1 | 3/2013 | Peters et al. |
| 2013/0096715 A1 | 4/2013 | Chung et al. |
| 2013/0103187 A1 | 4/2013 | Canter et al. |
| 2013/0220480 A1 | 8/2013 | Angus et al. |
| 2013/0226338 A1 | 8/2013 | Pickett et al. |
| 2013/0240559 A1 | 9/2013 | Rudick |
| 2013/0245819 A1 | 9/2013 | Davenport et al. |
| 2013/0248560 A1 | 9/2013 | Carpenter et al. |
| 2013/0282169 A1 | 10/2013 | Moore et al. |
| 2013/0282451 A1 | 10/2013 | Moore et al. |
| 2013/0304265 A1 | 11/2013 | Deo et al. |
| 2014/0027502 A1 | 1/2014 | Schwartz |
| 2014/0040055 A1 | 2/2014 | Quartarone et al. |
| 2014/0130891 A1 | 5/2014 | Abdelmoteleb et al. |
| 2014/0135967 A1 | 5/2014 | Bippert |
| 2014/0212566 A1 | 7/2014 | Herbert et al. |
| 2014/0246452 A1 | 9/2014 | Roekens et al. |
| 2014/0255883 A1 | 9/2014 | Macquet |
| 2014/0257749 A1 | 9/2014 | Nathanson |
| 2014/0286123 A1 | 9/2014 | Arnett et al. |
| 2014/0307756 A1 | 10/2014 | Chen et al. |
| 2014/0356492 A1 | 12/2014 | Merea |
| 2015/0100152 A1 | 4/2015 | Barragán Treviño et al. |
| 2015/0105901 A1 | 4/2015 | Joshi et al. |
| 2015/0144650 A1 | 5/2015 | Kline et al. |
| 2015/0144652 A1 | 5/2015 | Kline et al. |
| 2015/0144653 A1 | 5/2015 | Kline et al. |
| 2015/0239724 A1 | 8/2015 | Cronise |
| 2015/0290795 A1 | 10/2015 | Oleynik |
| 2015/0305564 A1* | 10/2015 | Jimenez ............... A47J 43/046 366/141 |
| 2016/0005329 A1 | 1/2016 | Sako et al. |
| 2016/0012749 A1 | 1/2016 | Connor |
| 2016/0148536 A1 | 5/2016 | Ashby |
| 2016/0220973 A1* | 8/2016 | Kolar ............... B01F 15/00201 |
| 2016/0260351 A1 | 9/2016 | Okuma et al. |
| 2016/0379520 A1 | 12/2016 | Borel et al. |

FOREIGN PATENT DOCUMENTS

| | | | |
|---|---|---|---|
| TW | 200505381 A | * | 9/2005 |
| WO | WO9845766 A1 | | 10/1998 |
| WO | WO2013077895 A1 | | 5/2013 |

OTHER PUBLICATIONS

Caprio, "Calories from Soft Drinks—Do They Matter?", The New England Journal of Medicine, Sep. 27, 2012, pp. 1-2.

Dietz, "Wireless Liquid Level Sensing for Restaurant Applications", MERL—A Mitsubishi Electric Research Laboratory, Apr. 2002, pp. 1-8.

"Food labeling: Nutrition Labeling of Standard Menu Items in Restaurants and Similar Retail Food Establishments", Federal Register, Dec. 1, 2014, pp. 1-105.

"Food Labeling: Calorie Labeling of Articles of Food in Vending Machines", Federal Register, Dec. 1, 2014, pp. 1-35.

Northrup, "The Juicero Was a Terrible Idea That Became a Money-Losing Business", Consumerist, Sep. 8, 2017, 8 Pages.

U.S. Appl. No. 14/609,247: Non Final Rejection dated Mar. 10, 2017, 14 pages.

U.S. Appl. No. 14/609,247: Final Rejection dated Jun. 30, 2017, 19 pages.

U.S. Appl. No. 14/609,241: Non Final Rejection dated Apr. 21, 2017, 12 pages.

* cited by examiner

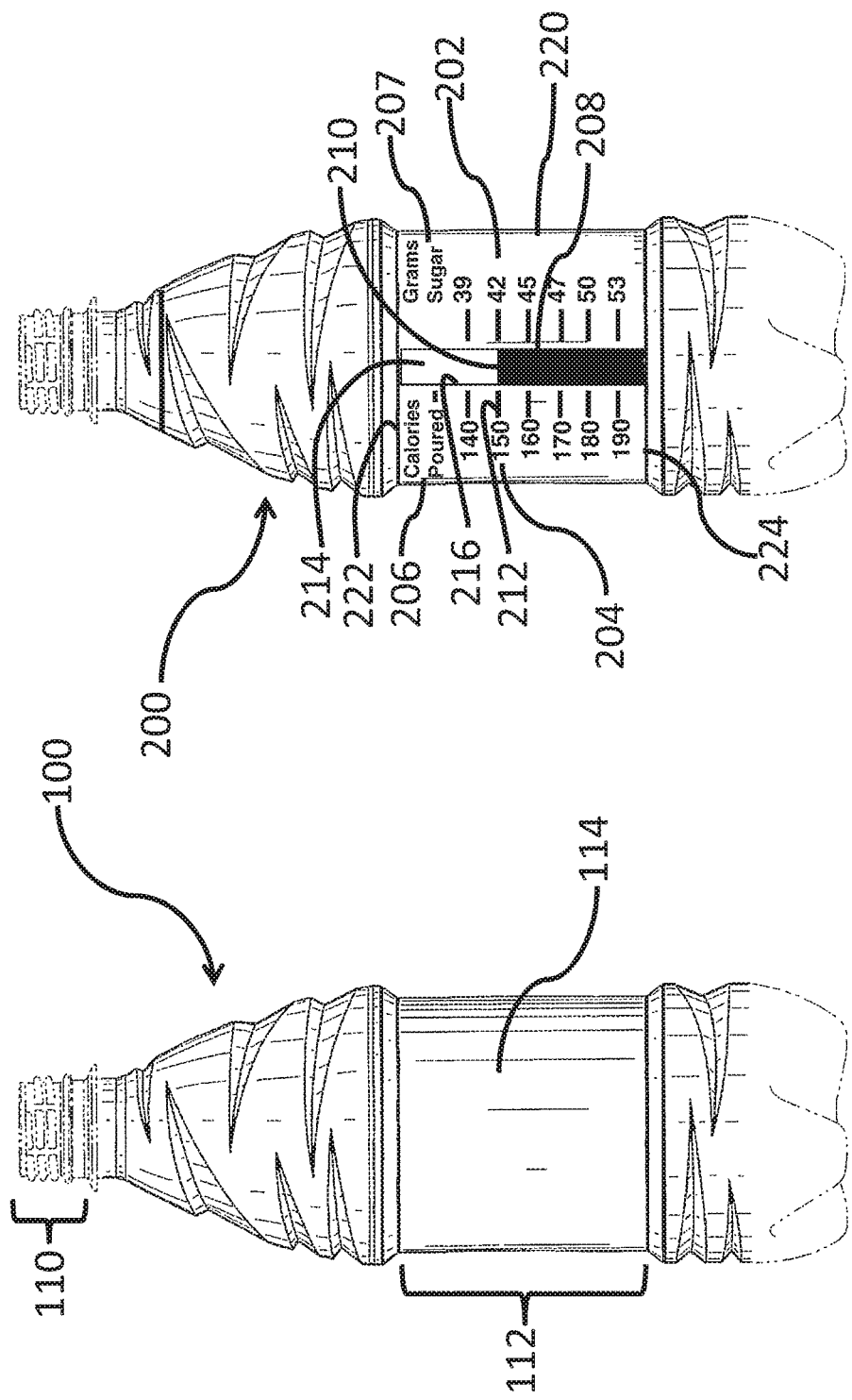

SYSTEM, METHOD, AND APPARATUS FOR MIXING, BLENDING, DISPENSING, MONITORING, AND LABELING PRODUCTS

CROSS-REFERENCE TO RELATED APPLICATIONS

This application is a continuation of U.S. patent application Ser. No. 14/609,247 entitled SYSTEM, METHOD, AND APPARATUS FOR MIXING, BLENDING, DISPENSING, MONITORING, AND LABELING, PRODUCTS, filed Jan. 29, 2015. Application Ser. No. 14/609,247 refers to subject matter disclosed in co-pending U.S. patent application Ser. No. 14/335,855, entitled SYSTEM, METHOD, AND APPARATUS FOR PURCHASING, DISPENSING, OR SAMPLING OF PRODUCTS, filed Jul. 18, 2014, which is a continuation-in-part of pending U.S. application Ser. No. 14/269,741, entitled SYSTEM, METHOD, AND APPARATUS FOR PURCHASING, DISPENSING, OR SAMPLING OF PRODUCTS, filed May 5, 2014, which is a continuation-in-part of pending U.S. patent application Ser. No. 14/087,881, entitled SYSTEM, METHOD, AND APPARATUS FOR PURCHASING, DISPENSING, OR SAMPLING OF PRODUCTS filed Nov. 22, 2013, whose contents are expressly incorporated in their entirety by reference herein.

COPYRIGHT NOTICE

This application contains copyrightable subject matter owned by the named applicant. The applicant reserves all rights in such copyrightable subject matter to the full extent provided under the copyright laws of the United States of America and any comparable international laws.

BACKGROUND

It has been said—somewhat obviously—that "all calories count." But this is only part of the story. Unless calories can effectively be counted, they do not effectively count to those who wish to count them.

And a growing number of consumers are trying hard to count their calorie consumption, particularly for sugar-containing foods and beverages, and for good reason. Data from the Centers for Disease Control and Prevention in Atlanta (CDC), published in 2014, shows that more than one-third (34.9% or 78.6 million) of U.S. adults are obese. Obesity now affects 17% of all children and adolescents in the United States—triple the rate from just one generation ago. Obesity-related conditions include heart disease, stroke, type 2 diabetes and certain types of cancer, some of the leading causes of preventable death. The estimated annual medical cost of obesity in the U.S. was $147 billion in 2008 U.S. dollars; the medical costs for people who are obese were $1,429 per year higher than those of normal weight.

And, also per the CDC, obesity affects some groups more than others. Non-Hispanic blacks have the highest age-adjusted rates of obesity (47.8%) followed by Hispanics (42.5%), non-Hispanic whites (32.6%), and non-Hispanic Asians (10.8%). Obesity is higher among middle age adults, 40-59 years old (39.5%) than among younger adults, age 20-39 (30.3%) or adults over 60 or above (35.4%).

As reported by the CDC on Jun. 17, 2011, milk and 100% fruit juice are a source of water and provide key nutrients such as calcium and vitamin C. Other beverages, referred to as sugar drinks or sugar-sweetened beverages (SSBs), also are a source of water but have poor nutritional value. SSBs are the largest source of added sugars in the diet of U.S. youths, and the increased caloric intake resulting from these beverages is one factor contributing to the prevalence of obesity among adolescents in the United States. In the same report, the CDC noted that daily consumption of regular soda or pop, sports drinks, and other SSBs also is common in the high school student population, and that consumption of these beverages might be related to negative health outcomes. A recent meta-analysis found soft drink intake to be associated with increased energy intake and body weight, and with lower intakes of milk, calcium, and other nutrients. Among adolescents specifically, SSB consumption can contribute to weight gain, type 2 diabetes, and metabolic syndrome.

Barry Popkin, a nutrition professor at the University of North Carolina-Chapel Hill, purportedly one of the nation's top experts on beverage consumption, claims that the biggest single contributor to child and adult obesity in America is sugar-sweetened beverages. Reportedly, Americans derive about 7% of their calories from sugar-sweetened soda. And while all calories may count, (if counted and countable) the *New England Journal of Medicine* has reported that not all calories count the same. The increase in consumption of sugar-sweetened beverages among both adults and children in the United States and other countries is a potential contributor to the obesity epidemic, and sugar intake from sugar-sweetened beverages alone comprises the largest single caloric food source in the United States. Caprio, Sonia, Md., "Calories from Soft Drinks—Do They Matter?" *N Engl J Med* 2012; 367:1462-1463. Some studies have suggested that the risk of obesity among those with genetic predisposition for obesity rises in proportion to how many sugary drinks the person consumes. Other studies suggest that high-fructose corn syrup, used to sweeten soft drinks, may increase body fat to a greater degree than sugar as it is found in nature. As Dr. Sanjay Gupta reported on CNN: "[T]he scientific community has . . . reached a consensus that soft drinks are the one food or beverage that's been demonstrated to cause weight gain and obesity. And if we're going to deal with this obesity epidemic, that's the place to start."

Despite such evidence, the FDA does not currently require that food and beverage cups filled and served, for example, at fast food restaurants, food courts, sporting events, and other locations often frequented by children and adolescents, as well as those demographic populations most prone to obesity, display either on the food or beverage dispensing machines or the containers into which the food or beverage products are dispensed, a calorie count, a sugar count, or any other attribute of the food or beverage, as is required for identical foods and beverages sold in prepackaged containers, which are required by the FDA to clearly display Nutrition Facts labels providing such information. It is somewhat ironic that the FDA requires a Nutrition Facts label to be displayed on a 7.5 ounce mini can of Coca-Cola, but not on a 48-ounce "Big Gulp" poured from a fountain dispenser, containing the identical beverage, with six times the amount of calories and sugar.

Even leaders in the soft drink industry have come to the realization that they need to do more to combat the obesity crisis. Companies that purchase and sell such products to consumers have also taken notice, and have publicly committed to take steps to fight the obesity epidemic. Those that are sincere in such promises, for example, Chik-Fil-A, post calorie count menus at the point of sale, and offer menus containing calorie counts for free to consumers. But such efforts, as well meaning as they may be, are not entirely effective. In some cases, the menus only display the calorie count, not the sugar count, or only display the calorie count for a small serving size, not all serving sizes. And such efforts do nothing to address the trend of consumers to customize their food and beverage choices, for example, by mixing different soft drinks to create a customized blend, or to take into account calorie or sugar count variability from one serving to the next, due to differences in serving size, fill height, or the presence or absence of ice in a beverage container.

Methods, systems, and apparatus designed to address some of these issues are disclosed in co-pending U.S. patent application Ser. No. 14/335,855, filed Jul. 18, 2014 and incorporated in its entirety by reference herein. That application discloses, inter alia, displaying in real time a virtual Nutrition Facts label for food and beverage products as they are being dispensed and/or at the conclusion of a dispensing operation and/or dispensing a label disclosing such Nutrition Facts at the conclusion of the dispensing operation. The label may be configured with an adhesive or otherwise may be capable of being attached to or printed directly on a container for the food or beverage product.

Occasionally, however, a consumer may not wish to consume the entire portion of a food or beverage product contained in a bottle, can, cup, aseptic package, or other container. In such cases, the consumer may be left to guess or estimate how much of a food or beverage product has been consumed, how many calories have been consumed, how much sugar has been consumed, and how much of each remains in the container. While such estimation may be possible in a clear container with straight walls, such that, for example, the consumer might approximate when half the product has been consumed, such estimation is far more difficult for opaque containers, such as drink boxes, or containers without straight side walls, such as a Coca-Cola® contour bottle, or opaque cups with ice and outwardly flaring side walls, or for containers into which ice has been dispensed.

Containers with printed indicia thereon and containers having labels with indicia thereon to indicate the quantity of product contained within the container are well known. For example, U.S. Patent Application Publication No. US 2011/0049180 A1, published Mar. 3, 2011 and incorporated in its entirety by reference herein, teaches printing a plurality of machine readable and other indicia on a vessel intended to receive a beverage. U.S. Patent Application Publication No. US 2013/0025529 A1, published Jan. 31, 2013, discloses a label with a viewing window including measurement information displayed on the label to enable doses of products such as medicine to be measured. U.S. Patent Application Publication No. US 2014/0027502 A1, published Jan. 30, 2014, discloses a polystyrene cup with measurement markings formed therein or printed thereon, such as may be used by a consumer of coffee to determine how much milk or cream to add to the coffee.

But there remains a need in the art to more readily provide consumers of food and beverage products, whether prepackaged or dispensed, to determine the quantity of calories, and other ingredient attributes of the food or beverage product contained in, dispensed into, and/or consumed from the container in which such products are held. There is also a need for consumers of carryout food products, whether from a pizza parlor, fast food restaurant, or food/salad bar, to be able to readily determine the Nutrition Facts of the food or beverage product they have purchased.

As consumers become more savvy and educated about the foods and beverages they consume, they also expect more clarity and more information concerning the ingredients, attributes, Nutrition Facts, and the relative food/beverage "quality" from a health and nutrition perspective of the food and beverage products they purchase and consume. For this reason, a number of smart phone apps, including "Lose It!" and "Fooducate" have become popular. These apps allow consumers in a grocery store, for example, to use their smart phone to scan bar codes on a packaged food or beverage product an receive data via the app such as Nutrition Facts, a food or beverage "grade" or "rating," and food or beverage options and alternatives that may have a better "grade" or "rating." But there is currently no method, system, or apparatus known to the inventor hereof that permits a consumer to readily receive, at the point of purchase or consumption, Nutrition Facts and/or a Nutrition Facts label for customized blends of food and/or beverage products, such as may be created at health food and other outlets that prepare, for example, smoothies, shakes, frozen yogurt blends, and other food and beverage products to order and for immediate consumption.

As used herein, the term "food or beverage product for immediate consumption" is intended to mean an immediately consumable food or beverage product, which is a food or beverage product that is packaged or placed in a container, but is not shelf-stable, rather, is prepared with the intent that it be consumed within a short period of time after being prepared, generally about 24 hours or less, and including but not limited to beverages served through distribution channels where consumers buy beverage fountain products, to be consumed mainly away from home.

As used herein, "fountain equipment" means equipment used in retail outlets to dispense beverages into cups or glasses for immediate consumption.

As used herein, "at-home fountain equipment" means equipment primarily used at home, office or otherwise away from a retail outlet to dispense beverages into cups or glasses for immediate consumption or sealed containers for future consumption.

As used herein, "future consumption" means a distribution channel where consumers buy beverage packages comprising multi-packs and larger packages and packaged food products from supermarkets and discounters which are not consumed on the spot.

As used herein, the term "ingredient attribute" of a product, such as a food or beverage product, means an ingredient-specific quantity relating to the product, in the case of a food or beverage product, selected from the group comprising number of calories, and amount, by weight or % daily value, of sugar, added sugar, sugar alcohol, sodium, total fat, saturated fat, trans fat, polyunsaturated fat, monounsaturated fat, cholesterol, potassium, total carbohydrates, fiber, dietary fiber, protein, vitamins, and minerals, and excluding quantity of the food or beverage by weight or volume.

SUMMARY

The present disclosure describes a container comprising a plurality of visual indicators, at least one of the visual indicators intended to correspond to and display a calorie count of a food or beverage product to be contained in the container, at a time when at least a portion of the food or beverage product has been consumed from the container. At least one of the visual indicators may be intended to display a number of calories associated with a consumed and/or remaining quantity of the food or beverage product to be contained in the container. The container may comprise a substantially transparent portion intended to enable viewing of a level of the food or beverage product to be contained in the container and to enable comparison thereof to the at least one of the plurality of visual indicators. The substantially transparent portion may comprise a sidewall of the container. The container may comprise a label, at least a portion of which may comprise a substantially transparent region intended to enable viewing of one or more levels of a food or beverage product when contained in the container. The container may comprise a plastic beverage container comprising a label panel having a top border and bottom border, and the label and the substantially transparent region may extend substantially from the top border to the bottom border. At least one of the plurality of visual indicators may correspond to and display an amount, by weight and/or % daily value, of: sugar, added sugar, sugar alcohol, sodium, total fat, saturated fat, trans fat, polyunsaturated fat, monounsaturated fat, cholesterol, potassium, total carbohydrates, fiber, dietary fiber, protein, vitamins, and/or minerals, of a food or beverage product to be contained in the container, at a time when a level of the food or beverage product to be contained in the container substantially corresponds to a level of the at least another of the plurality of visual indicators. The plurality of visual indicators may be placed directly on the container, molded into the container, painted on the container, and/or printed on the container. The plurality of graduated visual indicators may comprise, at least in part, a thermochromic material. The container may comprise an aseptic package comprising a viewing region intended to permit a level of a food or beverage product intended to be contained in the container to be viewed or approximated. The viewing region may comprise a transparent or translucent material. The viewing region may comprise a thermochromic material. The container may comprise a label displaying an alignment indicator intended to correspond to an initial fill line of a food or beverage product for immediate consumption when contained in the container, the label further displaying one or more product attribute indicators intended to correlate one or more subsequent product fill lines of the food or beverage product for immediate consumption with one or more product attributes corresponding to a quantity of the food or beverage product for immediate consumption remaining in and/or consumed from the container. The product attribute indicators may be intended to correlate the one or more subsequent product fill lines with calories associated with a quantity of the food or beverage product for immediate consumption remaining in and/or consumed from the container. The product attribute indicators may be further intended to correlate the one or more subsequent product fill lines with an amount, by weight and/or % daily value, of one or more of: sugar, added sugar, sugar alcohol, sodium, total fat, saturated fat, trans fat, polyunsaturated fat, monounsaturated fat, cholesterol, potassium, total carbohydrates, fiber, dietary fiber, protein, vitamins, and/or minerals, of the food or beverage product for immediate consumption, associated with a quantity of the food or beverage product for immediate consumption remaining in and/or consumed from the container. The container may comprise a label comprising a viewing portion comprising an open section, a transparent material, or a translucent material intended to permit a level of a food or beverage product for immediate consumption to be viewed through the container when the food or beverage product for immediate consumption is present therein. The container may further comprise a label comprising a Nutrition Facts section intended to communicate Nutrition Facts corresponding to the food or beverage product for immediate consumption. The label may be selected from the group comprising a label with an adhesive backing, a label with a peel and stick backing, and a label printed directly onto the container.

In another aspect, the disclosure describes a system that may comprise a container and a food or beverage product dispenser configured to determine dispensed quantities of an ingredient attribute of a food or beverage product for immediate consumption from the food or beverage product dispenser into the container, the system further configured to provide a graduated label intended for application to the container, the graduated label intended to display, based on the dispensed quantities of the ingredient attribute, an initial quantity of the ingredient attribute following a dispensing operation of the food or beverage product for immediate consumption into the container, and at least one subsequent quantity of the ingredient attribute attributable to future consumption of at least a portion of the food or beverage product for immediate consumption from the container, the system further configured to enable a user, while consuming the food or beverage product for immediate consumption from the container, to determine, based on a level of the food or beverage product for immediate consumption remaining in the container relative to a graduated display on the graduated label, the at least one subsequent quantity of the ingredient attribute. The at least one subsequent quantity of the ingredient attribute may comprise a consumed quantity of the ingredient attribute and/or a remaining quantity of the ingredient attribute. The ingredient attribute may be one or more attributes selected from the group comprising number of calories, and amount, by weight or % daily value, of sugar, added sugar, sugar alcohol, sodium, total fat, saturated fat, trans fat, polyunsaturated fat, monounsaturated fat, cholesterol, potassium, total carbohydrates, fiber, dietary fiber, protein, vitamins, and minerals. The system may further comprise a food or beverage product dispenser configured to determine positions of graduated visual indicators on the container based on one or more of: a bottom level of the container, a rate of fill of the container, a duration of fill of the container, a fill height of the container, and a weight of food or beverage product for immediate consumption dispensed into the container. The food or beverage product dispenser may be configured to determine the positions of graduated visual indicators at intervals during the dispensing operation. The food or beverage product dispenser may be configured to determine the positions of graduated visual indicators to compensate for ice dispensed into the container and/or product foaming of a beverage dispensed into the container. The system may comprise a printer head configured to print the graduated label directly onto the container, the printer head configured to move vertically relative to the container in a first direction, to move horizontally relative to the container in a second direction, and to move in a third direction normal to a surface of the container. The system may comprise a printer configured to print a label intended for application to the container, the label comprising the plurality of graduated visual indicators. The label may comprise Nutrition Facts for the food or beverage product for immediate consumption to be dispensed into and contained in the container.

In another aspect, the disclosure describes a system comprising an input device configured to receive Nutrition Facts information specific to a food or beverage product, a weighing apparatus configured to weigh the food or beverage product, a food or beverage processor configured to blend the food or beverage product to yield a blended food or beverage product for immediate consumption, and a printer or display configured to dispense or display a Nutrition Facts label comprising Nutrition Facts specific to the blended food or beverage product for immediate consumption.

In another aspect, the disclosure describes a method comprising receiving first Nutrition Facts data specific to a first food or beverage product, receiving first weight or volume data for the first food or beverage product, receiving second Nutrition Facts data specific to a second food or beverage product, receiving second weight or volume data for the second food or beverage product, based on the previous operations, determining third Nutrition Facts data for a food or beverage product for immediate consumption comprising a mixture of the first food or beverage product and the second food or beverage product, and printing or displaying the third Nutrition Facts data.

Another aspect of the disclosure describes a blender comprising a housing and a blending container, the blender comprising a reader configured to receive Nutrition Facts information specific to a food or beverage product, the blender further comprising a weighing mechanism configured to determine a net weight of the food or beverage product when placed in the blending container, the blender further configured to determine, based on the Nutrition Facts information specific to the food or beverage product and the net weight of the food or beverage product, Nutrition Facts for a food or beverage product for immediate consumption processed by the blender, the blender further configured to dispense one or more of a Nutrition Facts label and a Nutrition Facts receipt, and/or to display on a display associated with the blender a virtual Nutrition Facts label, for the food or beverage product for immediate consumption processed by the blender.

Another aspect of the disclosure describes a system comprising a plurality of ingredients, at least one of the plurality of ingredients comprising coded indicia coded with information comprising Nutrition Facts and a weight or volume specific to the at least one of the plurality of ingredients; the system further comprising a scanner configured to scan the coded indicia and access the information; the system further comprising a food or beverage dispenser or a food processor or blender configured to combine the plurality of ingredients and provide a resulting food or beverage product for immediate consumption; the system further configured, based on the information, to dispense one or more of a Nutrition Facts label and a Nutrition Facts receipt, and/or to display on a display associated with the food or beverage dispenser or food processor or blender a virtual Nutrition Facts label, for the resulting food or beverage product for immediate consumption.

Another aspect of the disclosure describes a system comprising a wearable device having a wearable device display, and a food or beverage product dispenser configured to dispense a food or beverage product for immediate consumption, the wearable device configured to access Nutrition Facts data for a food or beverage product for immediate consumption selected to be dispensed from the food or beverage product dispenser, to determine a dispensed quantity of the food or beverage product for immediate consumption selected to be dispensed, and to display, based on the Nutrition Facts data and the dispensed quantity, a virtual Nutrition Facts label for the food or beverage product to be dispensed from the food or beverage dispenser.

Another aspect of the disclosure describes a method comprising: accessing Nutrition Facts information, via a wearable device or another portable device such as a smart phone, for a food or beverage product for immediate consumption available from a first food or beverage product dispenser; determining, via the wearable device or other portable device, a dispensing rate for the food or beverage product dispenser; determining, via the wearable device or other portable device, that dispensing of the food or beverage product for immediate consumption from the first food or product dispenser has begun; determining, via the wearable device or portable device, a period of time of dispensing of the food or beverage product for immediate consumption; and displaying, via the wearable device or portable device, and based on the Nutrition Facts information, the dispensing rate, and the period of time, a virtual Nutrition Facts label for the food or beverage product for immediate consumption. The virtual Nutrition Facts label may be specific to the actual quantity of the food or beverage product for immediate consumption that is dispensed.

According to another aspect, the disclosure describes a wearable device comprising a wearable device display, the wearable device configured to interface with a food or beverage product dispenser of a food or beverage product for immediate consumption, the wearable device configured to access or determine volumetric or mass flow rate data for the food or beverage product dispenser, the wearable device further comprising a camera or a sensor with a field of view, the camera or sensor configured to capture within the field of view from the food or beverage product dispenser an image of a brand or icon associated with the food or beverage product for immediate consumption, and, based on the image, access a database comprising Nutrition Facts data for the food or beverage product for immediate consumption, the wearable device further comprising a timer configured, when the food or beverage product for immediate consumption is being dispensed, to determine when a food or beverage product dispensing operation has begun, when the food or beverage product dispensing operation has ceased, the time of the food or beverage product dispensing operation, the wearable device further configured, based on the Nutrition Facts data, the time of the food or beverage product dispensing operation, and the volumetric or mass flow rate data, to determine Nutrition Facts for, and display via the wearable device display a virtual Nutrition Facts label corresponding to, the food or beverage product for immediate consumption.

According to another aspect, the disclosure describes a system comprising a self-service food vessel, a measurement module configured to determine a measurement of a serving of a self-service food provided by the self-service food vessel, and a display communicatively coupled with at least one of the measurement module and the self-service food vessel, the display configured to display calorie information of the serving of self-service food based on the measurement and calorie information for the self-service food.

BRIEF DESCRIPTION OF THE DRAWINGS

The present disclosure is illustrated by way of example and not limited in the accompanying figures, in which like reference numerals indicate similar elements throughout, and in which:

FIG. 1 is an illustrative embodiment of a beverage bottle of the prior art.

FIG. 2 is an illustrative embodiment of a beverage bottle with a label of the disclosure.

DETAILED DESCRIPTION

Figure 3:
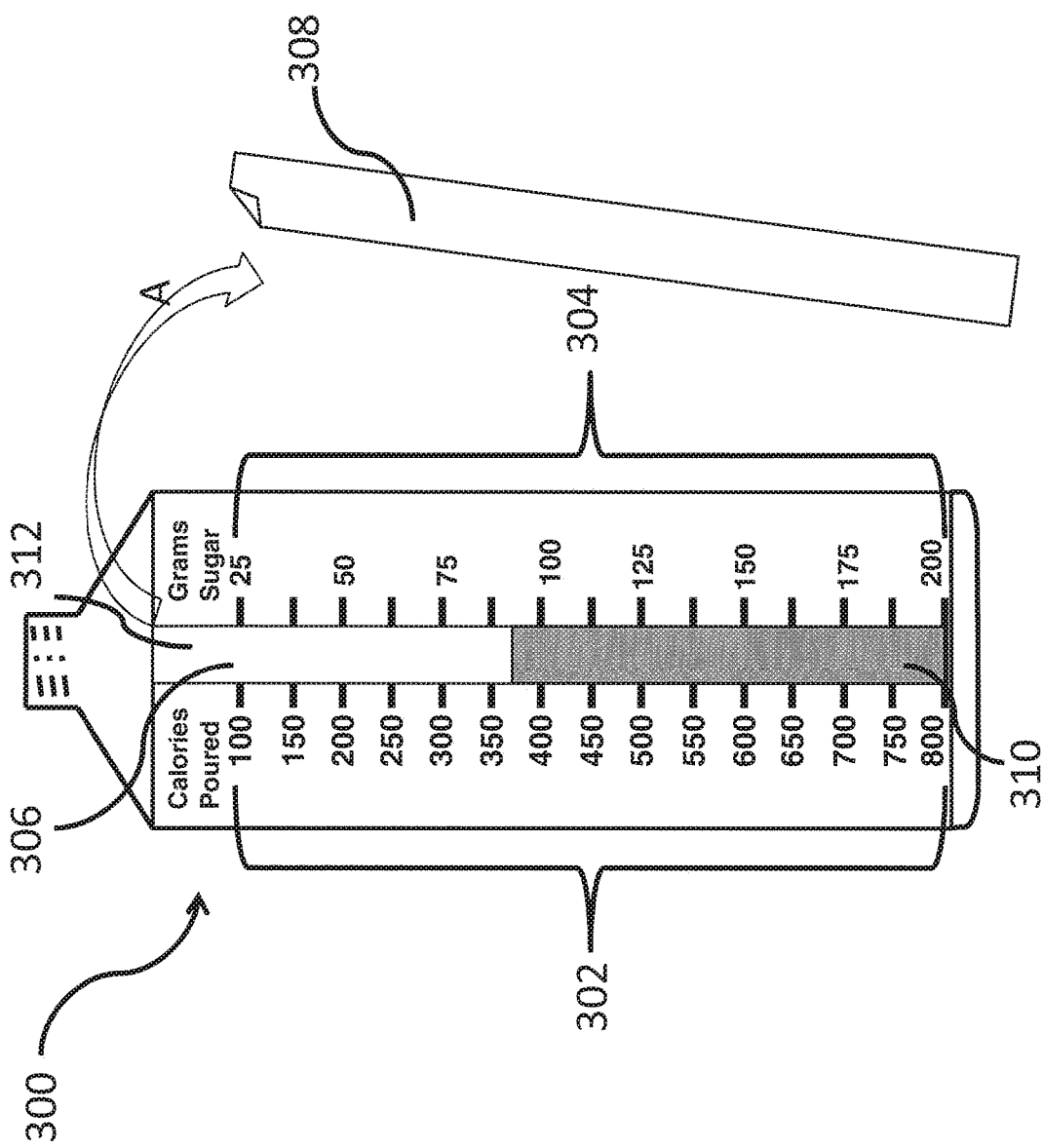
FIG. 3 is an illustrative embodiment of a package with a label of the disclosure.

Referring to FIG. 1 there is illustrated a container, generally 100, of the prior art, which may comprise, for example a beverage bottle having a finish section 110 comprising threads for receiving a closure (not shown), and a label section 112 comprising a generally cylindrical surface 114 for receiving a shrink wrap or other known product label. The container 100 may be fabricated of glass, PET, aluminum, or other known packaging materials.

Referring now to FIG. 2, there is illustrated a container of the present disclosure, generally 200, that may comprise a label 202, which label may comprise graduated indicia 204 thereon. While the container 200 is illustrated as a beverage bottle, it will be understood that the term "container" as used herein, unless otherwise modified, is intended to mean any vessel into which a food or beverage product may be dispensed, whether for future consumption or immediate consumption.

As illustrated, the graduated indicia 204 may comprise a plurality of graduated visual indicators, and at least one of the plurality of graduated visual indicators may be intended to correspond to and display a calorie count 206 and/or another ingredient attribute, such as a sugar count 207 of a food or beverage product 208 contained in and/or poured from the container 200, at a time when a level 210 of the food or beverage product 208 contained in the container 200 substantially corresponds to a level 212 of at least one of the plurality of graduated visual indicators.

As illustrated, the container 200 may comprise a label 202 that may comprise a substantially transparent portion 214 intended to enable viewing of the level 212 of the food or beverage product 208 contained in the container 200 and to enable comparison thereof to the at least one of the plurality of graduated visual indicators 212.

The substantially transparent portion 214 may comprise a sidewall of the container 200 if the container 200 is transparent or translucent, in which case, the label 202 may comprise a cutout portion 216 through which the food or beverage product 208 may be viewed. Alternatively, rather than the label 202 transparent portion 214 comprising a cutout portion 216, the transparent portion 214 may comprise a substantially transparent region of the label 202, intended to enable viewing of one or more levels of the food or beverage product 208 in the container 200. Such transparent portion 214 of the label 202 may be achieved, for example, using known label printing methods, whereby a transparent label material, such as a polymeric film, is printed with an opaque ink in some sections, while leaving other sections either unprinted or printed only with a transparent or translucent ink. Alternatively, the entire label 202 or a substantial portion thereof may be transparent or translucent, with the graduated visual indicators being printed in a color and/or prominence that is visible relative to the food or beverage product intended to be dispensed into the container 200.

The container 200 may comprise a glass or plastic beverage container comprising a label panel 220 having a top border 222 and bottom border 224, and the label 202 and the substantially transparent portion 214 may extend substantially from the top border 222 to the bottom border 224.

While the label 202 of FIG. 2 illustrates two categories comprising a plurality of graduated visual indicators for calories and grams of sugar, it will be readily appreciated that additional such categories may be displayed, potentially circumscribing most or even all of the container 202, i.e., with multiple columns of transparent portions 214, and/or multiple columns of graduated visual indicators for multiple ingredient attributes, such as: an amount, by weight or % daily value, of sugar, added sugar, sugar alcohol, sodium, total fat, saturated fat, trans fat, polyunsaturated fat, monounsaturated fat, cholesterol, potassium, total carbohydrates, fiber, dietary fiber, protein, vitamins, and/or minerals, of a food or beverage product to be contained in the container, at a time when a level of the food or beverage product to be contained in the container substantially corresponds to a level of the at least another of the plurality of graduated visual indicators.

Referring now to FIG. 3 there is illustrated a container generally 300, which may comprise, for example, an aseptic package such as that used to package shelf stable natural beverages such as coconut water. In this aspect, there may be provided a first plurality of visual indicators 302 intended to correspond to calories poured from a filled container 300, and/or a second plurality of visual indicators 304 intended to correspond to a quantity of an ingredient attribute such as grams of sugar poured from the container 300. Additionally or alternatively, the plurality of visual indicators 302, 304, may be intended to correspond to calories and grams of sugar, respectively, remaining in the container 300. The plurality of visual indicators 302, 304 may be printed, stamped, embossed, or painted directly onto the container 300, for example, during the manufacturing process.

As illustrated, the container of FIG. 3 may also comprise a viewing region 306 intended to enable the level of a food or beverage product in the container 300 to be viewed or approximated. When the container 300 comprises an aseptic package, such a viewing region 306, if transparent, may need to be fabricated of a sufficiently robust material of sufficient thickness to withstand the aseptic packaging process and insure sufficient shelf stability, often up to a year or more. Such materials, for example, may include PET or other plastic commonly used in the so-called "hot-fill" bottle filling processes. In this aspect, the viewing region 306 may be glued to the internal walls of the aseptic package comprising the container 300 using a glue suitable for the purpose, which may be the same or similar to glues currently used to fabricate aseptic packages and secure the seams thereof and/or secure spouts thereto. As food or beverage products packaged in aseptic packages may have their shelf stability adversely affected by light, the viewing region 306, if transparent or translucent, may be covered with a peel-off section 308 that may be opaque or otherwise light or microbe inhibiting, and may be adhesively applied to the container 300 during manufacturing or filling, and peeled off the container 300, i.e., by the consumer, as illustrated by arrow A, for example, after the container 300 has been purchased or opened. In a preferred aspect, the adhesive used for applying the peel-off section 308 may enhance the aseptic properties of the container 300 in viewing region 306.

Alternatively, the region 306 may comprise a thermochromic material, such as a thermochromic ink that may change color in response to the container 300 experiencing a temperature variation. Such inks are known in the beverage industry, i.e., being used on Coors Light beer cans or bottles. The ability of something to change color with temperature is known as thermochromism, and the Coors Light bottles are printed with a thermochromic ink called a leuco dye. A leuco dye is a coloring agent which can acquire two different forms: a colorless form and a colored form. At warm temperatures, the thermochromic ink is colorless, and at cold temperatures, the thermochromic ink is (in this case) blue.

In a preferred aspect, a thermochromic ink when used according to the present disclosure should be one tending to change from the one color or a colorless form to a second color or colored form relatively promptly, consistent with small changes in the temperature of the container in the sub-region 312 not having a chilled (or hot) food or beverage product therein and a sub-region 310 still having such a food or beverage product therein.

In this aspect, a thermochromic ink printed in the region 306 may comprise a first color when the container contains a chilled or heated food or beverage, and a second color (or no color) when the container 300 contains a food or beverage that is not chilled or heated, or when the container is at or approaching ambient temperature. Thus, as a chilled or heated food or beverage is consumed from the container 300, that portion of the container still containing the chilled (or heated) food or beverage may remain sufficiently cold (or hot) for the thermochromic ink to continue displaying the first color, illustrated at sub-region 310 in FIG. 3, while that portion of the container region 306 that has been emptied of the chilled (or heated) food or beverage, illustrated at sub-region 312, may revert to the second color (or no color) as the container 300 may tend to more quickly approach ambient temperature conditions in that region.

Figure 4:
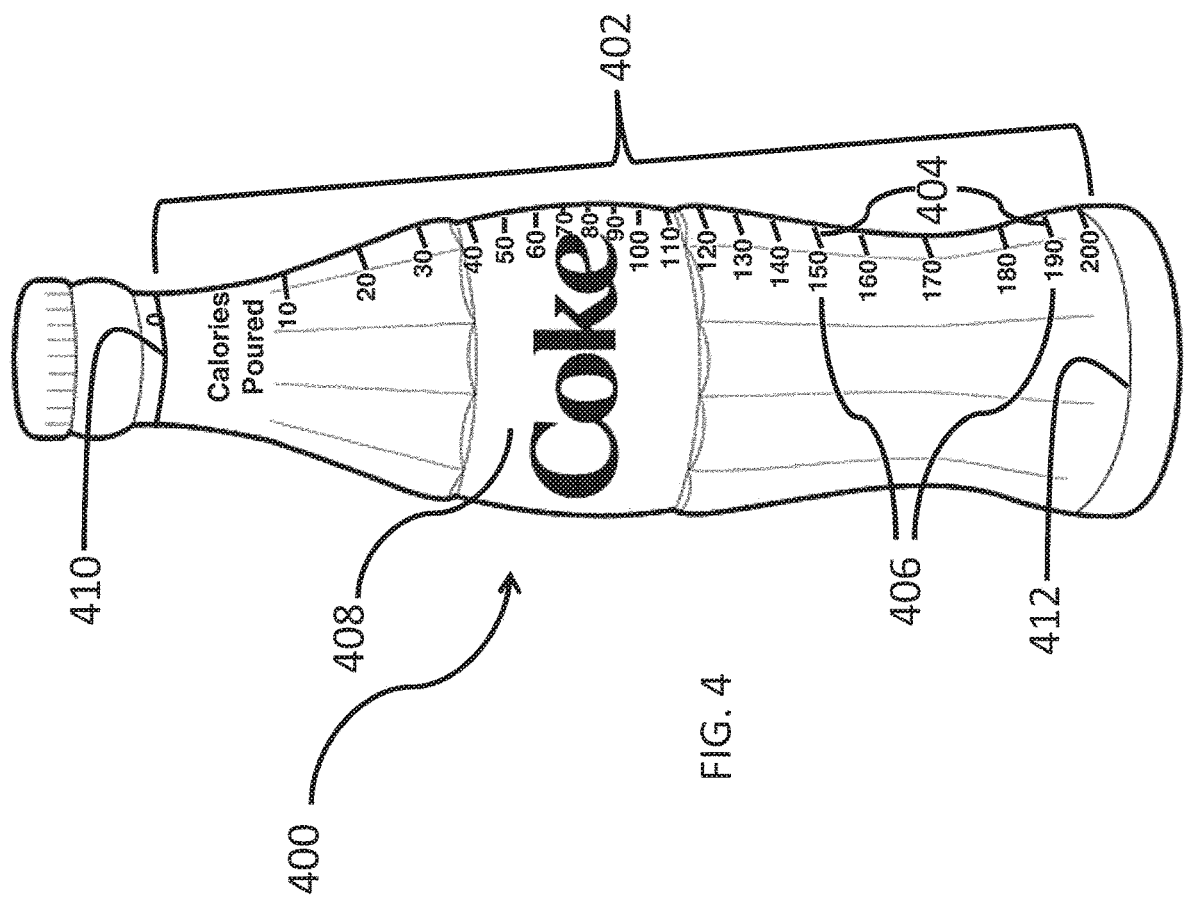
FIG. 4 is an illustrative embodiment of another beverage bottle labeled according to the disclosure.

Another aspect of the disclosure is illustrated in FIG. 4. In this aspect, a container, generally 400, may comprise a bottle, such as a glass or PET beverage bottle. As illustrated, the container 400 may comprise a plurality of visual indicators 402 comprising a series of graduated lines or markings 404 and corresponding numerical markings 406. Because, in this example, the container has an irregular shape, i.e., it is not cylindrical or of equal cross sectional area along its length, the series of graduated lines or markings 404 are not evenly distributed. As illustrated, the container may be filled with a food or beverage 408 having a fill line 410. As illustrated, the plurality of graduated visual indicators 402 may be placed directly on the container 400, for example by being printed or painted on the container 400, and may provide an indication of an ingredient attribute for the food or beverage 408 for substantially the entire portion of the container 400 from the fill line 410 to the bottom 412 of the container, as illustrated. In this example, the graduated visual indicators 402 display calories poured or consumed, although other ingredient attributes may of course be displayed, including ingredient attribute quantities remaining in the container 400. In another alternative, a thermochromic ink or other material may be used to print or paint the graduated visual indicators 402 on the container. Alternatively, the plurality of visual indicators 402 may be molded into the container 400.

Figure 5:
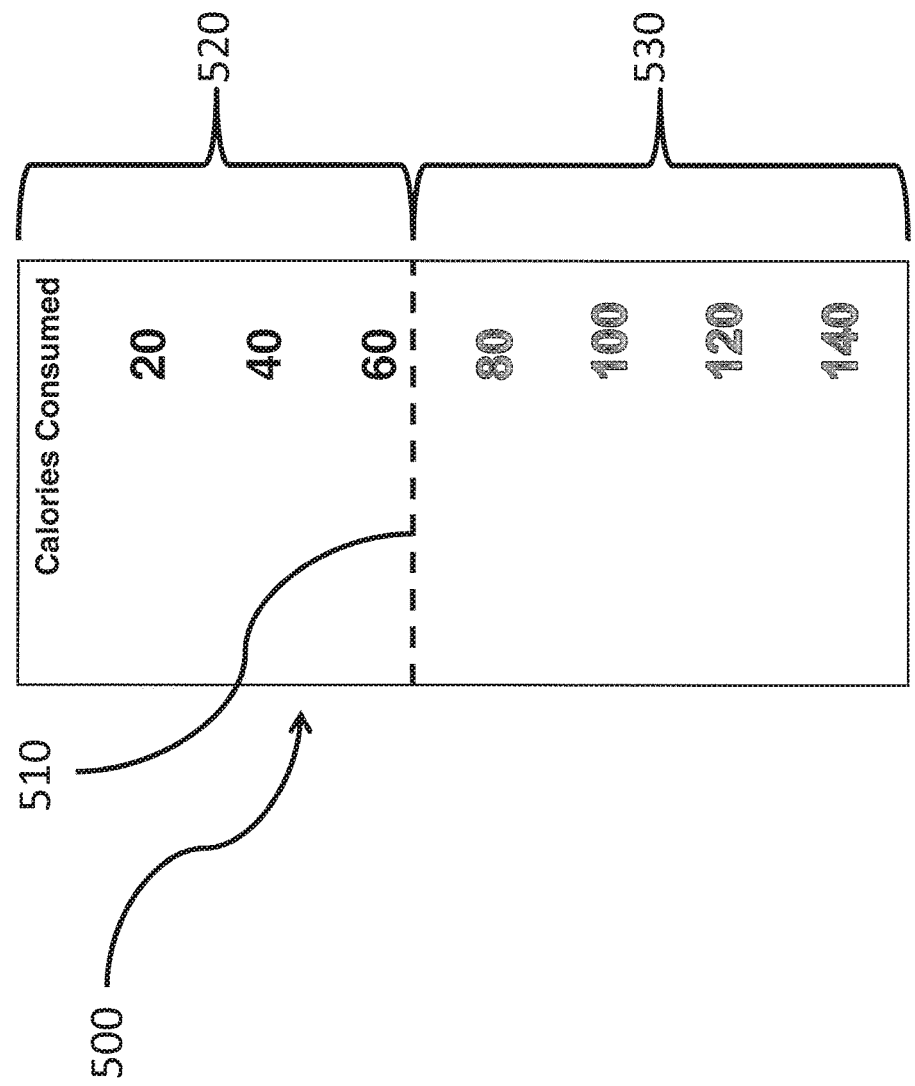
FIG. 5 is an illustrative embodiment of a label according to the disclosure.

Referring now to FIG. 5, there is illustrated a schematic representation of a container, generally 500, having thermochromic ink visual indicators thereon, illustrating how an opaque container, such as a can of a food or beverage, may nonetheless permit a level 510 of a food or beverage product container therein to be approximated and one or more ingredient attributes corresponding to that level determined. In this example, a first region 520 of the container 510, corresponding to an emptied portion of the container 510 may achieve or approach ambient temperature more quickly than a second region 530 of the container 510, corresponding to a portion of the container still containing a food or beverage product that is not at ambient temperature. In this aspect, the container may, for example, comprise visual indicators that are printed in a first color ink, i.e., black, and overprinted with a thermochromic ink that is colorless at ambient temperature, but turns blue, for example, at a chilled temperature. Thus, in this example, as a chilled beverage is consumed, and the first region 520 approaches ambient temperatures, the thermochromic overprinted ink may turn from its chilled blue color to colorless, revealing the under-printed color, in this case black.

Figure 6:
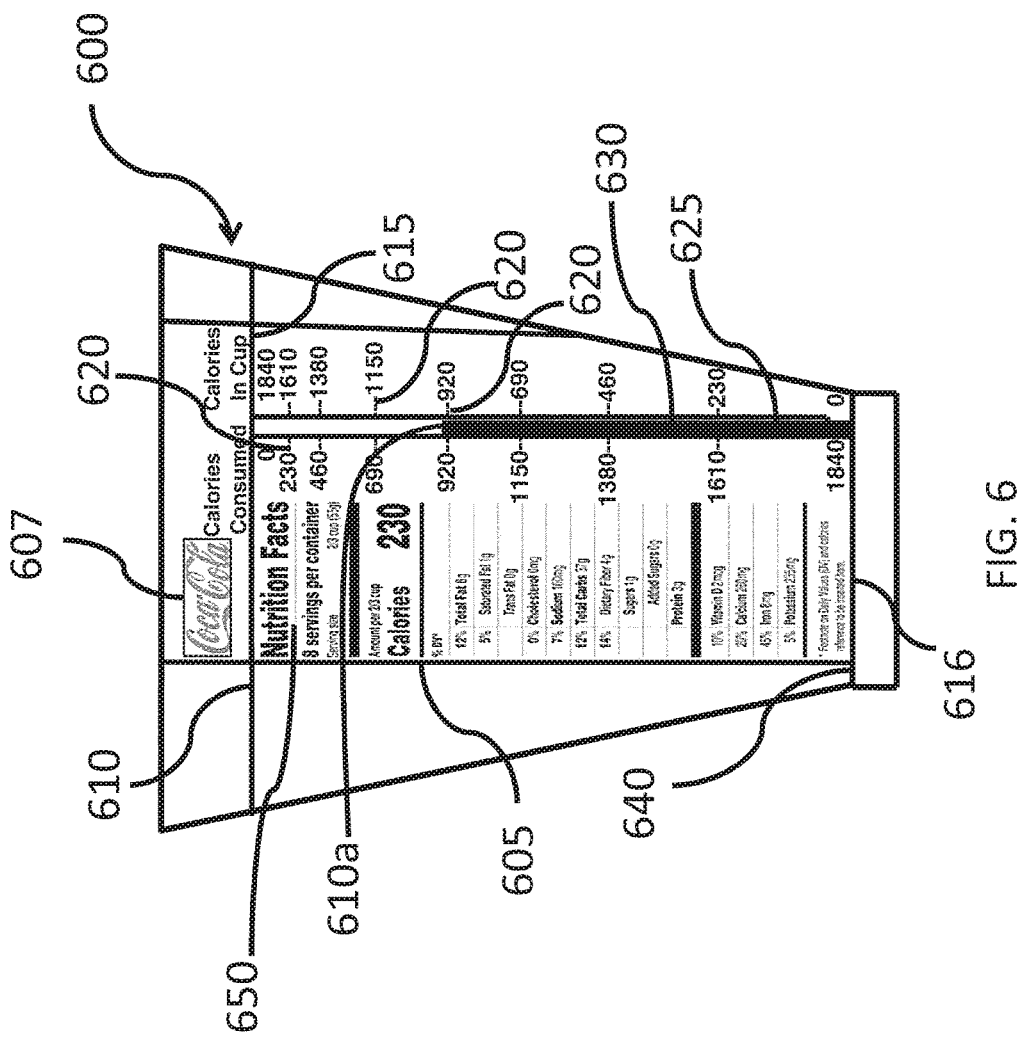
FIG. 6 is an illustrative embodiment of a food or beverage container labeled according to the disclosure.

Referring now to FIG. 6 there is illustrated a preferred aspect of the present disclosure, comprising a container, such as a beverage cup or glass, generally 600. In this aspect, the container 600 may have applied thereto a label 605 as shall now be described. As illustrated, the label 605 may, as described in co-pending U.S. patent application Ser. No. 14/335,855, be prepared by printing, employing systems, methods, and apparatus as described therein in order to print Nutrition Facts on the label 605, the Nutrition Facts corresponding to a product, such as a food or beverage product for immediate consumption, that has been dispensed into the container 600, for example a beverage dispensed via a Freestyle® dispensing machine of The Coca-Cola Company. In this aspect of the present disclosure, the label 605 may be further configured to display ingredient attribute indicator markings 620 for one or more ingredient attributes, in this example, calories of product consumed from, and/or remaining in, the container 600. As will be described, using the systems, apparatus, and methods of the present disclosure, such ingredient attributes can be accurately determined irrespective of ice being placed in the container or foaming of the product, as generally occurs upon dispensing a carbonated beverage.

As illustrated, the container 600 may, at the conclusion of a product dispensing operation, result in an initial fill line 610 corresponding to the level of food or beverage product in the container 600 upon completion of the dispensing operation. As further illustrated, the label 605 may be configured with an alignment indicator, such as an upper indicator line 615, intended to substantially correspond to the initial fill line 610, for example, when the label 605 is applied to the container 600. The label 605 may be further configured with one or more ingredient attribute indicator markings 620 intended to correlate prior and/or subsequent product fill lines with one or more product attributes of product consumed from and/or remaining in the container 600, in this example calories consumed and calories remaining in the container 600. The label 605 may contain branding indicia 607 specific to the food or beverage product intended to be dispensed in the container 600 and/or the organization authorizing the labeling of the container.

As further illustrated, the label 605 may be configured with a viewing portion 625 comprising a separation, transparent or translucent material, opening, or slot through which product 630, for example a dark colored beverage such as a Coca-Cola beverage, contained in the container 600, and in particular the level of such product as it is being filled and/or consumed, i.e., intermediate fill line 610*a*, may be more readily viewed. Such a viewing portion 625 may be desirable particularly when the container does not comprise a transparent container such as a glass or clear plastic cup, rather, comprises a thin-walled paper or polystyrene cup that permits sufficient light transmission to visually approximate the initial fill line 610 and align the upper indicator line 615 of the label 605 therewith when the label 605 is being applied to the container 600. As illustrated, the viewing portion 625 may run all or substantially the entire length of the container 600, and in a preferred aspect may run from at least from the initial fill line 610 to the bottom of the container 640.

Alternatives to the viewing portion 625 will now be readily apparent, and may, for example, include a series of holes, openings, or perforations in the label 605. In another aspect, the label 605 may be printed on transparent film, obviating any need for a viewing portion 625. In yet another aspect, the upper indicator line 615 may simply comprise the top edge of the label 605, which may be aligned on the container 600 such that the top edge of the label is positioned substantially at the fill line 610.

Alternatively or additionally, the label 605 may have a lower indicator line 616 which may be the lower border of the label 605. When a lower indicator line 616 is used, the label 605 and container 600 may more readily be used, for example, to provide an accurate series of ingredient attribute indicator markings 620 when the product 630 comprises a foaming product such as a carbonated beverage, i.e., a carbonated soft drink, beer, etc. As is known, foaming food or beverage products, such as carbonated beverages, whether beer, soda, carbonated water, or otherwise, tend to foam at the end of the dispensing cycle and to settle a short time after the dispensing cycle has concluded. In one aspect of the disclosure, the label 605 may be printed from the "bottom up" during the printing operation, with the ingredient attribute indicator markings 620 printed according to the weight or volume of product 630 being dispensed into the container 600. In this aspect, a label 605 applied to the container 600 right after the dispensing operation, at a time when the foaming is greatest, may nonetheless reflect relatively accurate attribute indicator markings 620 once the foaming settles.

In a preferred aspect, for example, when an alcoholic product such as beer (which tends to maintain a foam "head" for a longer duration than soft drinks) is being dispensed, the label 605 may be printed from the bottom up, and instructions given to apply the label 605 such that the first ingredient attribute indicator marking 620 aligns with the bottom of the container, in which case, the attribute indicator markings may comprise calories and/or grams of alcohol consumed. The dispenser in this example from which the beer was dispensed may comprise one or more of a volume indicator to assist in printing the label 605 and/or an algorithm for calculating the amount of foaming attributable to a total volume of beer dispensed. From this foaming calculation a foam height may be determined and appropriate label adjustments made to account for that portion of the calories and/or alcohol for the total pour attributable to the foam.

Additionally or alternatively, the label 605 may be printed or prepared with reference to ice having been dispensed in the container 600. In this aspect, ice adds only volume, not ingredient attributes such as calories or grams of sugar to the resulting beverage. It may be assumed that any added ice will have a volume approximately the same as water, and that eventually all the ice will melt in the beverage. In this aspect, the printer that prints or prepares the label 605 may simply add the volume of ice added to the cup and print the label as if the relevant ingredient attribute indicator markings were being prepared for a beverage that had been watered down and dispensed with a quantity of water equivalent to the volume of ice added. The volume of added ice may be determined either by a volumetric control or a weight control device, including, for example, ice dispensers such as those used in the Vitamix Portion Blending System® Advance® 2.0, commercially available from Vita-Mix Corporation, 8615 Usher Road, Cleveland, Ohio 44138, which rely on a scale positioned beneath the blender container to apportion known quantities of ice. Alternatively, a level indicator, as subsequently described, may, in combination with a volumetric control device that measures the amount of beverage product 630 dispensed into the container 600, determine the top level of the beverage/ice mixture, and, based on the volumetric geometries of the container, the total volume of beverage/ice mixture added to the container 600 may be determined. Working backwards from the total volume of beverage/ice mixture added to the container 600, and how, based on the geometric parameters of the container the height thereof varies with volume, and knowing the amount of ingredient attributes per unit volume of the beverage or beverage/ice mixture, a label 605 with graduated ingredient attribute indicator markings 620 corresponding to like levels of the beverage or beverage/ice mixture in the container 600 may be prepared.

As further illustrated in FIG. 6, the label 605 may further comprise a Nutrition Facts section 650 in addition to the ingredient attribute indicator markings 620 and viewing portion 625. Such Nutrition Facts section 650 may itself comprise an FDA approved Nutrition Facts label displaying, inter alia, servings per container, serving size, calories per serving, calories per container, etc., specific to the food or beverage product dispensed into the container 605, which Nutrition Facts section may be prepared for a food or beverage product for immediate consumption substantially as disclosed in co-pending U.S. patent application Ser. No. 14/335,855.

The label 605 may be configured with an adhesive backing that may allow the label to be applied to the container 600. In one aspect, the label 605 may comprise an adhesive backing that requires moistening for adherence, which moistening may be achieved by virtue of condensation on the container 605 when a chilled beverage is present therein. In another aspect, the adhesive backing may comprise a peel and stick type label similar to those used for airline luggage tags or a self-adhering label such as those used for deli food labels. In still another aspect, the label 605 may be printed directly onto the container 605.

Figure 7:
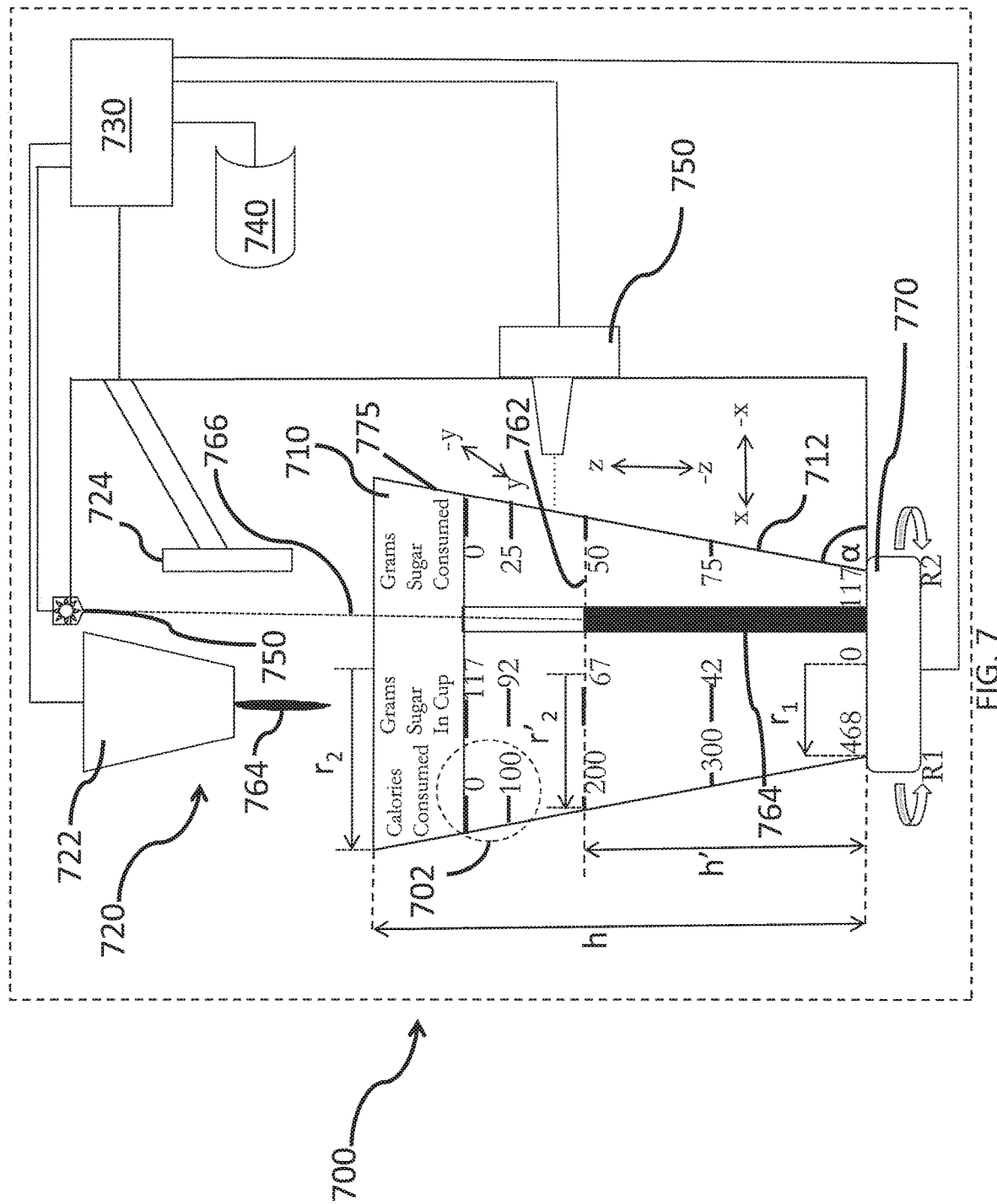
FIG. 7 is an illustrative embodiment of a food or beverage dispensing and labeling system of the disclosure.

Referring now to FIG. 7, there is illustrated an exemplary system, generally 700, which may be used for printing a label of the present disclosure, such as label 605 of FIG. 6, although it will now be readily apparent to those of ordinary skill in the art that other systems may be employed to achieve the same or substantially the same labels as disclosed herein. The system of FIG. 7 may provide a label to be applied to a container 710 and/or may provide a label printed directly on the container 710. As illustrated, the container 710 may comprise a cup with a frustoconical configuration, also known as a conical frustum, i.e., a cone section with the top portion cut off perpendicular to its axis.

The system 700 may comprise a self-service food vessel, such as, for example, a food or beverage dispenser, generally 720, such as the Coca-Cola Freestyle dispenser, configured as disclosed herein. While food or beverage dispenser 720 is shown, a self-service food vessel may comprise a holder which may be defined by at least one surface capable of retaining or restricting the flow or movement of at least one food or beverage, and which may be accessible, operable, manipulable, or otherwise capable of being interacted with by a user, directly and/or indirectly, to obtain, deliver, serve, dispense, receive, secure, purchase, gather, distribute, and/or realize a food or beverage of the holder. The holder may, for example, comprise a plurality of chambers, which may be in a controllable or uncontrollable and regulated or unregulated connection, such as a fluid connection.

The food or beverage dispenser 720 may comprise a dispensing nozzle 722 and an actuator 724 such as a lever for dispensing ice and/or the food or beverage product. Alternatively, or additionally, the food or beverage dispenser may comprise a user interface, such as a display with a graphical user interface, as is known, for selecting and/or dispensing the food or beverage product. The system 700 may further comprise a control device 730 such as a microprocessor or controller, a database 740, and a printing device 750. The food or beverage dispenser 720, as is known, may comprise further devices and systems not shown, for example, a water source, macro-ingredient sources, micro-ingredient sources, pumps, metering devise or other types of flow devices that may cooperate to meter, blend, and dispense a food or beverage product through the dispensing nozzle 722.

The system 700 may further include a level indicator 760 for determining one or more fill heights, illustrated schematically by dotted line 762, of a food or beverage 764 being dispensed into, and/or contained in, the container 710. The fill heights thus determined may be used to instruct the control device 730 to print a visual indicator corresponding to the fill height, to be printed directly on the container 710 and/or on a label to be applied to the container 710. The level indicator may 760 comprise known apparatus, i.e., ultrasonic level indicators. Such devices employ ultrasonic pulse signals that are transmitted and reflected from the liquid surface. The transmitter 'listens' for reflected signals (echoes), illustrated schematically by dotted line 766, and measures the time-delay between transmitting and receiving. The distance to the liquid surface is automatically calculated using the computed time-delay. An integral temperature sensor continuously measures the air temperature around the transmitter. It then computes the speed of sound in air, automatically compensating the distance for temperature effects. Commercially available level sensors include, for example, those available from Rosemount 3101 ultrasonic level transmitter, designed for simple level or distance measurements over a range of 1 to 26 feet and a 4-20 mA signal output. Another example, available from Flowline Inc., 10500 Humbolt Street, Los Alamitos, Calif. 90720 U.S.A., is the Flowline EchoPod DL14 Ultrasonic Level Sensor, a non-contact ultrasonic level switch, controller, and transmitter for small applications, which is accurate to 0.125" (3 mm). Other fluid level sensors, for example those available for laboratory or bench use, i.e., to measure fluid levels of small volumes, may likewise be advantageously employed. Another example of a liquid level sensor that may be employed in the present application is discussed in a paper by Paul H. Dietz, Darren Leigh, and William S. Yerazunis, entitled "Wireless Liquid Level Sensing for Restaurant Applications," published by The Mitsubishi Electric Information Technology Center America, (April 2002), incorporated in its entirety by reference herein. This paper discusses glassware that detects fluid levels via high-resolution capacitance measurement. A coil embedded in the table (or in this case a base on which the container 710 rests during dispensing) inductively couples power to the container, providing a path for data exchange. Other level sensors, including, for example, those relying on laser technology to scan the outside of the container to determine a liquid level therein, are of course possible.

As illustrated, the container 710 may have a plurality of visual indicators, 702, which may comprise, for example, graduated indications and/or numerals intended to display calories and/or grams of sugar consumed and/or remaining in the container 710 with respect to multiple fill heights of the food or beverage 764 being dispensed into or contained in the container 710.

One of the issues associated with printing a label with graduated indicators to indicate the number of calories or other ingredient attributes associated with a fill line for application to a container for a food or beverage product for immediate consumption is that the food or beverage product may contain air, carbonation, foam, etc., tending to complicate any effort to correlate container volume and container height with quantity of food or beverage dispensed into the container for immediate consumption. Further complicating providing such labels is the tendency, in the case of soft drinks and other dispensed beverages, for the consumer or crew worker to dispense ice into the container prior to, during, or after the filling operation.

The present disclosure may address one or more of these issues, as set forth in the following Example.

Example 1

Assume a hypothetical carbonated beverage product ("Beverage A") to be dispensed from a dispensing machine, such as a Coca-Cola Freestyle dispenser, is known to have a calorie count of 100 calories per 8 fluid ounce serving (237 ml or cc). Assume it is also known that during the dispensing operation, a high fructose corn syrup-based (HFCS) sweetener system will be employed, and diluted at a volumetric ratio of 5:1 carbonated water to HFCS. Assume further, for simplicity, that the HFCS sweetener system is the only significant source of calories in Beverage A, and that other ingredients, such as flavorings, salt, minerals, vitamins, etc., (sometimes referred to as "micro-ingredients") contribute insignificantly to the total volume of Beverage A and indeed may be dispensed toward the end of the dispensing operation. Assume further that the dispensing machine is configured to determine the weight of volume of HFCS sweetener system and/or weight or volume of carbonated water being dispensed in real time. Assume further that it is desired to prepare visual indicators to be applied to a container in which Beverage A will be dispensed, for example, comprising graduated level indicators in 10-calorie increments intended to approximate calories consumed from the container in which Beverage A is to be dispensed. Assume also that the container into which Beverage A will be dispensed is frustoconical in shape, (also known as a conical frustum) as illustrated as container 600 in FIG. 6 and container 710 in FIG. 7, and of known volume at any fill height. The volume of Beverage A at any instantaneous point during a filling operation, and hence correlating a fill height to a product attribute such as calories dispensed into the container, may be predetermined using various relationships.

The volume of a conical frustum beverage container 710 in FIG. 7 is expressed as:

$$V = (1/3) * \pi * h * (r_1^2 + r_2^2 + (r_1 * r_2))$$

Where $r_1$=radius of container base,
$r_2$=radius of container top,
h=height of container from base to top,
V=volume of entire container, and
$\pi$=pi=3.14159.

The volume of a food or beverage 764 contained in the container 710 below the top thereof for example, may be expressed, with respect to the container 710 of FIG. 7 as:

$$V' = (1/3) * \pi * h' * (r_1^2 + r_2'^2 + (r_1 * r_2'))$$

Where $r_1$=radius of container base,
$r_2'$=radius of container at fill line of Beverage A,
h'=height of container from base to fill line of Beverage A,
V'=volume of Beverage A dispensed into container 710, and
$\pi$=pi=3.14159.

Similarly, the volume of a food or beverage 764 at any instantaneous point in time (1−n) during the filling operation may be represented as:

$$V_{(1-n)} = (1/3) * \pi * h_{(1-n)} * (r_1^2 + r_{2(1-n)}^2 + (r_1 * r_{2(1-n)}))$$

Where $r_1$=radius of container base,
$r_{2(1-n)}$=radius of container at an instantaneous fill line of Beverage A at corresponding instantaneous fill heights $h_{(1-n)}$,
$h_{(1-n)}$=height of container from base to instantaneous fill lines of Beverage A at measurement times (1−n), and
$\pi$=pi=3.14159;
$V_{(1-n)}$=instantaneous volume of Beverage A dispensed into container 710 at measurement times (1−n).

Assume that the food or beverage dispenser 720 dispenses Beverage A at a rate of 23.7 ml (cc) per second, meaning it would take 10 seconds to dispense an 8-ounce, 237 ml serving of 100 calories. Thus, the food or beverage dispenser 720 would dispense 10 calories per second of Beverage A. Assume that container 710 has a height h of 5 inches or 12.7 cm, a top radius $r_2$ of 3.5 inches or 8.9 cm, and a base radius $r_1$ of 2 inches, or 5.1 cm. For an ideal Beverage A, therefore, in order to mark the container 710 with graduated visual indicators for every 10 calories dispensed, the printing device 750 may be configured to print graduated visual indicators at a level of Beverage A, as determined by the level indicator 760, every second after the dispensing operation has commenced. For such a dispenser, the following relationship applies: $V_{(10\ cal)}$=237 ml/100 cal×10 cal=23.7 ml (cc).

The height of the beverage in the container corresponding to this volume will be readily determined by the level indicator 760, which may, in this example, be configured to transmit a level $h_{(1-n)}$ to the control device 730 every 10 seconds, for example. Of course, as will now be readily appreciated, the level indicator 760 may be eliminated if the controller 730 is configured, using, for example, integral calculus and trigonometry, the base radius $r_1$, the angle α of the container sidewall 712 relative to the horizontal (or vertical h), to determine the height $h_{(1-n)}$ of each successive visual indicator relative to successive 10-calorie dispenses of Beverage A into container 710, based on fill rate, volume, and container 710 geometric parameters. In this aspect, it will be readily appreciated that the container 710 and food or beverage product dispenser 720 may be configured with a reader, such as disclosed in published application US 2011/0049180 A1, incorporated by reference in its entirety herein, configured to read a bar code or other readable indicator on the container 710. In this aspect, the reader may be configured to determine, based on the bar code or other readable indicator, the geometric parameters of the container 710 such that the relevant fill heights associated with a predetermined volume of dispensed product, and hence, an ingredient attribute associated with such predetermined volumes, may be determined and from that, the desired visual indicators may be determined and displayed on the container 710.

Alternatively, the system 700 may comprise user interfaces for selecting different size beverages, i.e., small, medium, and large, into three corresponding container sizes, i.e., small, medium, and large. The system 700 may be configured to predetermine, based on the known dispensing rate of the beverage dispenser 720 and/or the known volume geometries of the small, medium, and large containers, how fill height correlates to volume for a particular container. If, for example, a user selects a small beverage to dispense from the dispenser 720, the system 700 may assume that a small cup of known volume geometry will be used. The system may, for example, be preconfigured to recognize how volume of product dispensed correlates to a fill height in a small cup from the bottom of the cup. The following table illustrates fill volumes and approximate corresponding fill heights from the bottom of the cup, and corresponding calories for a hypothetical beverage containing 100 calories per 237 ml as dispensed into a polystyrene Dart® beverage cup comprising a frustoconical configuration, bearing numerals U05117 14J16, available from Chick-fil-A:

TABLE 1

| Fill Volume (ml) | Corresponding Fill Height of Cup (mm) | Calories |
|---|---|---|
| 0 | 0 | 0 |
| 50 | 19 | 21 |
| 100 | 35 | 42 |
| 150 | 49 | 63 |

TABLE 1-continued

| Fill Volume (ml) | Corresponding Fill Height of Cup (mm) | Calories |
|---|---|---|
| 200 | 63 | 84 |
| 250 | 75 | 105 |
| 300 | 84 | 126 |

Based on this predetermined relationship, the system 700 may be configured to print out a label, or print directly onto the container, graduated visual indicators corresponding to the above fill heights and calorie counts. In this aspect, such a label or printed indicators could be with reference to the top fill line, in which case the calories in Table 1 would represent calories remaining in the cup at each corresponding fill height, as opposed to calories consumed. To display calories consumed, the system 700 may be configured to simply invert the "Calories" indicators as illustrated in Table 1 for each corresponding fill height for printing onto a label or cup. Of course, the system may be configured to display calories in more convenient increments, such as 10 or 25 calorie increments.

As another alternative, the container may comprise a bar code, RFID device, or other identification device that may, when scanned or inputted, either at the food or beverage product dispenser, or at a remote location such as a crew server input device, communicate with the food or beverage product dispenser container-specific data pertaining, for example, to height, base radius, top radius, angle of the container sidewall, relationship of container height to container volume, etc., such that the food or product dispenser can readily determine, based on the filling rate of the container, i.e., ml/second, grams/second, etc., and the ingredient attributes per unit weight or unit volume of the food or beverage product being dispensed, where on a longitudinal label or display on the container to position and/or print graduated visual indicators of ingredient attributes specific to the food or beverage product being dispensed. Alternatively, for ease of use, the outlet in which the food or beverage dispenser is located may elect to use just one cup size such that the food or beverage dispenser need not have the container-specific data inputted for each serving, rather, may be configured to dispense into a single cup size of known container-specific data.

It will now also be readily appreciated that the system 700 database 740 may comprise lookup tables or other ingredient and/or recipe specific information for the food or beverage product selected to be dispensed into the container 710, and based on such data, and a fill rate, may be able to determine, for example, calories per second of dispense, grams of sugar per second of dispense, etc., for a food or beverage product of interest.

As illustrated in FIG. 7, the printing device 750 may be configured to print directly onto the container 710, for example, by providing the system 700 with a base 770 on which the container 710 rests, which base 770 may rotate in the directions of arrows R1 and R2, thereby allowing the printing device 750 to print onto the container 710 in a radial direction illustrated by arrows y, -y of FIG. 7. The printing device 750 may further be configured to move up and down, as illustrated by arrows z, -z, and in and out, as illustrated by arrows x, -x, thereby enabling printing onto a three dimensional surface, such as an angled round container surface 775.

Figure 8:
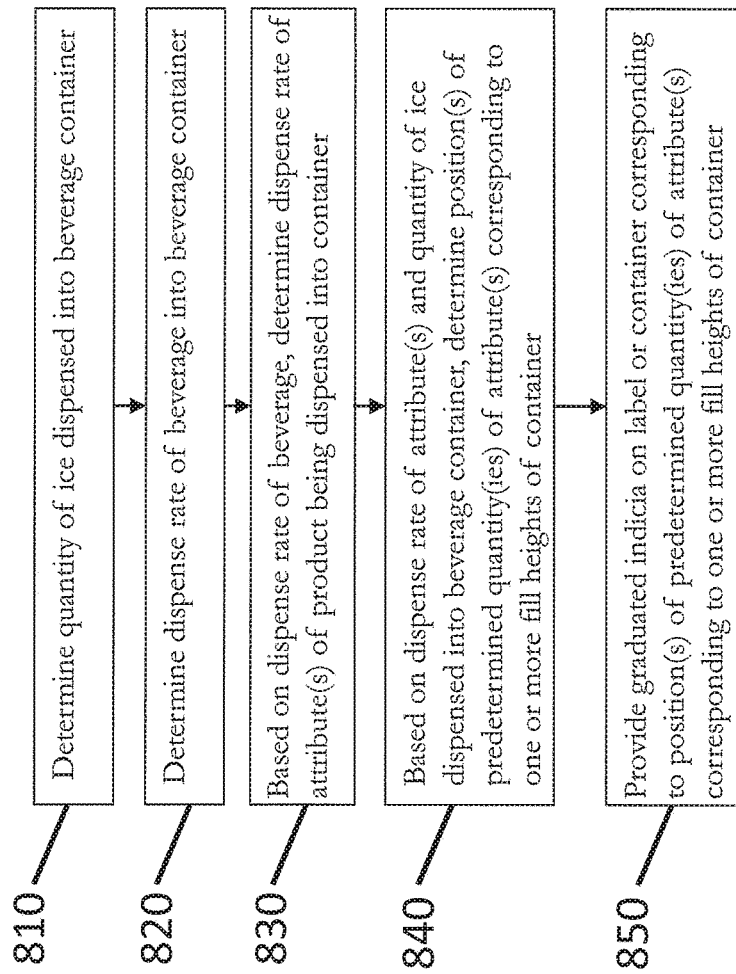
FIG. 8 is an illustrative embodiment of a method of the disclosure, which may be used, for example, with the system of FIG. 7.

FIG. 8 illustrates a method of the present disclosure that may be used to provide a label such as label 605 with graduated visual indicators that comprise relevant ingredient attribute indicators when a beverage container to which such label is applied contains ice. As is known, consumers using food or beverage product dispensers, such as the Coca-Cola Freestyle dispenser, typically dispense ice first into the container, before dispensing the beverage, in order to minimize foaming and splashing. The system 700 of FIG. 7 may be configured to determine, at operation 810, the quantity of ice dispensed into the beverage container. This may be done using known weight or volume control apparatus. The volume of added ice may be determined either by a volumetric control or a weight control device, including, for example, ice dispensers such as those used in the Vitamix Portion Blending System® Advance® 2.0, commercially available from Vita-Mix Corporation, 8615 Usher Road, Cleveland, Ohio 44138, which rely on a scale positioned beneath the blender container to apportion known quantities of ice. At operation 820, the system 700 may determine the dispense rate of the beverage into the beverage container. This may be done, for example, using known flow control devices incorporated into such beverage dispensers. At operation 830, the system 700 may, based on the dispense rate of the beverage, determine dispense rate of attribute(s) of product being dispensed into the container, container, i.e., 10 calories per second. At operation 840, based on the dispense rate of attribute(s) and quantity of ice dispensed into the beverage container, the system may determine the position(s) of predetermined quantity(ies) of attribute(s) corresponding to one or more fill heights of the container. For this operation, it may be assumed, for example, that the volume of ice corresponds to a like volume of water, and the final fill height, once determined, may be associated with the final ingredient attribute quantity. Based on this final fill height and the final ingredient attribute quantity, attribute quantities for lesser fill heights and the fill rate can be determined, again, it being assumed that whether the consumer consumes all the beverage before the ice melts or after the ice melts, the ingredient attributes and associated fill heights will approximately correlate to a beverage containing ice or diluted with melted ice. At operation 850, the system 700 may provide graduated indicia on the label 650 or container corresponding to position(s) of predetermined quantity(ies) of attribute(s) corresponding to one or more fill heights of the container.

Figure 9:
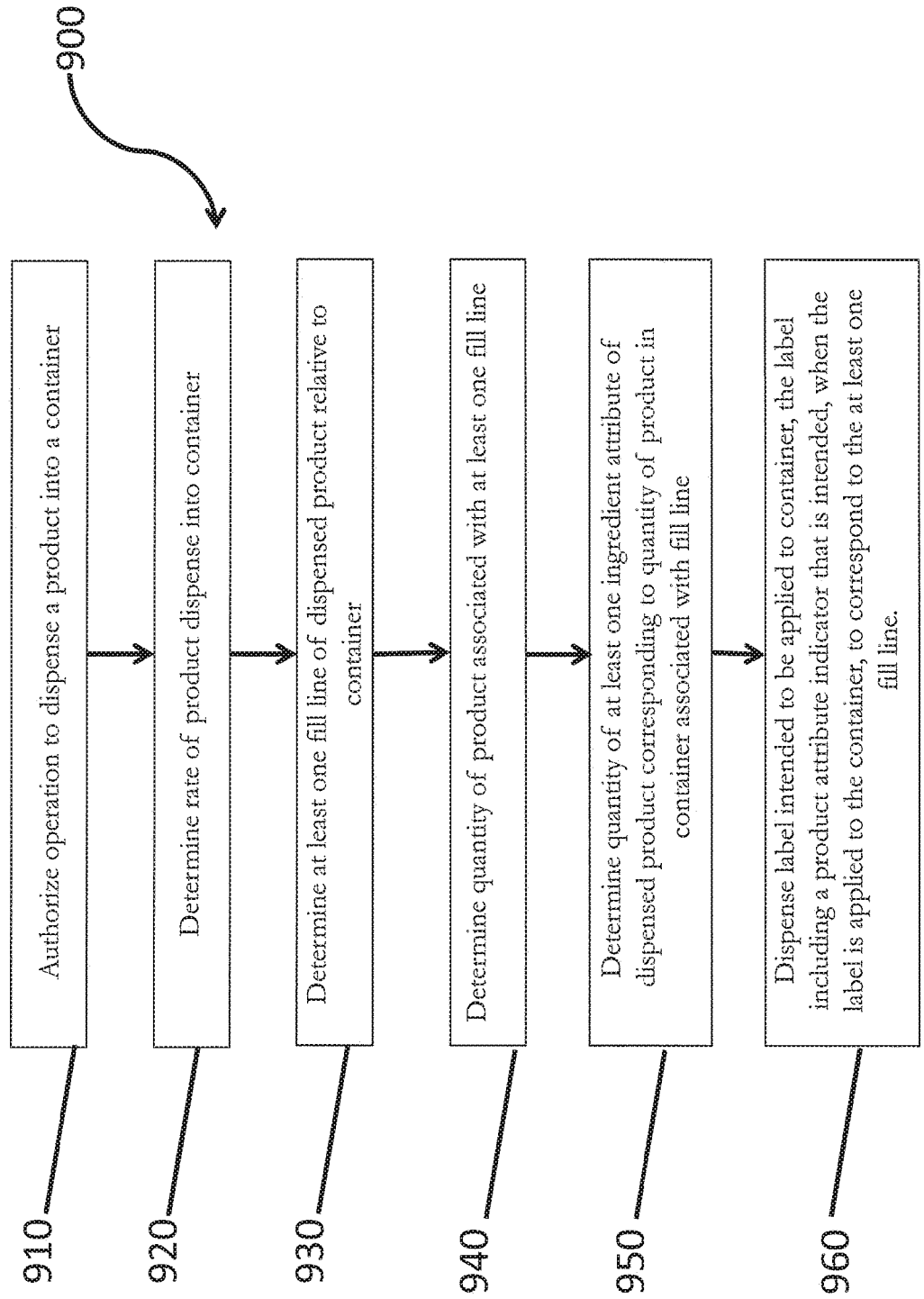
FIG. 9 is an illustrative embodiment of another method of the disclosure, which may be used, for example, with the system of FIG. 7.

Another method of the disclosure is illustrated in FIG. 9. In this aspect, the system 700 may authorize an operation to dispense a product into a container at operation 910. This may be done, for example, by a crew server, or at the point of sale, or by the consumer gaining authorization from a food or product dispenser, for example, using a mobile device electronic payment system such as Apple iPay. At operation 920, the system 700 may determine the rate of product dispense into a container. At operation 930, the system may, for example, as set forth herein, determine at least one fill line of dispensed product relative to the container. At operation 940, the system 700 may determine the quantity of product associated with at least one fill line. At operation 950, the system 700 may determine a quantity of at least one ingredient attribute of dispensed product, for example, number of calories, corresponding to the quantity of product in the container associated with the fill line. At operation 960, the system 700 may print on, or dispense a label intended to be applied to, the container, the label including a product attribute indicator that is intended, when the label is printed on or applied to the container, to correspond to the at least one fill line.

In other contexts, busy consumers may not wish to wait for a Nutrition Facts label, and/or a label with graduated visual indicators, to be adhered to or printed onto their cup, glass, pizza box, etc., and may wish, as is often the case of hurried consumers at a fast food outlet drive through window, for example, to merely grab their order and go. Or, it may be desirable to reinforce the messaging of a Nutrition Facts label applied to a food or beverage product. In such a scenario, it may be advantageous for the consumer's receipt to include thereon a Nutrition Facts label for each of the food and beverage products in the order. Such a receipt may be quickly and conveniently printed out and placed in the bag, in or on the box, or other carrying receptacle for the consumer to examine and consider at the point of consumption.

In one preferred aspect of the disclosure, a dispensing machine or other device associated therewith, such as a cash register, printer, etc., may, upon conclusion of a product dispensing operation, or at the conclusion of a product scanning and checkout operation, dispense a receipt that includes not only the price and quantity of product dispensed, such as is conventional at gasoline pump dispensing kiosks, but may also dispense, either as a separate sheet, or as part of a dispensed receipt, information related to at least one ingredient attribute of the dispensed product. For example, consumers in a grocery store, such as Whole Foods, often hand select products such as seeds, nuts, candy, etc., from bins and dispense them into bags, boxes, or other packages which, at checkout, are weighed, and based on the food item, priced per unit weight. According to an aspect of the present disclosure, the cash register may be configured, based on the weight of the item being purchased, to print out a Nutrition Facts label that may either be dispensed as a part of the receipt for the item, or may be dispensed as an adhesive label for application to the hand selected product.

Figure 10:
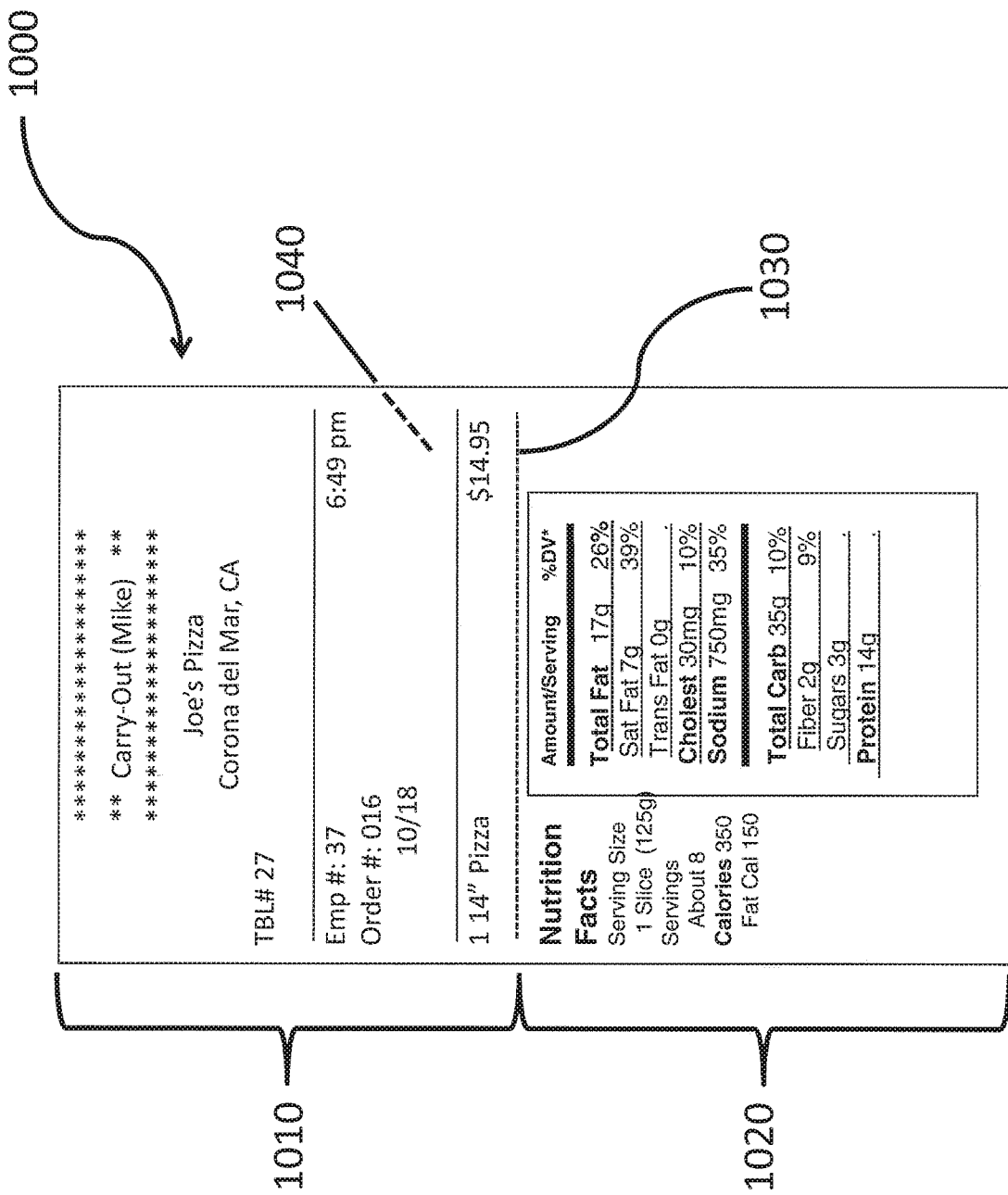
FIG. 10 is an illustrative embodiment of a Nutrition Facts label/receipt of the disclosure.

An example of a receipt/Nutrition Facts label of the present disclosure is illustrated in FIG. 10. In this aspect, the receipt may display conventionally available information such as date, price, quantity purchased, server, etc., but may also display, based on the dispensed quantity of product, one or more product attributes such as calories, grams of fat, etc. In a highly preferred aspect, illustrated in FIG. 10, such information may be displayed in the form of a Nutrition Facts label as part of a receipt, creating a receipt/label combination, generally 1000, that may be printed out at check out, for example at the cash register of a fast food restaurant, or at checkout in a grocery store, or from a dispensing machine, for example, a beverage dispensing machine such as the Freestyle® dispensing machine currently dispensing products of The Coca-Cola Company. While the printing apparatus used to print out a receipt or a Nutrition Facts label may be conventional, and are generally known, receipt/label combinations such as those illustrated in FIG. 10 and described herein are not conventional, nor is the method by which they are produced and used believed to be known, particularly for customized food and beverage products provided at self-service outlets.

As illustrated, the receipt/label combination 1000 may comprise an information-bearing receipt portion 1010 onto which various purchase-specific information may be provided, including store name, customer name, date, server, price, type of product, etc. But the receipt/label combination 1000 may also be provided with product-specific information not currently available for products such as food and beverage products purchased for immediate consumption, and may include a Nutrition Facts portion 1020 as illustrated. Such product specific information preferably comprises one or more ingredient attributes, such as total calories contained in the dispensed product or, in the case of a product that is not dispensed, such as a hand served product like pizza, calories per serving.

While a Nutrition Facts portion 1020 for only one serving of one food item, in this example, a single slice of a 14-inch cheese pizza such as currently available from Pizza Hut is shown, it will now be readily understood that the system of the present disclosure can be employed to include any number of food items, any portion size, for example, an entire pizza, and the ingredient attributes associated with each. This may be achieved by listing the food and beverage or other products as is currently done on conventional receipts at restaurants, supermarkets, big box stores, etc., on the receipt/label combination 1000 in the receipt bearing portion, and then listing all of the nutrition facts associated with each food or beverage product in a separate section, as schematically illustrated by broken line 1030. This broken line 1030 may merely be a printed line (which need not be broken), or may represent a perforation, or may represent a score line.

In a preferred aspect, the receipt/label combination 1000 may comprise on the reverse, i.e., non-information-bearing side, a peel-off backing layer, 1040. Such peel-off backing layer may be applied to the entirety of the receipt/label combination 1000, or may advantageously be applied to only that portion of the receipt/label combination 1000 that is desired to include an adhesive coating or layer enabling the receipt portion 1010, the Nutrition Facts portion 1020, or both, to be peeled from the peel-off backing layer 1040 and applied to a container for the relevant food or beverage product, such as a pizza box, beverage cup, etc. In this aspect, the receipt/label combination 1000 may comprise a peel-off backing and adhesive coating or layer substantially the same as used for printing out baggage tags and baggage claim receipts for airline customers.

It will now be appreciated that the Nutrition Facts portion 1020 of the receipt/label combination 1000 may be printed upon completion of a product dispensing operation by correlating the quantity of product dispensed or served to the quantity of relevant product attributes associated with such quantity of product, i.e., 240 calories per 12-ounce serving of a dispensed beverage, 300 calories per serving of pizza, etc. In the case of a non-dispensed product, i.e., a pizza, the cash register, printer, or other device configured to record the transaction may comprise or have access to a lookup table comparable to those employed online, i.e., on websites of food product sellers, such as Pizza Hut, to disclose product attributes for their products. The system may be configured to parse the online Nutrition Facts data or information into a form that complies with FDA Nutrition Facts label requirements. The system may further comprise a point-of-sale touch screen, which may comprise icons as is known, to permit a crew worker to select the product being purchased, which may now permit recording not only the transaction but also the product attributes attributed to the product being purchased, which information may then be transmitted to a printer or other device configured to display the information on a receipt/label combination 1000 such as disclosed herein.

Figure 11:
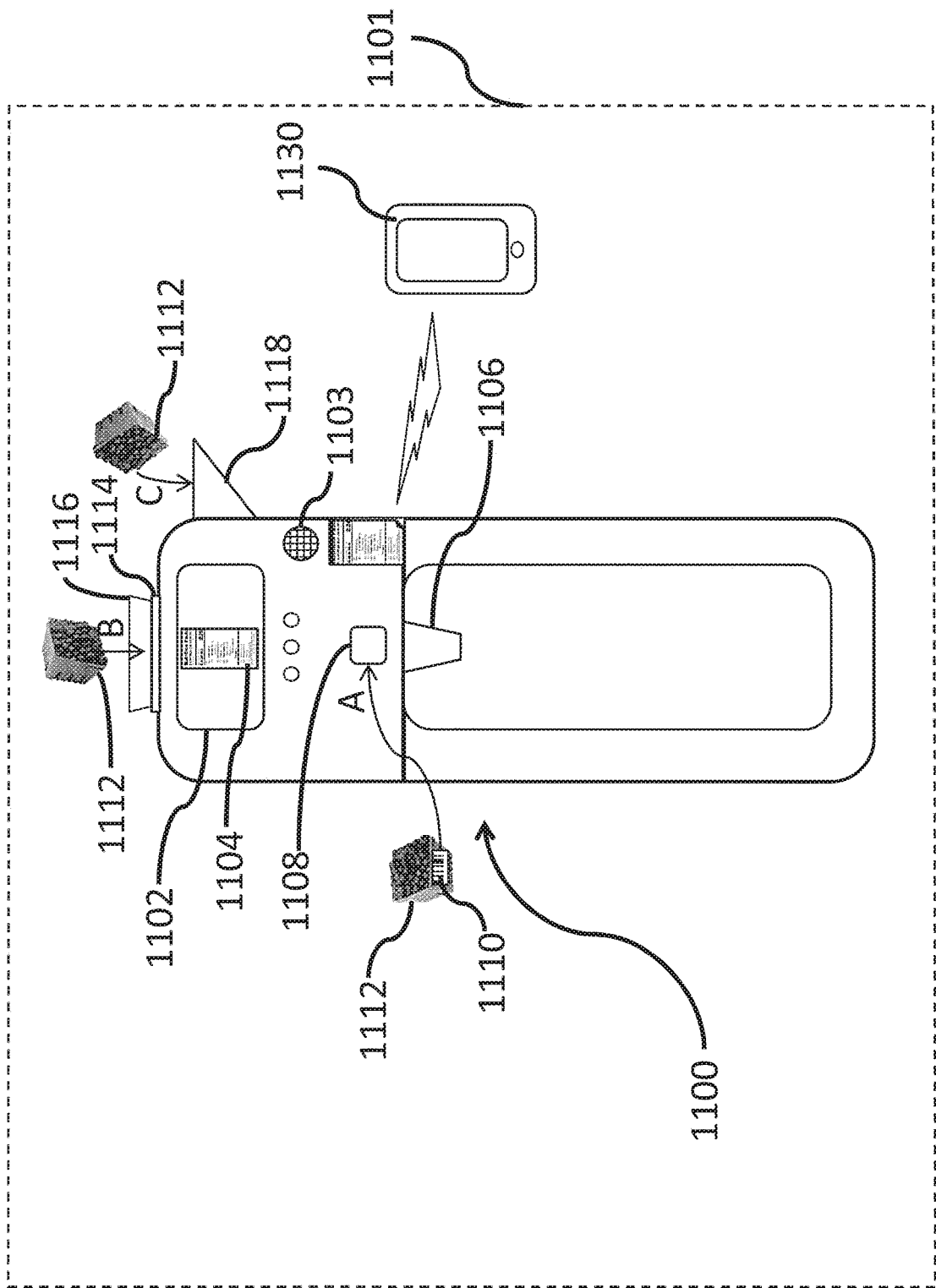
FIG. 11 is an illustrative embodiment of a food or beverage product dispenser of the disclosure.

Another aspect of the disclosure is illustrated in FIG. 11. Because of the waning popularity of sugary soft drinks, beverage manufacturers have begun experimenting with at-home, make-your-own beverages, such as those available, for example through SodaStream dispensers, with which PepsiCo has recently announced plans to conduct market tests. But because of the well-known consequences of consuming excess sugar, fat, salt, calories, etc., and recommendations from, inter alia, the CDC that Americans consume more fruits and vegetables, many health-conscious consumers have resorted to blending their own smoothies, vegetable and fruit juices, etc., at home, or purchasing such customized blended beverages at health food stores and restaurants. Such consumers may also utilize smartphone apps such as "Lose-it" or "Fooducate" to assist them in counting calories and/or other product attributes. These apps may comprise a bar code scanning feature that may permit a consumer to quickly and conveniently determine the Nutrition Facts associated with a packaged food product containing a bar code or other device for scanning.

While such apps are useful for consumers while consuming a single, packaged food or beverage product, they are not currently enabled to readily permit a consumer to determine calorie count or nutrition facts for a customized food or beverage product, such as may be prepared at home using a blender or at a restaurant that prepares made-to-order products such as smoothies. Thus, whether consumers mix their own beverages, smoothies, etc. at home, or purchase them at restaurants, such customized blends do not readily permit the consumer to know the Nutrition Facts or other ingredient attributes of the resulting product.

Custom made beverages are becoming increasingly popular as consumers come to realize that packaged beverages, even those labeled as "natural," or even "100% juice" may contain unwanted ingredients, GMO's, high amounts of sugar, etc. Store bought juice, for example may not be as "wholesome" as consumers are lead to believe. As explained by the Florida Department of Citrus, juices, including 100% juice products and juices labeled as not from concentrate, can have "flavor packs" added. When oranges are processed, natural components such as orange aroma, orange oil from the peel, and pulp may be separated from the orange juice. After the juice is pasteurized, these natural orange components may be added back to the orange juice for optimal flavor. Some juices are stored for a year before they are re-flavored, shipped out, then sold at the supermarket. Thus, "100% juice," and "not from concentrate" does not always mean fresh.

And "natural" when used on food or beverage packaged product labels does not always mean natural. The FDA currently does not define the term "natural." An FDA nonbinding advisory opinion states that "natural" means "nothing artificial or synthetic (including colors regardless of source)" or anything in the product that "would not normally be there." But this nonbinding advisory opinion cannot be legally enforced. This phenomenon leads to misleading labeling, for example, "Crystal Light Natural Lemonade," which has artificial color and no lemon in its ingredients.

An aspect of the disclosure illustrated schematically in FIG. 11 may address one or more of these shortcomings. As illustrated, a product dispenser, generally 1100, may comprise a known dispenser, such as a Freestyle® dispensing machine of The Coca-Cola Company, a Spire dispensing machine of PepsiCo, Inc., a SodaStream®-type dispensing machine, a Keurig®-type dispensing machine, blender, or any other food or beverage processor or dispenser modified or configured as disclosed herein. Such a product dispenser 1100 may comprise a display 1102, configured, for example, to display product specific information such as a virtual Nutrition Facts label 1104, either in real time during a dispensing operation of a product through a dispensing outlet 1106, such as a nozzle, or tap, and/or at the conclusion of a dispensing operation, such as described in co-pending U.S. patent application Ser. No. 14/335,855, entitled SYSTEM, METHOD, AND APPARATUS FOR PURCHASING, DISPENSING, OR SAMPLING OF PRODUCTS, filed Jul. 18, 2014.

The product dispenser 1100 may also comprise an input device 1108, which may be, for example, a bar code scanner, a manual input, a graphical user interface, a receiver, an RFID reader, a food product recognition module, a magnetic strip reader or any other input device configured to receive product-specific information pertaining to a food or beverage product. In one aspect, the input device 1108 may comprise a bar code scanner configured to receive information from a product bar code 1110, in this example, associated with a package of blueberries 1112. Such bar code scanner may, for example, be configured substantially the same as devices and apps associated with smart phones such as the Apple iPhone 5 for scanning bar codes, such as the "Fooducate" app.

Alternatively or additionally, the input device 1108 may be a receiver configured to receive information, for example, from a product bar code 1110 that is scanned using a handheld device 1130, such as a smart phone that may wirelessly transmit the information to the input device 1108 of the product dispenser 1100. Such a configuration, which may also comprise a mobile device or handheld device 1130, 1230 used in connection with a food or beverage product dispenser 1100 of FIG. 11 or a food processor or blender, generally 1200 of FIG. 12, may be particularly suited for a self-serve scenario, and/or a home use situation for the food or beverage product dispenser 1100 or food processor or blender 1200. Such a mobile device or handheld device 1130, 1230 may, in combination with a food or beverage product dispenser 1100 or a food processor or blender 1200, avoid the need for a dedicated input device 1108 or scanner 1212, as the mobile device or handheld device 1130, 1230 may comprise an input device and/or scanner and communicate inputted or scanned information wirelessly to the food or beverage product dispenser 1100 or food processor or blender 1200. Alternatively, the mobile devices or handheld devices 1130, 1230 may comprise or be in communication with other mobile devices including wearable devices such as Google Glass, the Apple iWatch, or similar devices capable of recognizing, for example, a bar code, processing the data therefrom, and/or transmitting or displaying such information for further processing or use.

Figure 12:
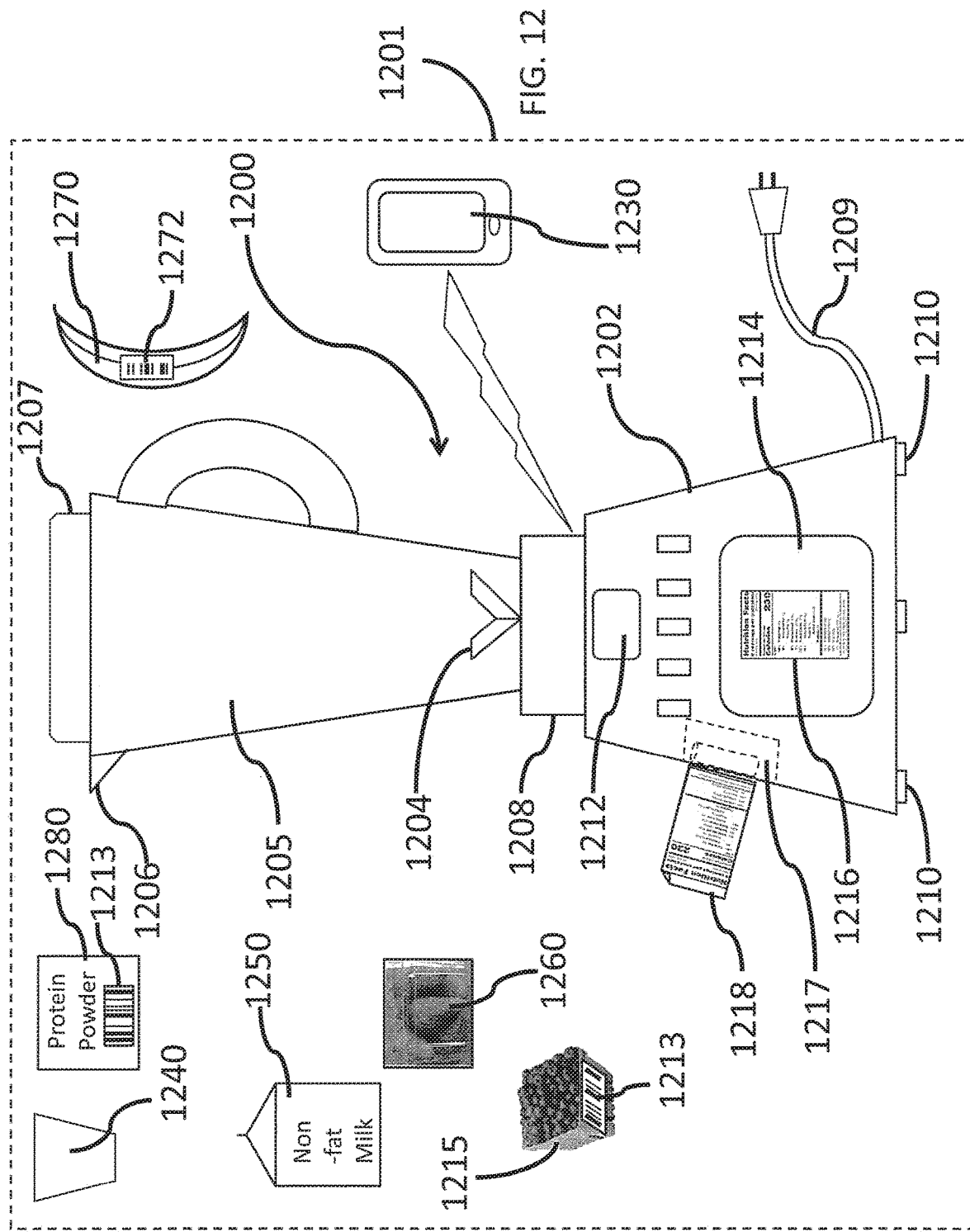
FIG. 12 is an illustrative embodiment of a food processor or blender of the present disclosure and a system illustrative of use thereof.

In a preferred aspect, a system such as system 1101 of FIG. 11 or 1201 of FIG. 12 may comprise a food or beverage dispenser 1100 or food processor or blender 1200 configured to communicate with a remote, mobile, or handheld device 1130, 1230 of a user, for example, with via wireless connection, and to upload Nutrition Facts for a resulting food or beverage product for immediate consumption prepared by the food or beverage dispenser 1100 or food processor or blender 1200 to the remote, mobile, or handheld device 1130, 1230. The remote, mobile, or handheld device 1130, 1230 may comprise a smart phone, a wearable device, i.e., Google Glass or Apple iWatch, a smart pad, a laptop, etc. The food or beverage dispenser 1100 or food processor or blender 1200 may be configured to upload to the remote, mobile, or handheld device 1130, 1230 calorie count data for the resulting food or beverage product for immediate consumption to a calorie counting app, such as "Fooducate" or "Lose-It!" of the user of the remote, mobile, or handheld device 1130, 1230. In this aspect, a user of, for example, a food processor or blender 1200 may have a calorie count or other Nutrition Facts for a blended food or beverage product for immediate consumption uploaded to the user's calorie counting app, which uploading may be achieved wirelessly and/or automatically, for example, once the food processor or blender 1200 is cued, for example, by the user pressing a "stop" button, that the blending operation is complete, or when the food processor or blender 1200 senses, for example, via the weighing mechanism 1210 (subsequently described) that the blender container 1205 has been removed from the food processor or blender 1200. Similar uploading, with respect to the food or beverage dispenser 1100 may commence upon the food or beverage dispenser sensing that a dispensing operation has concluded, for example, by sensing that a "pour" button or lever has been released.

As an alternative to a bar code scanner, RFID reader, magnetic strip reader, etc., and of particular use with food products not containing a readable code, chip, or strip, the input device 1108 may comprise a manual input, such as a touch screen configured to permit a user to input the name of food product being processed, such as a banana. The input device 1108 and/or product dispenser 1100 may further be configured with a database that comprises ingredient attributes for the food type thus inputted, and configured to include such information for further use as described herein. In this example, the database may comprise information such as Nutrition Facts for a cup of mashed banana, about one cup, comprising, e.g., 200 calories, 28 grams of sugar, 6 grams of fiber, 2 grams of protein, 33% of the recommended daily value of vitamin C, etc. The input device 1108 may be integral with the product dispenser 1100 as illustrated, and/or may be associated with a mobile device of a user communicatively coupled to the food or beverage dispenser 1100.

As another example, the input device 1108 may comprise a food product recognition module. As used herein, "food product recognition module" means a system configured to scan, photograph, or otherwise image a food product and compare the resulting image to a database of known food products to identify the imaged food product and access an ingredient attribute database as described in the banana example above. A food product recognition module may thus be similar to known facial recognition systems and related software, modified to recognize and identify foods rather than faces. Such a food product recognition module may, for example, comprise an app such as Blippar, subsequently described. Once the food product is identified, the user may be prompted to confirm that the proper identification has occurred.

In a preferred method of the disclosure, a consumer, in the case of an in-home product dispenser 1100, or a restaurant server or barista, food store or supermarket server, or fast food crew server, in the case of a commercial food or beverage dispenser 1100, may input food or beverage specific data, as illustrated by arrow "A," by, for example, scanning a bar code 1110 associated with a product, such as the package of "Nature's Partner" blueberries 1112, on the input device 1108, in this case a bar code scanner. The dispenser may be configured in the same manner as a smartphone, for example, with an app such as "Lose It," "Shop Well," or "Fooducate" to receive from a bar code associated with a food or beverage product product-specific information, including Nutrition Facts, ingredient attributes, whether or not the ingredient is truly "natural," etc., and record, process, and/or transmit such information as will be subsequently described, and optionally display such information on the display 1102. This information, in the case of the afore-mentioned blueberries, may include and/or appear on the display 1102 as in the following example:

Example 2

| Blueberries serving size: 1 cup (148 g) 84 Calories per serving All natural | | |
|---|---|---|
| | Amount per Serving | My Daily Value |
| Calories | 84K cal | 3% |
| Calories from fat | 0K cal | 0% |
| Total Fat | 0 g | 0% |
| Sat. Fat | 0 g | 0% |
| Trans Fat | 0 g | 0% |
| Cholesterol | 0 mg | 0% |
| Sodium | 5 mg | 0% |
| Total Carbohydrate | 17 g | 4% |
| Dietary Fiber | 4 g | 13% |
| Sugars | 15 g | 8% |
| Protein | 1 g | 1% |
| Vitamin A | 80 IU | 2% |
| Vitamin C | 14 mg | 16% |
| Calcium | 9 mg | 1% |
| Iron | 0 mg | 0% |

Some or all of the above-referenced Nutrition Facts or product-specific information, which may also or alternatively comprise "ingredient attribute" information as used herein, may be recorded, stored, transmitted and/or used by the dispenser 1100 to query or instruct the user to verify that the input device 1108 correctly identified the food or beverage product, and/or to determine the quantity of food or beverage product to process in the dispenser 1100. After the food or beverage product has been scanned or otherwise inputted, the display 1102, or an audible message played through a speaker 1103, may be configured to display a visual message or play an audible message, such as "place the desired amount of scanned product in the weighing bin." The dispenser 1100 may comprise, communicate with, or be associated with, a weighing apparatus 1114, such as a scale or balance similar to those used, for example, at supermarket deli counters. Another audible message, for example, "now weighing the blueberries you have added," may be played after a scanned and determined product, in this case blueberries, have been added to the weighing apparatus 1114.

The user may be prompted, after scanning the bar code 1110, (or otherwise entering product-specific data into the dispenser 1100) to place any desired quantity of the scanned item, such as blueberries 1112, on or in the weighing apparatus 1114. As will be appreciated, the weighing apparatus may comprise a bin, pan or tray 1116 into which the item may be poured or placed for weighing, as illustrated by arrow B. Such bin, pan, or tray 1116 may be removable, to permit the weighed item to be poured back into its original container or into the dispenser 1100. The dispenser 1100 may also be configured to query a user, in response to sensing that a food or beverage product has been added to the weighing bin but has not been scanned, if the user has forgotten to scan the item. In the case of added water or ice, the consumer may be prompted to indicate "no." In the case of a food or beverage product other than water or ice, the consumer may be prompted to scan or enter the identity of the added food or beverage product that had not been scanned prior to being deposited in the weighing apparatus 1114.

Once the food or beverage item, such as blueberries 1112 are weighed by the weighing apparatus 1114, the display 1102, which may, as a display on a scale common to supermarket deli counters, display the quantity in weight of the product being weighed. But different from conventional scales, the weighing apparatus 1114 of the present disclosure may be configured to determine, based on the quantity of food or beverage product placed therein or thereon, one or more ingredient attributes or Nutrition Facts, based on the scanned or inputted product attribute information, as illustrated in Example 3.

Example 3

Two cups of blueberries of Example 2 are poured into the weighing bin 1116. The dispenser 1100, having previously recorded the scanned information of Example 2, is configured to determine, based on the amount of product placed in the weighing apparatus 1114, the total Nutrition Facts, ingredient attributes, and/or other product-specific information specific to the quantity of product placed in the weighing bin 1116. In this example, as 2 cups, or 296 grams of blueberries are weighed in the weighing bin 1116, the dispenser determines two servings have been placed in the weighing bin 1116 and determines to double the recorded values to account for two servings having been placed in the weighing bin 1116, as follows:

|  | Amount per Serving | My Daily Value |
| --- | --- | --- |
| Calories | 168K cal | 6% |
| Calories from fat | 0K cal | 0% |
| Total Fat | 0 g | 0% |
| Sat. Fat | 0 g | 0% |
| Trans Fat | 0 g | 0% |
| Cholesterol | 0 mg | 0% |
| Sodium | 10 mg | 0% |
| Total Carbohydrate | 34 g | 8% |
| Dietary Fiber | 8 g | 26% |
| Sugars | 30 g | 16% |
| Protein | 2 g | 2% |
| Vitamin A | 160 IU | 4% |
| Vitamin C | 28 mg | 32% |
| Calcium | 18 mg | 2% |
| Iron | 0 mg | 0% |

It will now be readily appreciated that at this point, additional food or beverage products (not shown) may be scanned (or product-specific information otherwise entered via the input device 1108 into the dispenser 1100) and poured into the weighing bin 1116. The dispenser 1100 may thus be configured to determine, in serial fashion, the Nutrition Facts and/or ingredient attributes for every scanned product, and sum the resulting values determined based on the quantity of product added to the previously scanned, weighed, and recorded food or beverage product(s).

After one or more food or beverage products are thus scanned, weighed, and product attribute(s) recorded, and it is determined that no additional products will be added, the food or beverage products may be further processed, for example, by pouring the total contents of the weighing bin 1116 into a food processing chute 1118, as illustrated by arrow "C" in FIG. 11. Such food processing chute 1118 is schematic only, and may of course take other structural forms, including, for example, a blender pitcher. At this point, the food or beverage product or product mixture may be processed, mixed, or blended within the dispenser 1100 to create a flowable or semi-flowable dispensed product that may be dispensed via the dispensing outlet 1106. And, the Nutrition Facts and/or ingredient attributes associated with such dispensed product may be indicated on the dispenser display 1102, for example, in real time, and/or at the conclusion of the dispensing operation. Additionally or alternatively, the dispenser 1100 may, upon conclusion of the dispensing operation dispense a label 1104 as described herein, which label 1104 may comprise a Nutrition Facts label, a receipt, a combined Nutrition Facts label/receipt, and/or one or more ingredient attribute indicators, such as those configured to indicate, for example, the amount of calories, sugar, etc., contained within a container at the fill line and/or the amount thereof remaining in the container at one or more post consumption fill lines.

The weighing apparatus 1114 may comprise a weighing scale such as those used at supermarket deli or checkout counters. A commercially available example of such scales includes The StoreLIVE! Point of Sale system, which supports direct attached scales for weighing product at the point of purchase, as well as the functionality to scan variable weight barcodes produced by label printing scales. In addition to the point of sale features, product information such as pricing and ingredients can be transmitted from the StoreLIVE! database to supported networked scales. The StoreLIVE! system contains fields such as PLU, ingredients, and scale item description in addition to the normal item attributes such as price. This feature allows the StoreLIVE! system to serve as the master database for scale product information. Via integration with Invatron System Corp Plum Store product, this information can seamlessly be transmitted to a wide variety of networked scales, including those from Hobart, Metier Toledo and Avery Berkel.

Another example includes a weighing scale sold by Progressive Scale and Software Solutions, 6 Wine Sap Run Bethel Conn. 06801, for example as the Model UAS4000 Programmable Counting Scale System. Another example includes CAS CL-5000J Barcode Label Printing Scale, available from CAS Scales Ltd., New Zealand. Such systems may include a printer for printing a label according to preprogrammed inputs. Such exemplary scale systems may comprise, for example, "Create-a-Label" Windows software and Zebra/Eltron label printers, permitting multiple label formats—now including those as disclosed herein—to be designed. As will now be appreciated, these types of weighing and label printing systems may now be employed to operate in concert with product dispensers, such as product dispenser 1100.

Still another example of a commercially available weighing scale that may be employed and modified as set forth herein includes the EatSmart™ Nutrition Pro Scale—Digital Food and Nutrient Calculator available from HealthTools LLC, Mahwah, N.J. The EatSmart Nutrition Scale analyzes the nutritional content of any food (labeled and unlabeled) by portion size. The database stores the nutritional values for approximately 1,000 foods. This scale reportedly calculates calories, carbs, fiber, sodium, fats, vitamin K and six other nutrients, and includes a tare feature to permit subtracting the weight of a container or plate.

It will now be readily appreciated that the system, methods, and apparatus described herein may be used in combination with existing dispensing equipment as configured according to the teachings herein. In this aspect, using as an example a SodaStream® or Keurig® dispenser, such dispenser may be retrofitted with the systems and apparatus of the present disclosure to permit a consumer, for example, to employ a prepackaged beverage pod, such as a diet cola flavored pod, to dispense a beverage to which has been added a consumer-selected ingredient such as freshly blended blueberry juice using the teachings set forth herein to determine the total Nutrition Facts and/or ingredient attributes specific to the resulting blend. In this aspect, each of the prepackaged pods may be configured with a bar code or other machine readable or scannable code in order to permit the dispenser 1100 to determine the Nutrition Facts and/or ingredient facts attributable to the prepackaged pod and sum the same with any consumer added ingredients such as blueberries. In this way, consumers may be offered greater choice, for example, to flavor homemade food and beverage products with natural, as opposed to artificial, ingredients.

Another aspect of the disclosure is illustrated in FIG. 12. In this aspect, a food processor or blender, generally 1200, may be modified as disclosed herein. The food processor 1200 may comprise standard components, such as a motorized housing 1202, with a motor (not shown) that engages a rotor blade 1204 that processes food and/or beverages within a blending container 1205 such as a pitcher with a spout 1206 and removable lid 1207. The food processor or blender 1200 may be cordless, i.e., battery powered, or may be powered via a plug-in electrical cord 1209. The blending container 1205 may include a bayonet type mount 1208 configured to enable the container to be removeably and securely mounted to the motorized housing 1202 as is known. Instead of a blending container 1205 comprising a handled pitcher with spout, the blending container 1205 may comprise a container intended for producing a single serve blended food or beverage product for immediate consumption. The food processor or blender 1200 may comprise speed control knobs or buttons, an on-off switch, etc. Examples of food processors or blenders that may be modified as disclosed herein include those described in U.S. Patent Application Publication No. US 2014/0286123 A1, incorporated in its entirety by reference herein, the "Vitamix" line of blenders, sold by Vita-Mix Corporation, 8615 Usher Road Cleveland, Ohio 44138 USA, or the "Nutri Ninja" line of blenders.

The food processor or blender 1200 of the present disclosure may be configured with a weighing mechanism 1210, such as previously described, or comprising one or more pressure sensors, for example, similar or identical to the "High Precision EatSmart Sensors" employed on the EatSmart Precision Digital Bathroom Scale, available from Amazon.com. Such sensors of the weighing mechanism 1210 may, for example, comprise piezoelectric pressure sensors that may convert mechanical pressure in the form of applied weight to voltages, which may be displayed as units of weight, such as pounds or grams. Such sensors are disclosed in U.S. Pat. No. 4,512,431, incorporated in its entirety by reference herein. Other types of known weighing mechanisms are of course possible. For example, the weighing mechanism 1210 may be substantially similar to those used in the Vitamix Portion Blending System® Advance® 2.0, commercially available from Vita-Mix Corporation, 8615 Usher Road, Cleveland, Ohio 44138, which rely on a scale positioned beneath the blender container to apportion known quantities of ice. The weighing mechanism 1210 may be configured to enable the entire weight of the food processor or blender 1200 be tared to zero, such that only the weight of food and/or beverage products placed within the blender container 1205 is measured and processed according to the teachings herein. Similar to the EatSmart Precision Digital Bathroom Scale, the weighing mechanism may automatically switch on in response to weight being placed in the blender container 1205.

The food processor or blender 1200 may further comprise a scanner 1212 configured to scan a bar code or other code associated with a food or beverage product or package or container therefore. Such a scanner 1212 may also comprise an RFID reader or similar device configured to recognize, for example, data embedded in an RFID chip in a cup or package. Such scanner 1212 may be configured to recognize and display, for example on a display 1214, in the same way as the "Fooducate" smartphone app, ingredient attributes such as Nutrition Facts, food ratings, alternatives, Food-Points values, etc. for a scanned food or beverage product intended to be processed or blended in the food processor or blender 1200. In one aspect, such scanner 1212 may cooperate with a database programmed to contain food or beverage product information, or the scanner 1212 may be functionally the same as that available using a smartphone such as an iPhone. In this aspect, the food processor or blender 1200 may comprise a computer system, cellular technology, internet connectivity, or any other known device configured to allow the food processor or blender 1200 to use the scanner 1212 substantially the same as a smartphone can use, for example, the "Fooducate" smartphone app to access information pertaining to scanned food and beverage products.

As will now be described, the food processor or blender 1200 may be further configured to determine, based on the ingredient attributes for each scanned food or beverage product, and the proportion by weight of each scanned and weighed food or beverage product, one or more overall ingredient attributes for the resulting food or beverage product processed or blended by the food processor or blender 1200.

As is known, smartphone dieting and food identification apps such as "Fooducate" display food or beverage ingredient attributes such as a food rating for the food or beverage product after scanning. For example, a Kind® Dark Chocolate Nuts & Sea Salt Bar, upon being scanned using the "Fooducate" app, is given a grade of "B−." But the "Fooducate" app does not provide a method whereby a mixture of different food or beverage products, each having its own ingredient attributes, such as a product rating or grade, can itself be given overall ingredient attributes or an overall grade.

Accordingly, employing a preferred aspect of the present disclosure, an overall ingredient attribute or product grade for a blended food or beverage product may be obtained, for example, by determining overall Nutrition Facts or an overall blended product grade based on the proportion of each individual product and the individual Nutrition Facts or grade for each. The following Example illustrates how this may be done.

Example 4

An apple having a bar code or other product identifier is scanned on a scanner 1212 that communicates with a database or smartphone app such as the "Fooducate" app, associated with a food processor 1200, resulting in a recognition that an apple is given an "A" grade, or a numerical food rating of 100. The apple is cored, sliced, and placed in the blender container 1205, whereupon it is weighed and determined to weigh 100 grams. Next, a pack of blueberries is scanned, resulting in recognition that blueberries are given a "B+" grade, or a numerical food rating of 88. A cup of blueberries are poured into the blender container 1205, whereupon the blueberries are weighed and determined to weigh 100 grams. The food processor is then used to blend the blueberries and apple pieces into a natural fruit beverage. The food processor determines, based on the scanned information, the Nutrition Facts for each of the apple and the blueberries, and because each comprises 50% by weight of the resulting blend, determines that half the total Nutrition Facts of the resulting blend are attributable to each of the apple pieces and the blueberries. The food processor 1200 then calculates the resulting Nutrition Facts for the blended beverage and displays the resulting Nutrition Facts as a virtual label 1216 on the display 1214.

Alternatively or additionally, the food processor or blender 1200 may comprise a printer 1217 configured to print out the Nutrition Facts specific to the resulting blended product as a label 1218. The printer 1217 may be conventional, for example, a receipt-type printer having its own motorized compartment, paper roll, ink cartridges, etc., such as commonly used at checkout counters and aisles or deli counters, but modified to print out Nutrition Facts labels specific to customized blends or self-service food or beverage products as set forth herein. Alternatively, printer 1217 may be configured to use the same motor that drives the rotor blade 1204 to drive the printer 1217, as the printing operation may typically occur after the blending operation has concluded. This may be accomplished using a motor with or connected to dual drive shafts, one for engaging the rotor blade and the other for engaging the printer drive, with appropriate gearing for each drive shaft, and appropriate motor speed control for each of the blending and printing operations.

The label 1218 may comprise a combined Nutrition Facts label and receipt combination as previously described. The food processor or blender 1200 may determine the overall food grade of the resulting blended beverage, for example, determining that 50% of a "B+" and 50% of an "A" by weight averages out to an overall food grade of an "A–". Alternatively, the food processor or blender 1200 may determine that an overall numerical food rating by multiplying 50% of 100, 50% of 88, and summing the result, 50+44, to arrive at an overall numerical food rating of 94.

While the weighing mechanism 1210, scanner 1212, display 1214 and printer 1217 or other mechanism for printing or preparing the label 1218 are illustrated in FIG. 12 as comprising a unitary blender 1200, it will be readily appreciated that one or more of such components may be configured separately from the food processor or blender 1200 and connected to the food processor or blender 1200 via wired or wireless connections. Thus, for example, the food processor or blender 1200 may be configured to communicate Nutrition Facts data wirelessly to a remote display and/or a remote printer. A user's mobile device may be configured to provide inputs to the blender 1200. While the weighing mechanism 1210, scanner 1212, display 1214, and printer or other label preparing mechanism 1217 may be separately powered, each may be powered by a single power source.

The dispenser 1100 and/or food processor or blender 1200 may also be configured to query a user, in response to sensing that a food or beverage product has been added to the weighing bin but has not been scanned, if the user has forgotten to scan the item. In the case of added water or ice, the consumer may be prompted to indicate "no." In the case of a food or beverage product other than water or ice, the consumer may be prompted to scan or enter the identity of the added food or beverage product.

Figure 13:
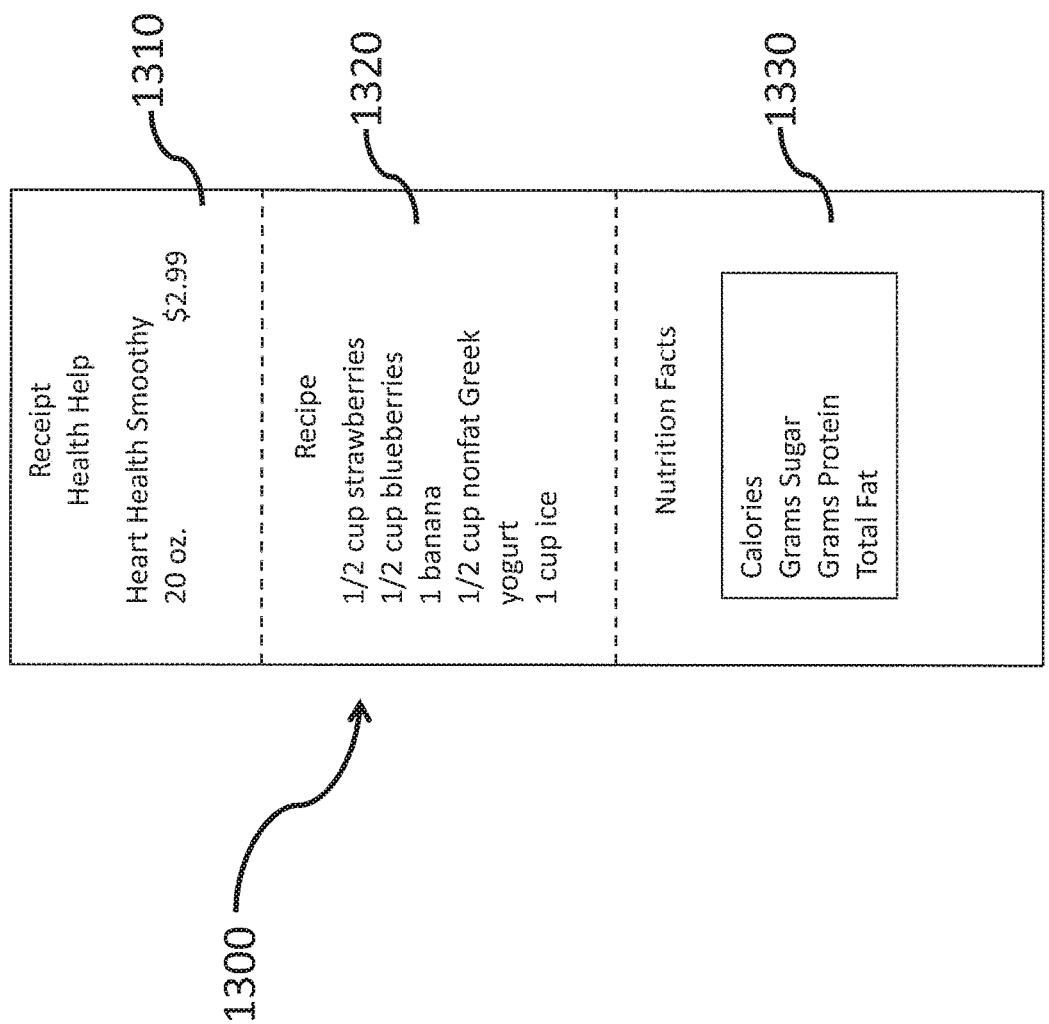
FIG. 13 is an illustrative embodiment of a Nutrition Facts label/receipt/recipe of the disclosure.

In another aspect, the food or beverage dispenser 1100 and/or food processor or blender 1200 may comprise a database configured to record a recipe for the blended food or beverage for immediate consumption. Thus, because the user may scan food or beverage products prior to mixing or blending them in the dispenser 1100 and/or food processor or blender 1200, such a database may keep a running total of the ingredients being mixed or blended and the proportion of each, and record the same as a recipe that may be stored and/or printed out for future use, as illustrated in FIG. 13. As illustrated there, such a printout, generally 1300 may be merely a recipe, 1310, a receipt, 1320, and/or a Nutrition Facts label 1330, the Nutrition Facts being omitted for convenience.

In another aspect, illustrated in FIG. 12, the food or beverage dispenser 1100 and/or food processor or blender 1200 may comprise a system 1201 that accepts coded and pre-weighed ingredients such that a discrete weighing mechanism 1210 is not required, rather, the scanner 1212 and machine readable indicia 1213, i.e., a bar code, RFID, magnetic strip, etc., associated with an ingredient 1215, i.e., prepackaged blueberries, may determine both the Nutrition Facts for the ingredient and the weight thereof, for further processing according to the teachings herein. Thus, the scanner 1212 and machine readable indicia 1213 may effectively replace the discrete weighing mechanism 1210 and act as a substitute therefore. In this aspect, for example, the machine readable indicia 1213 associated with a prepackaged food or beverage product such as ingredient 1215 comprising a pack of blueberries, may be coded with the Nutrition Facts for such ingredient 1215 as well as the net weight thereof, for example, 100 grams, and/or net volume thereof, such as one cup. An outlet preparing blended foods, such as smoothies, may be stocked with multiple pre-weighed and/or pre-measured ingredients, i.e., one cup of plain non-fat yogurt 1240, one cup of non-fat milk 1250, 250 grams of packaged strawberries 1260, etc., each of which may be coded with machine readable indicia 1213 that may be scanned by the scanner in order to process the Nutrition Facts information for each ingredient, apportion such Nutrition Facts according to the portion of a resulting food or beverage product for immediate consumption, and display a resulting Nutrition Facts label 1216, 1218, for the resulting food or beverage product for immediate consumption.

In another aspect of the system 1201, other ingredients that may not be packaged, i.e., whole fresh fruits or vegetables, such as a banana 1270, may likewise have machine readable indicia 1213 associated therewith, such as a bar coded sticker 1272. Produce, such as apples, oranges, bananas, etc., are conventionally coded with bar coded stickers that identify the produce and/or provide pricing information for pricing the produce at checkout. According to the teachings herein, such bar coded stickers 1272 may now be coded with one or more of Nutrition Facts, net weight, typical weight, etc. for such non-packaged ingredients. Alternatively, such whole fresh ingredients may be packaged, for example, in shrink wrap onto which the machine readable indicia 1213 has been applied. In other aspects of the system 1201, prepackaged and coded packets of ingredients 1280, such as protein power, sugar, sugar substitutes such as stevia leaf extract, salt, etc., may be provided. All such ingredients, weather fresh, frozen, packaged, or otherwise, may thus be scanned in order to access ingredient specific information such as Nutrition Facts, net weight, typical weight, etc., for such ingredients. Such ingredient specific information may in some cases be accessed or determined directly from the machine readable indicia 1213, may be accessed or determined via a database associated with the food processor or blender 1200, or may be accessed or determined via a remote database through, for example, an internet connection associated with the food or beverage processor 1200.

The system 1201 may thus be arranged to enable a user of the food or beverage dispenser 1100 or the food processor or blender 1200 to readily access pre-packaged, pre-weighed, coded ingredients that may be mixed and matched to order in an infinite number of recipes and combinations, yet provide Nutrition Facts specific to a particular food or beverage product for immediate consumption produced by the food or beverage dispenser 1100 or food processor or blender 1200. Such Nutrition Facts may, in a preferred aspect, be uploaded, for example, to the user's calorie counting app, such as "Lose-It!" or "Fooducate." The food or beverage dispenser 1100 or food processor or blender 1200 may be configured to communicate with the user's wearable device, handheld device, mobile device, smart phone, laptop, smart pad, etc. and upload such information with or without prompting by the user.

The food or beverage dispenser 1100 or the food processor of blender 1200 may be configured with a "start" button, a "dispense" button, or other signaling device configured to initiate a calculation sequence to determine Nutrition Facts for the resulting food or beverage product for immediate consumption produced by a dispensing, processing, or blending operation. Alternatively, the calculation sequence may initiate automatically upon initiation or conclusion of the dispensing, processing, or blending operation.

Figure 18:
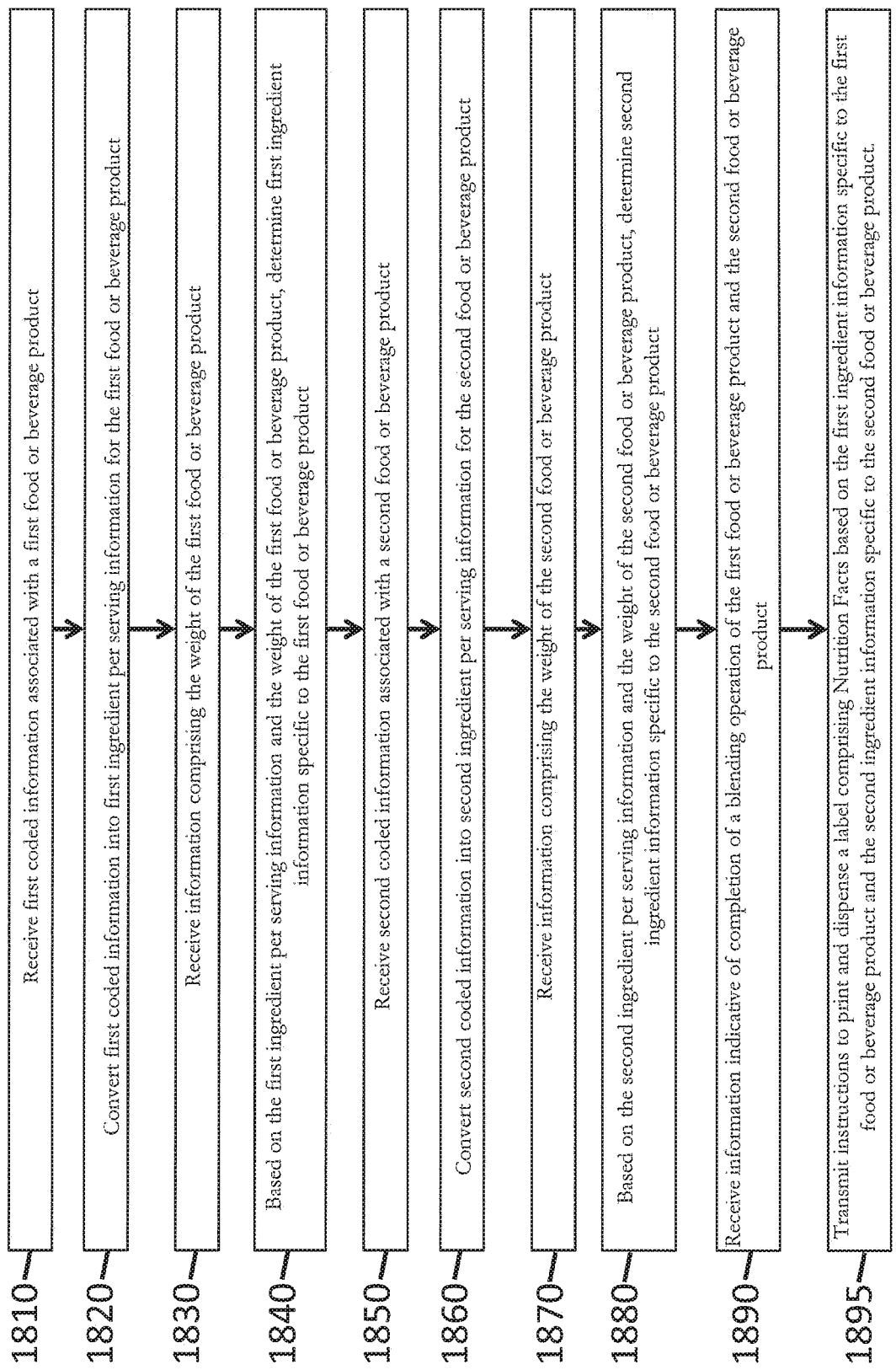
FIG. 18 is an illustrative embodiment of a method of the disclosure, illustrative of using the system of FIG. 7, the food or beverage product dispenser of FIG. 11, the food processor or blender and/or system of FIG. 12, and/or the system of FIG. 14.

One of the methods for using system 1201 of FIG. 12 is illustrated in FIG. 18. According to this method, at operation 1810, first coded information associated with a first food or beverage product may be received, for example via machine readable indicia 1213 scanned by the scanner 1212 responsive to a user scanning the machine readable indicia 1213 thereon.

At operation 1820, the system 1201 may convert the first coded information into, for example, first ingredient per serving information for the first food or beverage product. Such first ingredient per serving information may comprise Nutrition Facts for a standard serving size of the first food or beverage product.

At operation 1830, the system 1201 may receive information comprising the weight of the first food or beverage product. This may be achieved in various ways, including by use of a weighing mechanism to weigh the first food or beverage product, by use of a pre-weighed food or beverage product, wherein the pre-weighed amount is coded on the machine readable indicia 1213, and/or wherein the weight is manually entered into the system 1201, for example, via a user interface associated with the display 1214 or a mobile device associated with the user.

At operation 1840, the system 1201 may, based on the first ingredient per serving information and the weight of the first food or beverage product, determine first ingredient information specific to the first food or beverage product, for example, the Nutrition Facts specific to the particular quantity of food or beverage of interest. This may be accomplished, for example, via a microprocessor, as subsequently described, which may be configured to convert generalized Nutrition Facts data for a particular food or beverage standard serving size, for example, 100 grams, into specific Nutrition Facts for the quantity of the food or beverage of interest, for example, 50 grams, in this example, by halving the generalized Nutrition Facts data. This result may be stored for further processing, i.e., in memory associated with the system 1201.

At operation 1850, the system 1201 may receive second coded information associated with a second food or beverage product. This may be achieved, for example, using substantially the same procedure(s) used at operation 1810, for example, responsive to a user scanning a bar code of a food or beverage product on a scanner associated with the system 1201, the system 1201 may receive information specific to the second food or beverage product.

At operation 1860, the system 1201 may convert the second coded information into second ingredient per serving information for the second food or beverage product, for example, using substantially the same procedure(s) used at operation 1820, except for the second food or beverage product.

At operation 1870, the system 1201 may receive information comprising the weight of the second food or beverage product. This may be achieved using substantially the same procedure(s) used at operation 1830, except for the second food or beverage product.

At operation 1880, based on the second ingredient per serving information and the weight of the second food or beverage product, the system 1201 may determine second ingredient information specific to the second food or beverage product. This may be achieved using substantially the same procedure(s) used at operation 1840, except for the second food or beverage product.

At operation 1890, the system 1201 may receive information indicative of completion of a blending operation of the first food or beverage product and the second food or beverage product, for example, after such products have been deposited in the blender container 1205 and processed to completion of a food or beverage product for immediate consumption. Such information may, for example, comprise the system receiving a signal indicative that a motor associated with the food processor or blender 1200 has been turned off, or information comprising a signal that a "stop" button or other similar command has been activated.

At operation 1895, the system 1201 may transmit instructions to display a label 1216 and/or print a label 1218 comprising Nutrition Facts specific to the resulting blend, based on the first ingredient information specific to the first food or beverage product and the second ingredient information specific to the second food or beverage product.

Of course this method is exemplary only, and in no way exclusive of other similar methods that may be employed using the teachings herein. For example, more or fewer than two food or beverage products may be used. Water and/or ice may be added. The system 1201 may be used, particularly in commercial establishments, to blend more than one serving at a time in a single operation, and print out multiple Nutrition Facts labels specific to each serving.

Figure 14:
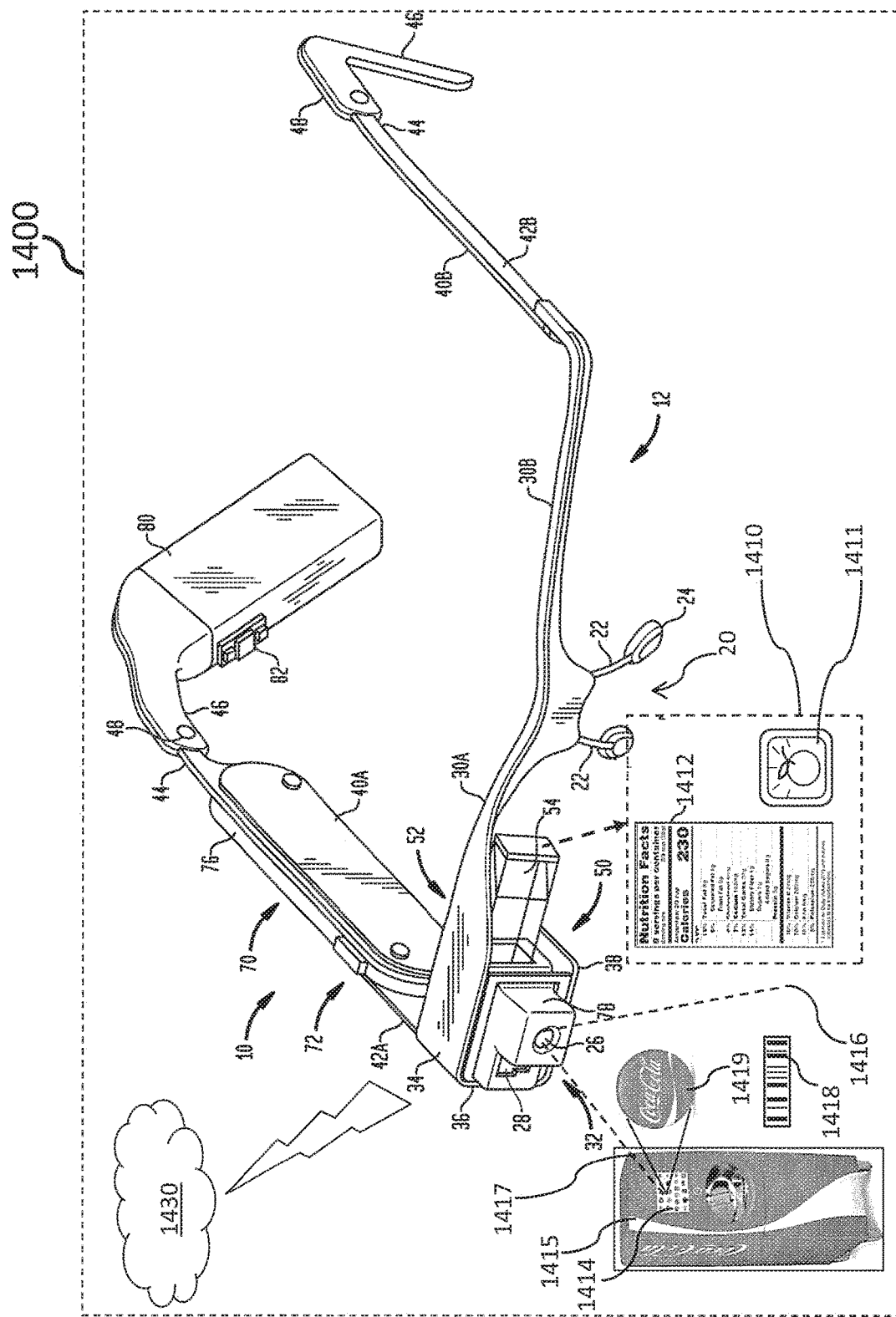
FIG. 14 is an illustrative embodiment of a wearable device of the disclosure and a system illustrative of the use thereof with a food or beverage product dispenser.

Another aspect of the disclosure is a system as illustrated in FIG. 14. In this aspect, a user may be associated with a mobile device comprising a "wearable device," such as disclosed in U.S. Patent Publication No. US 2013/0044042 A1 published Feb. 21, 2013 and assigned to Google Inc., incorporated in its entirety by reference herein, such as disclosed in U.S. Pat. No. 8,787,006, assigned to Apple, Inc., incorporated in its entirety by reference herein, such as Application Number PCT/US2012/000560, published May 30, 2013, assigned to Magic Leap, Inc., incorporated in its entirety by reference herein, or such as commercially available or soon to be available devices like Google "Glass," the Apple "iWatch," the Facebook "Occulus VR" or the "Magic Leap" head-mounted virtual reality device. Such devices may be wearable computing devices configured for receiving, transmitting, and displaying data and/or for communicating with other devices such as a smart phone, a beverage dispenser, etc. As is known, such wearable devices may comprise one or more of an on-board computing system, a video camera, a sensor, and a finger-operable touch pad. The on-board computing system may include a processor and memory, for example. The on-board computing system may be configured to receive and analyze data from the video camera and/or the finger-operable touch pad (and possibly from other sensory devices, user interfaces, or both) and generate images for output by lens elements. The video camera may be configured to capture images at various resolutions or at different frame rates. Many video cameras with a small form-factor, such as those used in cell phones or webcams, for example, may be incorporated into the wearable device. The sensor may include one or more of a gyroscope or an accelerometer, for example. Other sensing devices may be included within, or in addition to, the sensor or other sensing functions may be performed by the sensor, such as motion sensing, level sensing, etc. The wearable device may further be configured to receive and respond to voice actuated commands, such as Siri-type commands and information retrieval available, for example, via the Apple iPhone smart phone or iPad tablet. Indeed, smart phones, tablets, or other portable devices may be equipped substantially as the wearable devices discussed herein to achieve similar functionality, albeit perhaps with less convenience.

The finger-operable touch pad may be used by a user to input commands. The finger-operable touch pad may sense at least one of a position and a movement of a finger via capacitive sensing, resistance sensing, or a surface acoustic wave process, among other possibilities. The finger-operable touch pad may be capable of sensing finger movement in a direction parallel or planar to the pad surface, in a direction normal to the pad surface, or both, and may also be capable of sensing a level of pressure applied to the pad surface. The finger-operable touch pad may be formed of one or more translucent or transparent insulating layers and one or more translucent or transparent conducting layers. Edges of the finger-operable touch pad may be formed to have a raised, indented, or roughened surface, so as to provide tactile feedback to a user when the user's finger reaches the edge, or other area, of the finger-operable touch pad. If more than one finger-operable touch pad is present, each finger-operable touch pad may be operated independently, and may provide a different function.

Lens elements of the wearable device may act as display elements. The head-mounted device may include a first projector coupled to an inside surface of an extending side-arm and configured to project a display onto an inside surface of the lens element. Additionally or alternatively, a second projector may be coupled to an inside surface of the extending side-arm and configured to project a display onto an inside surface of the lens element. The lens elements may act as a combiner in a light projection system and may include a coating that reflects the light projected onto them from the projectors. In some embodiments, a reflective coating may not be used (e.g., when the projectors are scanning laser devices). In other embodiments, a light projection system may project an image through a prism or other light redirecting or focusing apparatus directly onto the user's retina.

FIG. 14 illustrates an embodiment of a wearable device 10 that is configured to be worn on the head of a user with a display 50 thereof positioned adjacent the user's eye for making an image 1410, in this case a projected image of a virtual Nutrition Facts label viewable by the user. The device 10 may also include an input device in the form of a touch-based input 70 that may be accessible to the user to allow the user to execute a control function of the device 10 or a function of another device that is connected or in communication with device 10.

Both display 50 and touch-based input 70 may be affixed to a frame 12 that may include features that make device 10 wearable on the head of the user. In general, frame 12 can be similar to a frame associated with a pair of glasses, e.g., prescription glasses or sunglasses. The wearable device 10, as shown in FIG. 14, lacks the lenses typically included in eyeglasses and further does not include a lower portion eyeglass frame member that can be used to help secure the lenses to the frame thereof. However, other embodiments of the device 10 discussed herein could include both lenses and additional parts or features of frame 12 that can help secure the lenses thereto.

Frame 12 may include a bridge portion 20 that may be configured to rest on a part of the nose of the user. In the embodiment shown, bridge portion 20 may include a pair of bridge arms 22 that may extend in a direction from the bridge 20. In the view of the embodiment of wearable device 10 shown in FIG. 14, bridge arms 22 may extend in a downward direction from bridge. The orientation of wearable device 10 shown in FIG. 14 may generally correspond to the orientation of device 10 when being worn by a user when the user's head is in a neutral, upright position. The description of bridge arms 22 extending downward from bridge 20 is made in such a reference frame and is done for purposes of the present description. Discussion of any other relative reference directions is also made for similar purposes and none are intended to be limiting with respect to the present disclosure, unless explicitly stated.

Bridge arms 22 may include respective pads 24 thereon, which can be positioned to rest on parts of the nose of the wearer. Pads 24 can be made of a material that is softer than arms for purposes of comfort. Additionally the material that pads 24 are made from can be flexible or have a texture that prevents slippage along the surface of the user's nose. Bridge arms 22 can be flexible to further provide a comfortable fit and or grip on the user's nose. Further, bridge arms 22 can be deformably bendable and repositionable so that the position of pads 24 can be changed to best fit the user. This can include movement closer together or farther apart or fore and aft relative to bridge 20, which can adjust the height of frame 10 and, accordingly, the position of display 50 relative to the user's eye. Further adjustment of display and other structures thereof are described in further detail below. In other embodiments, structures similar to arms and pads can be integrally formed with the remaining structure of bridge 20 and can be structured such that larger or smaller areas of the bridge contact the nose of the user, compared to the embodiment of the bridge shown. Other arrangements are also possible according to structures implemented in existing eyeglass and sunglass designs.

Frame 12 may also include one or more brow portions 30 that extend in a lateral direction away from the bridge 20. The embodiment shown includes two brow portions 30A and 30B, each extending away from opposite sides of bridge 20. In other embodiments, only a single brow portion, such as in the position of brow portion 30A, can be included extending laterally away from bridge portion 20. In such an embodiment, the single brow portion is included on the side of the display 50 and substantially nothing is on the other side of bridge portion 20. In still further embodiments, one or two brow portions can be integrally formed with or can be substituted with a specially structured lens. Brow portions 30A, 30B may be shaped to extend laterally past the user's eye while being positioned above (or alternatively below) the eye so as to not obstruct the wearer's vision. A number of different shapes and structures are possible for brow portions 30A, 30B, in addition to what is shown in the FIG. 14. The specific shape of brow portions 30A, 30B can depend on the shape and structure of bridge portion 20. As a further alternative, a single brow portion have the bridge portion affixed thereto at or near a center thereof and can extend laterally past each eye on opposite sides of the center.

Brow portions 30A, 30B can be of the same or a different material from bridge portion 20. Examples of suitable materials for the brow portion 30, or any other part of frame 12, can include various types of plastic such as polycarbonate, acrylic, ABS, and polyethylene. Any parts of frame 12, including the bridge 20 and brow portions 30, can be made from metal such as aluminum, stainless steel, titanium, nickel, gold, or various alloys including one or more of the metals listed or similar metals. Brow portion 30 can be monolithically formed with bridge portion 20 from the same material, or brow portion 30 and bridge portion 20 can be made from different materials and affixed together using adhesives, screws, various forms of welding, soldering, braising, or the like.

Frame 12 may also include one or more temple portions in the form of arms that extend from the brow portions 30, past the user's temple, and toward the user's ear. As shown in FIG. 14, frame 12 can include two arms 40A, 40B that can be positioned to extend in a rearward direction from respective brow portions 30A, 30B. In an embodiment with a single brow portion on a single side of the bridge portion, only one arm would be present. Arms 40A, 40B may provide additional points, or areas, of contact with the user's head and contribute to the device's fit and retention to the user's head. Arms 40A, 40B can be similar in structure or function to corresponding features of eyeglasses.

Arms 40A, 40B can be affixed to respective brow portions 30A, 30B, using rigid connections 42, which can be made using screws assembled between arms 40A, 40B and brow portions 30A, 30B, as shown. Alternatively, arms 40A, 40B can be affixed to respective brow portions 30A, 30B using a hinge member arranged to permit arms 40A, 40B to be folded inward toward brow portions 30 for easy storage or transportation. If hinges are used, they can be spring-loaded or the like to apply a comfortable pressure against the user's head or to accommodate a range of different head sizes comfortably. Alternatively, arms 40A, 40B can be integrally or monolithically formed with brow portions 30A, 30B. In some embodiments, arms can be made of a plastic material with internal metal reinforcement to allow bending or to prevent breakage.

Arms 40A, 40B may include respective free ends 44 opposite the connection 42 between respective arms 40A, 40B and brow portions 30A, 30B. Free ends 44 can be positioned to be located near the ear of a user when wearing device 10. Ear portions 46 can be affixed to or integrally formed with the free ends 44 of the arms 40A, 40B. As shown in FIG. 14 ear portions 46 can include an arched, or curved, form, as shown in the figures, such that they bend behind a portion of the rear of the user's ear. As with eyeglasses, the particular shape of ear portions 46 can vary in many ways including the amount by which they bend, the distance around the ear which they extend and the amount of contact, if any, actually maintained with the outside of the ear. Arms 40 can be structured to appropriately position ear portions 46 relative to brow portions 30 to achieve an appropriate fit for a user or a selection of different users. The shape of arms 40 can, accordingly, depend on the size and shape of brow portions. For example, arms 40 can extend substantially rearward from brow portion substantially perpendicular thereto and can be substantially straight. In other embodiments, arms can be angled inward, outward, upward, or downward relative to the outside ends of brow portions 30 and can further be curved in any direction (or multiple directions) to achieve a desired fit or aesthetic quality.

As shown, ear portions 46 can be separate pieces connected to the ends 44 of arms, for example by attachment via hinge 48 that permits rotation about an axis. This arrangement can allow for additional adjustability of ear portions 46 to optionally increase the amount of contact with the ear, or to allow comfortable contact among different users with different head sizes, ear position, etc. In other embodiments, ear portions 46 can be fixedly attached or monolithically formed with arms 40. In a further embodiment, ear portions 46 can extend substantially in-line with arms 40 or can extend inward therefrom, rather than downward, to a position where they rest over the ear on a topmost area thereof but do not hook around the ear. In such an embodiment ear portions 46 or arms 40 can be configured to exert a pressure against the side of the user's head to at least partially retain frame 12 to the user's head by friction generated through the pressure. Ear portions 46 can be made of a similar material to arms 40 or can be made of a different material, such as a soft-touch material, including various thermoplastic elastomers, with either compliant or high friction characteristics.

As mentioned previously, the wearable device 10 can include various input and output structures affixed to frame 12. An output structure can be in the form of a display unit 50 that may include a prism 54 mounted on a housing 52 that can also contain electronic components associated with the display. In the embodiment shown, prism 54 may be used to display an image generated by the electronic components of the display. Prism 54 may be structured to receive a projected image in a receiving side and to make that image visible to a user by looking into a viewing side of prism 54. This can be done by making prism 54 with a specific shape and/or material characteristics. In the embodiment of FIG. 14, the receiving side of prism 54 may be adjacent to or within housing 52 such that the electronic components inside housing 52 can contain a video projector structured to project the desired video image into receiving side of prism 54. Such projectors can include an image source such as LCD, CRT, and OLED displays and a lens, if needed, for focusing the image on an appropriate area of prism 54. The electronic components associated with display unit 50 can also include control circuitry for causing the projector to generate the desired image based on a video signal received thereby. The image 1410 comprising a virtual Nutrition Facts label in FIG. 14 is illustrated for convenience as being projected away from the viewing direction of a user, it being understood that the virtual Nutrition Facts label 1410 would generally be projected in the opposite direction to that shown, i.e., toward a user's eye, and would therefore appear as a reverse image from the perspective of FIG. 14.

The receiving surface of the prism 54 can be perpendicular to the viewing surface of prism 54 such that a transparent prism can be used to combine the projected image with the view of the environment surrounding the wearer of the device. This may allow the user to observe both the surrounding environment and the image of display unit 50. The prism 54 and the display electronics can be configured to present an opaque or semi-transparent image, or combinations thereof, to achieve various desired image combinations.

Display unit 50 can be affixed to frame 12 so that prism is 54 is positioned beneath brow portion 30A or in a position so that the user can comfortably observe the viewing surface and/or the projected image 1410. A number of different positions for prism 54 are possible to meet these criteria. For example, the prism can be positioned directly in front of the user's eye or can be positioned above or below the center of the user's eye, allowing the image of the display device 50 to be out of the user's direct, or straight ahead, sight line, but still allowing the user to direct his or her eyes up or down within a comfortable range to see the image within the prism 54. The prism 54 can be positioned to the left or the right of the center of the eye to achieve a similar affect. Frame 12 or the attachment between display housing 52 and frame 12 can permit user adjustment of the position of prism relative to the user's eye. For example, the vertical location of prism 54 can be changed by adjusting the bridge arms 22 of bridge portion 20, which will raise and lower brow portion 30 on the user's face, and accordingly, raise or lower prism 54, which is affixed to frame 12.

In the embodiment shown, display housing 52 may be attached to frame 12 in a receiving structure 32 of frame 12 that is formed as a part of brow portion 30A. Receiving structure 32, as shown, may include a flared top 34, a downwardly depending side and an inwardly-extending bottom 38. These three sides of receiving structure 32 can be configured to secure housing 52 to frame 12 or to provide protection for housing 52 or to achieve a desired aesthetic appearance. In other embodiments, additional or fewer sides of receiving structure 32 can be included. For example, housing can affix to the top 43 or receiving structure 32 only and the structure 32 can lack any sides or bottom.

Rotation of housing 52 relative to frame 12 can allow for adjustment in the angle of viewing surface of prism 54 relative to the user's eye. This adjustment can be useful to allow the image within prism 54 to be properly viewed by the user throughout various vertical positions of prism 54 relative to the user's eye due to device 10 fitting differently on different user's faces or due to selective adjustment of the vertical position of prism 54 on the user's face, as discussed above.

An input device in the form of a touch-based input 70, may also desirably included in wearable device 10 and affixed to frame 12. Touch-based input 70 can be a touchpad or trackpad-type device configured to sense at least one of a position and a movement of a finger via capacitive sensing, resistance sensing, or a surface acoustic wave process, among other possibilities. Touch-based input 70 can further be capable of sensing finger movement in a direction parallel or planar to the pad surface, in a direction normal to the pad surface, or both, and may also be capable of sensing a level of pressure applied. Touch-based input 70 can be formed having an outer layer of one or more insulating, or dielectric, layers that can be opaque, translucent, or transparent and an inner layer of one or more conducting layers that can be opaque, transparent, or translucent.

The structure of touch-based input 70 can include a housing 76 that can have an outside and an interior cavity for containing the inner layer of the touch-based input 70 and any electrical structures, such as control circuitry, associated therewith. The outer layer of the touch-based input 70 can be an outer wall of the housing and can include the entire wall or a selected operable area in the form of one or more touch-surfaces 72 thereof, as dictated by the size, shape, and position of the inner layer of the touch-based input 70. If a portion of the housing is to be used as the outer layer of the touch-based input 70, then the housing 76 can be made of a dielectric material such as plastic. In an alternative embodiment, the touch surface 72 is a discrete element that is mounted in an opening in the housing 76.

In the embodiment shown in FIG. 14, touch-based input 70 may be mounted on arm 40A and define a vertical plane that overlies a portion of the side of the user's head. Accordingly, touch-based input 70 may not be visible to a user of the wearable device 10, when it is being worn. To help the user identify any touch surfaces 72 of touch-based input 70 the housing 76 can be formed to have a texture provided by a raised, indented, or roughened surface so as to provide tactile feedback to a user when the user's finger contacts the touch surface 72. Such a texture can define the boundaries of the touch surface 72, can be consistent through the touch surface 72, or can vary along horizontal and vertical lengths of the touch surface 72 to give the user feedback as to the location of a finger contacting touch surface 72.

As shown in FIG. 14, in the present embodiment, the housing 76 or touch-based input 70 can be affixed to the frame 12 at a joint portion 42A thereof that extends from the side 36 of receiving portion 32. Joint portion 42A can be integrally formed with brow portion 30A, including with receiving portion 32, and housing 76 can be rigidly affixed thereto, such as by screws or other fasteners. The housing for touch-based input 70 can be arranged such that touch surface 72 is flush with a surface of joint portion 42A to provide a uniform appearance. Alternatively, joint portion 42A can include a hinge to allow arm 40A to be folded inward with free end 44 positioned near brow portion 30B, as discussed above. Arm 40A can be affixed to housing 76, as shown on a side opposite touch surface 72. Further, arm 40A can be configured to partially enclose touch-based input 70 by being a part of the housing 76 thereof. In another embodiment, arm 40A can be configured similarly to arm 40B and touch-based input 70 can be mounted thereto.

Touch-based input 70 can also include additional touch surfaces 72 such as the top or bottom surfaces of housing 76. This can be achieved by positioning capacitive sensor layers, for example, beneath the selected housing surfaces. In other embodiments, additional touch-based inputs can be provided in different locations of device 10 such as on brow portion 30A or on display housing 52. Each of the touch-based inputs 70 can be operated independently, and can provide different functions. Additionally, housing 76 can include additional input structures, such as buttons (not shown) that can provide additional functionality for wearable device 10, including implementing a lock or sleep feature or allowing a user to toggle the power for device 10 between on and off states.

Touch-based input 70, or another type of input, can be used to provide a control function that is executed by device 10, such as by an on-board CPU, or by a remote device, such as a smartphone or a laptop computer. In an embodiment information related to the control function is viewable by the user on display 50. In one example, the control function is the selection of a menu item. In such an example, a menu with a list of options can be presented on display 50. The user can move a cursor or can scroll through highlighted options by predetermined movement of a finger along touch-based input 70 and can confirm the selection by a different movement, the acceptance of the selection being indicated by the display. Examples of menu item selections can include whether to answer or decline an incoming call on a remotely-linked smartphone or to scroll or zoom-in on a map presented in display.

Additional input structures can be included in device 10. These can include a camera 26 and a sensor 28, as shown in FIG. 14. The camera 26 can be used to take picture or record a video at the user's discretion. The camera can also be used by the device to obtain an image of the user's view of his or her environment to use in implementing augmented reality functionality. The sensor 28 can be, for example a light sensor, bar code scanner, RFID reader, etc., that can be used by firmware or software associated with the camera 26. As shown, the camera and sensor can be included in a housing 78 positioned within the receiving structure 32 and in front of display housing 52. Other locations for the camera 26 and sensor 28 are also possible.

One or both of the display housing 52 and the touchpad housing 72 can contain electronic circuitry and/or a power source, such as a battery for wearable device 10. This circuitry can include controls for the touchpad 70, the display 50, the camera 26, or the sensor 28. Additionally one or both of the housings can include memory, a microprocessor or communications devices, such as cellular, short-range wireless (e.g., Bluetooth), or Wi-Fi circuitry for connection to a remote device. Additionally, any such circuitry can be included in earpiece housing 80 that is integrally formed with one or more of the ear portions 46 discussed above. As shown in FIG. 14, earpiece housing 80 may be configured to be positioned behind or over the ear of the user while being worn. Earpiece housing 80 can be further configured to contact a portion of the user's head to help secure the position of device 10. Earpiece housing 80 can be configured to include a battery or multiple batteries of various forms, such as AAA, AA, or 9-volt, or watch style batteries. The battery can also be a rechargeable battery such as a lithium-ion or nickel-cadmium battery and can be removable by the user or can be permanent or semi-permanent. Earpiece housing can also include a port 82 that can be used to connect the wearable device 10 to a power source to recharge a battery without removal thereof or to connect the wearable device 10 to a remote device for communication therewith, such as described above, or to update or install software or firmware included in the memory of the wearable device 10.

Earpiece housing 80 can be configured and positioned to provide a balancing weight to that of touch-based input 70 or display housing 50. Both touch-based input 70 and display housing 50 may be positioned forward of the user's ear, which causes a portion of their weight to be carried by the user's nose. By adding weight behind the user's ear (or shifting weight to behind the user's ear) in the form of earpiece housing 80, the ear becomes a fulcrum about which the weight of the display 50 and touch-based input 70 are balanced against that of the earpiece housing 80. This can relieve some of the weight on the user's nose, giving a more comfortable fit. The components within earpiece housing 80, such as a battery or various control circuitry for device 10 can be arranged to contribute to a desired weight distribution for the wearable device 10. For example, heavier components, such as a battery, can be placed toward or away from arm 42A to adjust the weight distribution. In an embodiment, a majority of the weight is carried by the ear of the user, but some weight can still be carried by the nose in order to give the device a secure feel and to keep the bridge 20 anchored on the nose to maintain a desired position for prism 54. In an embodiment, between 55% and 90% of the weight of device 10 is carried by the user's ear. Additionally, in an embodiment where earpiece housing 80 is rotatably affixed to arm 42A, the rotation of earpiece housing 80 can allow for customizable weight distribution.

Additional components can be included in device, such as additional inputs, control circuitry boards, antennae or the like. The various locations in which these additional components are affixed to frame 12 can also be selected to allow for a predetermined weight distribution.

Other types of display elements may also be used with the wearable device. For example, the lens elements themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within frame elements of the wearable device for driving such a matrix display. Alternatively or additionally, a laser or LED source and scanning system could be used to draw a raster display directly onto the retina of one or more of the user's eyes. Other possibilities exist as well. The lens element(s) may include a display and may be configured to overlay computer-generated graphics upon the user's view of the physical world.

The wearable device may comprise, for example, a Google Glass device. Such devices comprise a mini-projector that blasts information into a prism that redirects imagery directly toward a user's retina, much of which depends on the placement of Glass on the user's head.

Such wearable devices may be particularly well-suited for situations in which a user thereof wishes, for example, to bypass a food or beverage seller that does not disclose Nutrition Facts at the point of sale of food or beverage products for immediate consumption, and whose food or beverage dispensers are not configured to disclose such information, by conveniently accessing and displaying such information at the point of sale for himself or herself. As illustrated by the system 1400 of FIG. 14, the wearable device 10 may be configured to display a projected image 1410, in this example, an app 1411 such as "Fooducate," and/or a virtual Nutrition Facts label 1412 associated with a food or beverage product for immediate consumption dispensed from a food or beverage product dispenser 1415, such as The Coca-Cola Company Freestyle dispensing machine, even if such machine is not itself configured to disclose or display Nutrition Facts for the products it serves. In one aspect, the wearable device 10 may be configured to display the virtual Nutrition Facts label 1412 in real time, for example, as described in co-pending U.S. patent application Ser. No. 14/335,855.

The system 1400 of FIG. 14 may be configured to download and display Nutrition Facts data or information, for example, specific to a product selected from the food or beverage dispensing machine 1415. This may be achieved in multiple ways, illustrated in FIG. 14. In one aspect, the camera 26 and/or sensor 28 of the wearable device 10 may comprise a field of view represented schematically by lines 1416, 1417 that may, based on a wearer pointing the camera 26 and/or sensor 28 in a particular direction, sweep across and/or access visual data from the relevant field of view. For example, the camera 26, may, in conjunction with the sensor 28, similar to the "Fooducate" app as used on a smart phone, scan a bar code(s) 1418 for a food or beverage product selected for dispensing or mixing, and store the resulting data therefrom, which may comprise Nutrition Facts data. The Nutrition Facts for the food or beverage product selected may be displayed, for example, as the projected image 1410 on the wearable device 10. In this aspect, the company whose products are being dispensed from the food or beverage dispensing machine 1415 may either post scannable indicia such as a bar code (i.e., two dimensional bar code) or may display such indicia on the display 1414 associated with the food or beverage dispensing machine 1415. Or, the restaurant or other food outlet at which the food or beverage dispenser 1415 is located may print a bar code 1418 on the receipt (not shown) from which the consumer may, relying on the wearable device 10, scan the bar code 1418 to access Nutrition Facts data for the food or beverage product to be dispensed. Such access to Nutrition Facts data may be done via a remote database, i.e., via a smart phone app like "Fooducate," or via a database contained within the wearable device 10 and/or beverage dispenser 1415.

But companies that sell food or beverage products for immediate consumption may not always wish to disclose such information, such as Nutrition Facts for such products, and unless the FDA or other governmental agency requires such disclosure, such companies may determine it is in their economic interests not to conveniently disclose such facts. But consumers may wish to access such information more readily and in a more visually effective format than might be available, for example, by attempting to access such information via a smart phone at the point of sale and/or point of dispensing.

Thus, in another aspect, the wearable device 10 may comprise sufficient power and computing capability, similar to a smart phone, enabling the wearable device 10 to access the Internet 1430, and/or with a smart phone (not shown) from which Nutrition Facts data for a selected product may be downloaded, for example, from a smart phone app such as "Fooducate," and/or the product seller's website disclosing such facts. This may be achieved automatically, with minimal user effort, for example, by configuring the wearable device 10 with, or associating the wearable device 10 with, image recognition software that recognizes icons or brands of food and beverage products. Such image recognition is currently in its infancy, however, an "augmented reality" app known as the "Blippar" app, currently being advertised by Blippar, 225 Bush Street, San Francisco, Calif. 94104, USA, is reportedly capable of recognizing brand images and overlaying content based on such recognition. Food and beverage companies currently employ the Blippar app primarily for advertising and promotion, for example, PepsiCo uses the app to give consumers a chance to win free Super Bowl tickets. To the inventor's knowledge, however, the Blippar app is not currently used to overlay content comprising Nutrition Facts for the scanned food or beverage products. Based on such image recognition, according to the teachings herein, a remote or mobile device such as a wearable device 10 or smart phone may now use image recognition technology to access publicly available Nutrition Facts data or other facts pertaining to ingredient attributes of a scanned food or beverage product. In this aspect, the recognition software may, based on an image obtained by a user of the wearable device via camera 26 and/or sensor 28, such as a brand icon 1419 representative of a selected product, and/or representative of a graphical user interface button for a selected product, access publicly available Nutrition Facts data for the selected product, in this case for a regular sugar-sweetened Coke® brand cola beverage of The Coca-Cola Company, accessible, for example, at http://productnutrition.thecoca-colacompany.com/. Because such websites tend to display nutrition facts data in cluttered tables, for numerous products, in fine print, and not in the format mandated by the FDA for packaged products, the wearable device 10 may further comprise software configured to parse the Nutrition Facts data from such websites in order to display Nutrition Facts only for the product of interest, and in FDA-approved format, i.e., in a form of a packaged food or beverage product corresponding to the food or beverage product for immediate consumption, such as virtual Nutrition Facts label 1412. Because such brands and icons 1419 tend to be used consistently and change little, if at all, from year to year, the image recognition software associated with the wearable device 10 may be reliable for long periods of time without significant updating. Because the use by the image recognition software of such brands and brand icons 1419 qualifies as a nominative fair use, there is no requirement for the user of such brands and icons, in this context, the seller of wearable devices, apps such as "Fooducate," and/or the consumer to obtain a trademark license from the brand owner.

As previously disclosed, the wearable device 10 may be configured to display the virtual Nutrition Facts label 1412 in real time, i.e., such that a user accessing a food or beverage product dispenser 1415 may visualize in real time how much of the ingredient attributes they are dispensing, and may thereby halt dispensing once the preferred number of calories, grams of sugar, etc., are dispensed.

Consumers, however, may not know or be able to access the dispensing rate of food or beverage products being offered by food or beverage product dispensers such as the Coca-Cola Freestyle dispensing machine. Such data, however, is easily determined with a stopwatch and a measuring cup. While there may be some variability from machine to machine, in general, food and beverage sellers, who rely on repeatability and tight quality control for their dispensing equipment, generally may prefer to have like machines perform, within reasonable tolerances, as similarly as possible from machine to machine. Moreover, manufacturers of such machines likewise tend to produce them within tight manufacturing tolerances designed to insure that the same model performs the same way time and again. It is therefore reasonable to assume that consumer-gathered data regarding dispensing rate may be relied upon, for example, by smart phone app providers such as Fooducate LTD. Indeed, the "Fooducate" app is configured to permit consumers, wishing to gather Nutrition Facts for a food or beverage product that is not yet in the Fooducate database, to take photos of the relevant food product, its Nutrition Facts label, and UPC bar code, and send same to Fooducate LTD to permit such data to be added to the "Fooducate" database for future use. Employing a like concept, consumers may send real world dispensing equipment dispensing rate data, and/or brand icon images, to similar apps and/or to sellers of wearable devices such as the Google Glass or Apple iWatch devices, in order that dispensing rate data and/or Nutrition Facts data for dispensing machines of interest to consumers is stored and accessible for use by consumers at the point of sale or dispensing.

Once such dispensing rate and Nutrition Facts data is available, it may be readily accessed by the wearable device 10 and employed as disclosed herein to determine, and display, in real time, virtual Nutrition Facts labels and similar ingredient attribute information.

Figure 15:
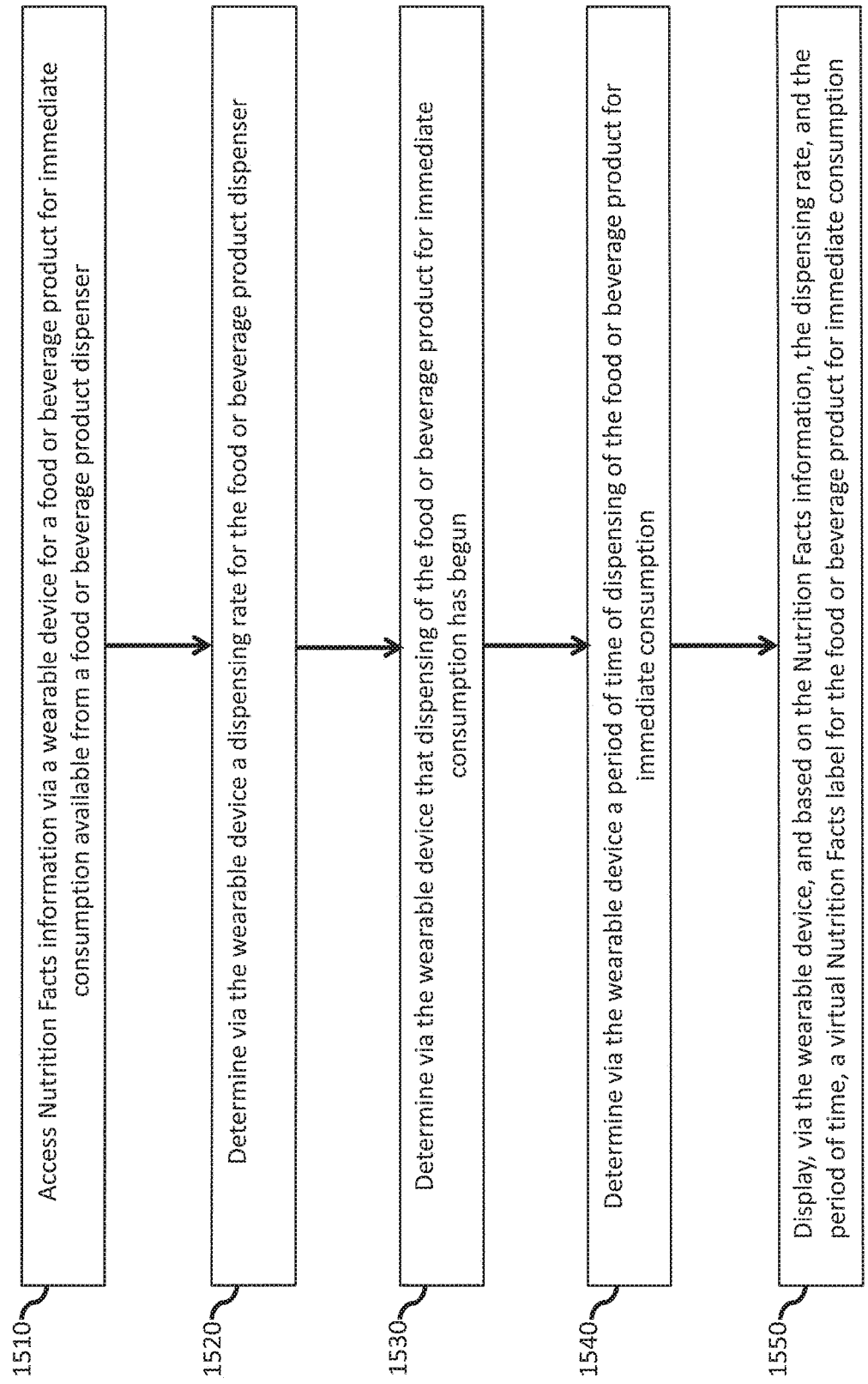
FIG. 15 is an illustrative embodiment of a method of the disclosure, illustrative of using the wearable device and/or system of FIG. 14 with a food or beverage product dispenser.

Referring now to FIG. 15, there is disclosed a flow diagram illustrating a method according to the present disclosure. As illustrated at operation 1510, the method may comprise accessing Nutrition Facts information, via a wearable device 10, for a food or beverage product for immediate consumption available from a first food or beverage product dispenser 1100, 1200, 1415. Accessing such Nutrition Facts information may be achieved in a number of ways. For example, the wearable device may access a remote database on which the Nutrition Facts data or information is stored, for example a database associated with an app such as "Fooducate." Alternatively, the Nutrition Facts data or information may be accessed on a database of the food or beverage company whose food or beverage products for immediate consumption are being dispensed by the first food or beverage product dispenser. Such Nutrition Facts data or information may be parsed via the wearable device, thereby rendering a virtual Nutrition Facts label in a form corresponding to FDA requirements for a packaged product corresponding to the food or beverage product for immediate consumption.

At operation 1520, a dispensing rate for the food or beverage product dispenser may be determined via the wearable device 10. This too may be accomplished in a number of ways, including, for example, by accessing a remote database on which the dispensing rate is stored, the dispensing rate comprising a real world dispensing rate for a second food or beverage product dispenser substantially similar to the first food or product dispenser. This real world dispensing rate may be achieved, for example, by "crowdsourcing" data from numerous consumers or consumer advocates who may determine real world dispensing rates from one or more similar, publicly available food or beverage product dispensers and share such real world dispensing rates, for example, with app companies such as Fooducate LTD for further use and processing. Such real world dispensing rates may be averaged to account for variations in methodology and accuracy of data gathering, it being generally understood that the greater the number of real world dispensing rates obtained, the more reliable the average, it being further understood that real world dispensing rates that exceed a predetermined deviation from the norm may be disregarded as outliers.

As another example, the dispensing rate may be determined by the wearable device 10 capturing, via a sensor 28 and/or camera 26, real time imaging of the food or beverage product for immediate consumption during dispensing thereof. In this aspect, the dispensing rate may be determined by determining a volume for at least a portion of a container for the food or beverage product for immediate consumption, determining a relationship of container fill height to fill volume, and determining at least one product fill height during a dispensing operation of the food or beverage product for immediate consumption and a time period to reach the fill height. This may be accomplished as previously described, but with the added twist of employing the wearable device sensor 28 and/or camera 26 to visually or via sensing determine, for example with image recognition software, the relevant volumes, heights, time periods, etc., and processing the resulting data to arrive at the dispensing rate.

Of course, the dispensing rate may be further determined by accessing such information directly from the food or beverage dispenser 1100, 1415, for example, by accessing via a wireless connection a database associated with the food or beverage product dispenser and/or by accessing a website of the company with which the products being served by the food or beverage dispenser 1100, 1415 are associated, assuming such company wishes to be forthcoming with such data.

At operation 1530, the wearable device may be used to determine that dispensing of the food or beverage product for immediate consumption from the first food or product dispenser has begun. This operation may be useful, for example when a time period for the dispensing operation is desired, for example, to determine a dispensing rate, and/or to display a virtual Nutrition Facts label in real time. This determination may, for example, be achieved using the camera 26 and/or sensor 28 to visually or via sensing, i.e. with ultrasound, an ultrasound level sensor, a microphone, or a voice-activated device, similar to that used to activate Siri on Apple iPhones, to determine that the dispensing operation has begun. As will be readily appreciated, a user of the wearable device 10 may conveniently point the camera 26 and/or sensor 28 at the food or beverage product being dispensed in order to initiate this operation. Alternatively, in the case of the wearable device being configured with a microphone for picking up audible cues, such as the sound of a beverage being dispensed into a container, this operation 1530 may commence upon such audible cue being detected by the wearable device 10.

At operation 1540, the wearable device 10 may be used to determine a period of time of dispensing of the food or beverage product for immediate consumption. This may be accomplished using a timer built into the wearable device 10 that may be configured to initiate a timing sequence, for example, at operation 1530, and conclude the timing sequence upon receiving a cue, i.e., visual, audible, etc., as discussed above, that the dispensing operation has ceased.

At operation 1550, the wearable device 10 may be used to display, based on the Nutrition Facts information, the dispensing rate, and the period of time, a virtual Nutrition Facts label for the food or beverage product for immediate consumption. Such virtual Nutrition Facts label may be displayed via the wearable device 10 projector via a prism, heads up display, or otherwise. The virtual Nutrition Facts label may be displayed in real time, and/or may be displayed as a static virtual Nutrition Facts label at the conclusion of the dispensing operation.

As will now be appreciated, the wearable device 10 may, for example, comprise a mobile device such as a Google Glass device, an Apple iWatch, an implanted chip, a wrist band, a smart phone adapted to be worn, etc., any of which may comprise, for example, a transmitter and/or a receiver, and may comprise or be associated with a heads up display (HUD) or other display associated with the user, configured according to the teachings herein. In a preferred aspect, the wearable device may comprise a Google Glass device and/or an Apple iWatch. As illustrated, these devices may comprise a display, i.e., projected image, or a HUD in the case of the Google Glass device, and a watch face display in the case of an Apple iWatch type device. As is known, users of such devices tend to be sophisticated and technology savvy "early adopters". They, more than the average consumer, will tend to be most interested in accessing data associated with the food and beverage products they consume.

In this aspect of FIG. 14, the wearable device 10 may communicate with any of the food or beverage dispensers or food processors or blenders disclosed herein, or any vending machine for a food or beverage product. The projected image, HUD and/or watch face display (collectively "wearable device display") may be configured to display, for example, in real time, Nutrition Facts for food or beverage products as they are being dispensed, as described, for example, in co-pending U.S. patent application Ser. No. 14/335,855.

Figure 16:
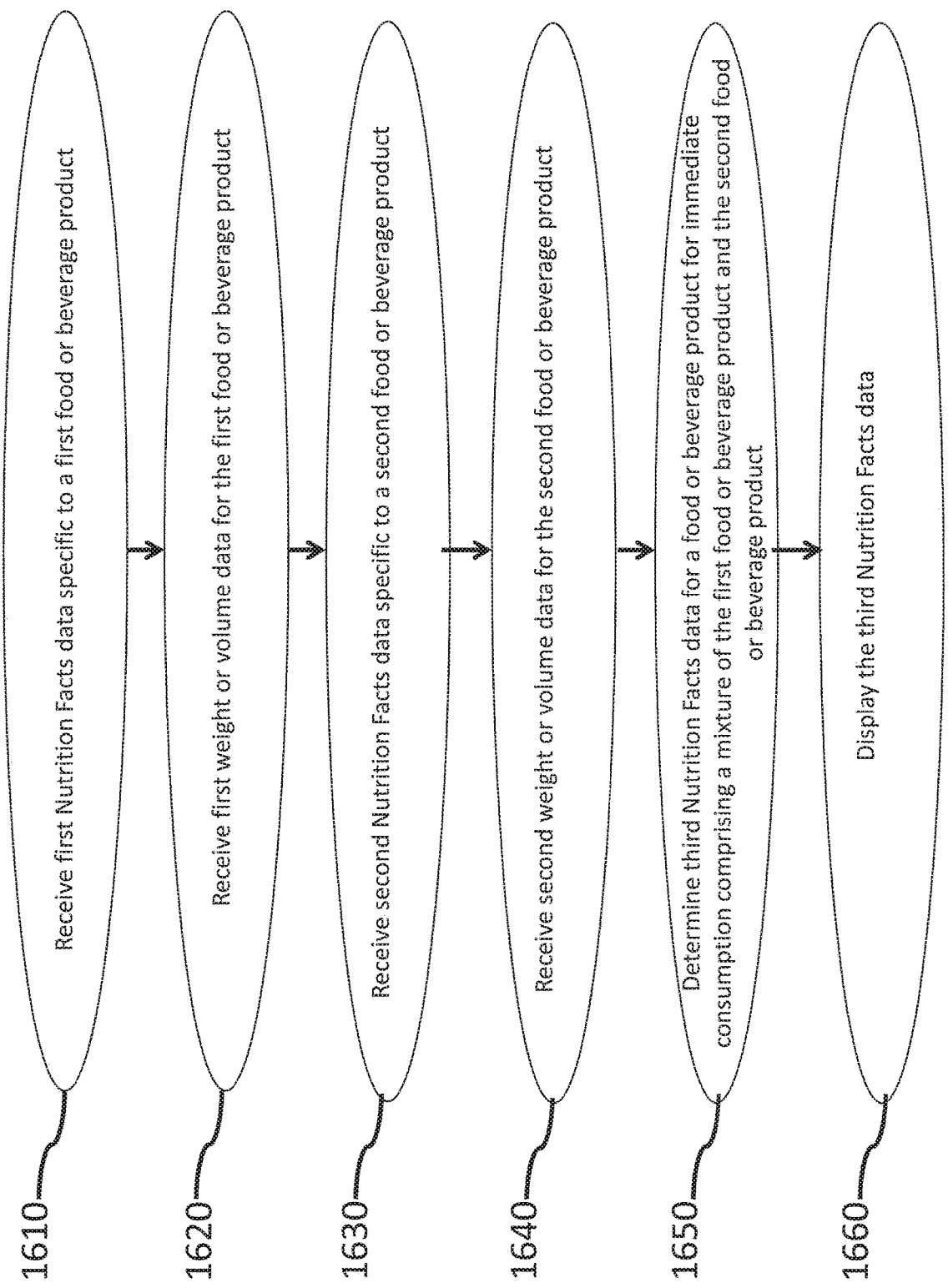
FIG. 16 is an illustrative embodiment of a method of the disclosure, illustrative of using the system of FIG. 7, the food or beverage product dispenser of FIG. 11, the food processor or blender and/or system of FIG. 12, and/or the system of FIG. 14.

Referring now to FIG. 16 there is illustrated a flow diagram representative of another method of the disclosure, for example, as may be employed using one or more of the apparatus described herein, such as the food processor or blender 1200 of FIG. 12. While the operations of FIG. 16 are illustrated with respect to a first and second food or beverage product, it will be understood that such operations may be carried out with more food or beverage products or even with just one food or beverage product. As illustrated at operation 1610, first Nutrition Facts data specific to a first food or beverage product, such as blueberries, may be received. Such data may, for example, be received via a bar code or RFID scanner that may scan a bar code on a label applied to or a package containing the food or beverage product or an RFID chip associated with the food or beverage or its package. Such scanning may, as previously described, result in the first Nutrition Facts data being retrieved, for example, from a website hosted by the seller of the first food or beverage product, from a smart phone app, such as "Fooducate," or from a database housed within a device such as a beverage dispenser or blender.

At operation 1620, first weight or volume data specific to the first food or beverage product, such as 100 grams of blueberries, may be received. This may be achieved, for example, via a weighing device such as previously described that may weigh the food or beverage product and may transmit or send weight data therefore, for example, to a processor for further processing. For liquid products, volume data may be received, for example, via a user input, or the weighing device may be used but appropriately tared to account for the weight of a container in which the food or beverage product has been placed.

At operation 1630, second Nutrition Facts data specific to a second food or beverage product, such as plain fat free yogurt, may be received, employing data sources which may be similar to those employed at operation 1610.

At operation 1640, second weight or volume data for the second food or beverage product, such as 1 cup of plain fat free yogurt, may be received, for example as previously described.

At operation 1650, for example, based on operations 1610, 1620, 1630, and 1640, third Nutrition Facts data for a food or beverage product for immediate consumption comprising a mixture of the first food or beverage product and the second food or beverage product may be determined. This may, for example, be accomplished by aggregating the Nutrition Facts attributable to each of the food or beverage products in the final mix, based on their relative proportions of the final mix.

One or more of the first Nutrition Facts data and the second Nutrition Facts data may be received via a scanner configured to read a bar code associated with one or more of the first food or beverage product and the second food or beverage product. One or more of the first Nutrition Facts data and the second Nutrition Facts data may be received via a user interface configured to input Nutrition Facts data, for example, via a touch screen associated with a beverage dispenser, a blender, a mobile device associated with a user and communicatively coupled to the beverage dispenser, etc.

At operation 1660, the third Nutrition Facts data may be displayed. Such displaying of the third Nutrition Facts data may comprise one or more of (1) displaying the third Nutrition Facts data on a display, such as a monitor, a wearable device display, a beverage dispenser display, a blender display, etc.; (2) printing the third Nutrition Facts data on a receipt, such as may be printed at a cash register or from a beverage dispenser or blender; (3) printing the third Nutrition Facts data on a label intended to be applied to a container for the food or beverage product for immediate consumption; and (4) printing the third Nutrition Facts data on the container.

Figure 17:
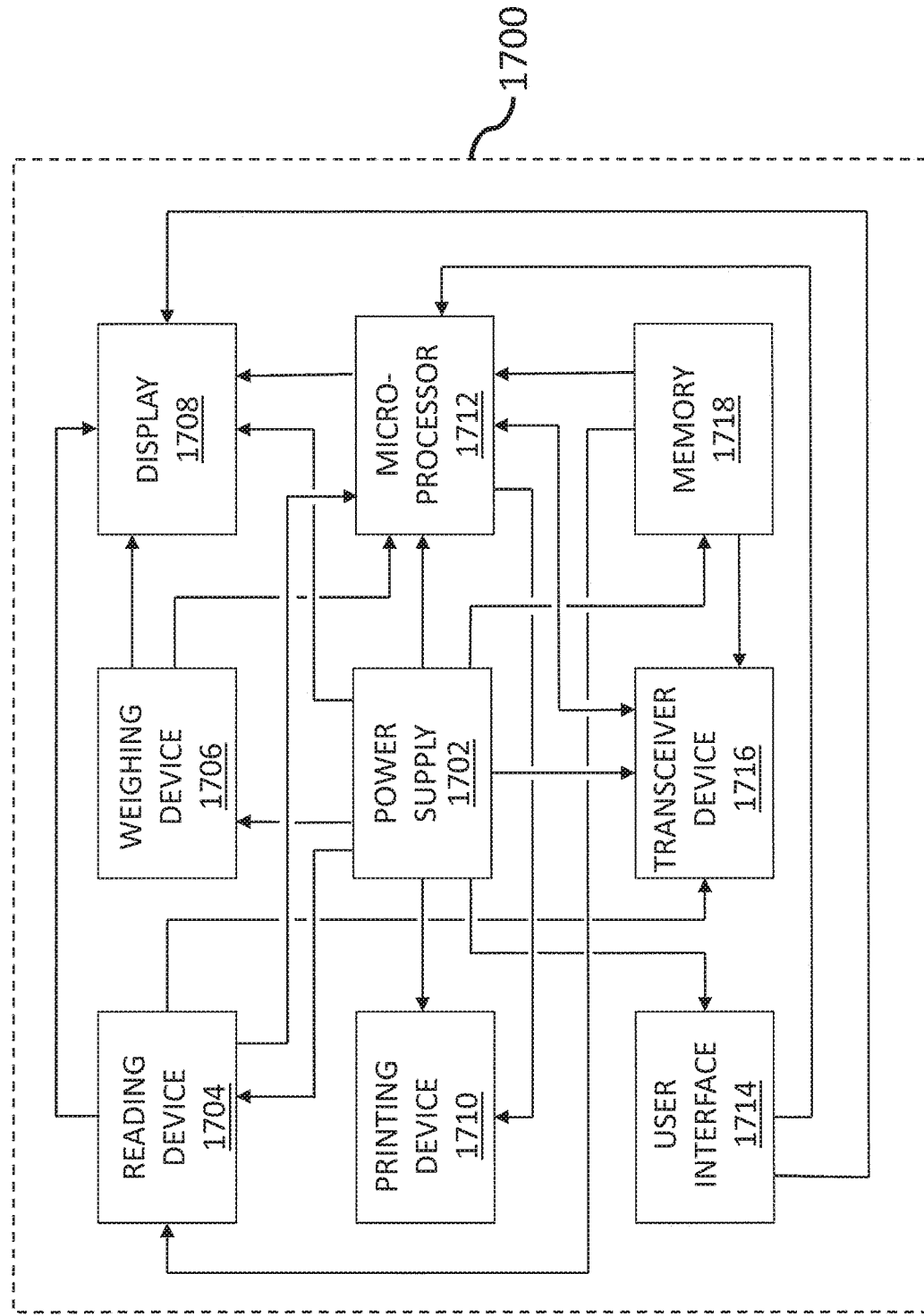
FIG. 17 is an illustrative embodiment of a system block diagram for use with the apparatus, systems, and methods of the disclosure.

FIG. 17 illustrates one example of a system 1700 block diagram for use with the apparatus, systems, and methods of the disclosure. The system 1700 may be integrated into a beverage dispensing station, a fountain dispenser, an automated beverage system, a food processor, or a blender, or a handheld or mobile device, i.e., a smart phone or a wearable device. Indeed, the system 1700 may be integrated into any dispensing or processing mechanism for dispensing or processing any type of product, including, without limitation, food products, pharmaceutical products, candy, coffee, (including beans and ground), or any other product that can be dispensed and needs to be distinguished from other products that can be dispensed from or processed by the same dispensing or processing mechanism. As illustrated, a power supply 1702 may power one or more components of the system 1700, such as a reading device 1704, a weighing device, 1706, a display 1708, a printing device, 1710, a microprocessor, 1712, a user interface, 1714, a transceiver device, 1716, and/or a memory, 1718. The power supply may comprise a standard electric cord, receiving power via a wall outlet, a battery, a battery pack, via induction, or other known power supply systems.

The reading device 1704 may comprise, for example, a reading device, such as a scanner previously described, configured to read and process machine-readable codes. Such machine-readable codes may comprise, for example, a MICROSOFT TAG, a DATAMATRIX code, a QRC code, a barcode, graphics, black and white tags, color tags, RFID code, and/or any other type of machine-readable indicia. The reading device 1704 may access a remote database, i.e., via transceiver 1716, or may access a memory 1718, which may, for example, comprise a database of Nutrition Facts for food or beverage products comprising, for example, bar codes or other machine-readable codes for reading by the reading device 1704. The reading device 1704 may be interconnected with the microprocessor 1712.

The weighing device 1706 may comprise, for example, a weighing mechanism such as previously described, including without limitation, piezoelectric transducers used to weigh items. The weighing device may interconnect with the reading device 1704, the microprocessor 1712, and/or the display 1708.

The display 1708 may comprise a display as previously described, whether on or associated with a food or beverage product dispenser, a food processor or blender, a wearable device, or a mobile device. The display may interconnect with the microprocessor 1712, the weighing device 1706, the reading device 1704, and/or the user interface 1714.

The printing device 1710 may comprise a printing mechanism configured to print indicia on the surface of a container or label, as illustrated in FIGS. 3, 5, 6, 7, 10, 11, 12, and/or 13. Such a printing device 1710 may print by way of thermal, ink jet, radiation exposure or reactive inks applied on the container surface, an/or by other printing methods. The printing device 1710 may create graphics and text indicia by way of pixel based printing methods such as dot matrix style and/or by way of other types and/or kinds of printing methods. The printing device 1710 and/or reading device 1704 may comprise or communicate with a level indicator such as previously disclosed herein.

The microprocessor 1712 may be configured to process electrical signals output by other components such as the reading device 1704. In some aspects, the microprocessor may be a programmable microprocessor, while in other aspects the microprocessor 1712 may be a purpose-specific device, such as an ASIC. The microprocessor 1712 may be configured to perform any desired operation, for example, on signals output by the reading device 1704, or the weighing device 1706, such as curve smoothing, noise filtering, outlier removal, amplification, summation, integration, and the like. The microprocessor 1712 may, for example, be an INTEL, MOTOROLA, AMD, ZILOG, MICROCHIP, RABBIT, and/or other types and kinds of microprocessors, as may be required and/or desired. The microprocessor 1712 may be interconnected with one or more of the reading device 1704, weighing device 1706, display 1708, printing device 1710, user interface 1714, transceiver device 1716, and/or memory 1718.

The user interface 1714 may comprise known user interfaces, such as a touch screen, push buttons, graphical user interface, etc., may interconnect with the microprocessor 1712, and may interconnect with and/or comprise the display 1708. In a preferred aspect, the user interface 1714 may, for example, be used when a food or beverage product is not coded with machine readable indicia, and the user may thus have the option to enter Nutrition Facts and/or other ingredient specific information manually via the user interface 1714. The user interface 1714 may also be used to initiate a dispensing operation, discontinue a dispensing operation, make a food or beverage product selection, etc.

The transceiver device 1716 may be interconnected with the microprocessor 1712, reading device 1704, and/or memory 1718. The transceiver device 1716 may comprise a true transceiver, i.e., a transmitter and receiver, or may comprise just a transmitter or just a receiver, an antenna, a transponder, or other device configured to access, receive, and/or transmit data wirelessly, from or to a remote source, such as the internet, remote websites, handheld devices, wearable devices, etc.

The memory 1718 may be interconnected with the microprocessor 1712, the reader device 1704, and/or the transceiver device 1716. The memory 1718 may comprise any conventional memory device capable of downloading, uploading, or storing, data or information for processing by the microprocessor 1712. The memory 1718 may comprise a flash memory. The memory 1718 may comprise both read-only memory (ROM) and a random access memory (RAM). As will be readily appreciated by those of ordinary skill in the art, both the read-only memory (ROM) and a random access memory (RAM) may store software instructions for execution by the microprocessor 1712.

It is noted that while the depicted embodiment of FIG. 17 illustrates a microprocessor 1712, any processor appropriate to the purposes described herein may be used. According to other aspects of the disclosure, the system 1700 and its various components, i.e., the reading device 1704, weighing device 1706, and/or other components configured to provide data output may not need to include a processor or microprocessor 1712 to process data, rather, the "raw" data from such devices may be transmitted, such as by wireless transmission, without being processes, and/or may be transmitted to a remote device, such as a smart phone or a wearable device, for processing.

Any of the above mentioned aspects may be implemented in methods, systems, computer readable media, or any type of manufacture. It should be understood to those skilled in the art that the various techniques described herein may be implemented in connection with hardware or software or, where appropriate, with a combination of both. For example, aspects of the invention may execute on a programmed computer. Thus, the methods and apparatus of the invention, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, smart phone, or other machine, the machine becomes an apparatus for practicing the invention. In the case of program code execution on programmable computers, the computing device generally includes a processor, a storage medium readable by the processor (including volatile and non-volatile memory and/or storage elements), at least one input device, and at least one output device. Such programs are preferably implemented in a high level procedural or object oriented programming language to communicate with a computer system. However, the program(s) can be implemented in assembly or machine language, if desired. In any case, the language may be a compiled or interpreted language, and combined with hardware implementations. In example embodiments a computer readable storage media can include for example, random access memory (RAM), a storage device, e.g., electromechanical hard drive, solid state hard drive, etc., firmware, e.g., FLASH RAM or ROM, and removable storage devices such as, for example, CD-ROMs, floppy disks, DVDs, FLASH drives, external storage devices, etc. It should be appreciated by those skilled in the art that other types of computer readable storage media can be used such as magnetic cassettes, flash memory cards, digital video disks, Bernoulli cartridges, and the like. The computer readable storage media may provide non-volatile storage of processor executable instructions, data structures, program modules and other data for a computer.

On Nov. 26, 2014, the U.S. Food and Drug Administration (FDA) announced that in order to implement the nutrition labeling provisions of the Patient Protection and Affordable Care Act of 2010 (Affordable Care Act or ACA), the FDA is requiring disclosure of certain nutrition information for standard menu items in certain restaurants and retail food establishments and on vending machines. The new requirements were published on Dec. 1, 2014 in the Federal Register, at 79 FR 71155 and 79 FR 71259, incorporated by reference in their entirety herein, and available online at https://federalregister.gov/a/2014-27833 and https://federalregister.gov/a12014-27834, respectively, (collectively "the new FDA rules.")

The FDA has finalized two rules requiring that calorie information be listed on menus and menu boards in chain restaurants and similar retail food establishments and vending machines. The calorie or other information may be provided on a counter card, sign, poster, handout, booklet, loose leaf binder, or electronic device such as a computer, or in a menu, or in any other form that similarly permits the written declaration of the required nutrient content information for all standard menu items.

Menu labeling final rule: Applies to restaurants and similar retail food establishments if they are part of a chain of 20 or more locations, doing business under the same name, offering for sale substantially the same menu items and offering for sale restaurant-type foods.

Vending machine final rule: Requires operators who own or operate 20 or more vending machines to disclose calorie information for food sold from vending machines, subject to certain exemptions.

Americans eat and drink about one-third of their calories away from home. According to the new FDA rules, making calorie information available will help consumers make informed choices for themselves and their families.

Covered establishments will list calorie information for standard menu items on menus and menu boards and a succinct statement about suggested daily caloric intake. Other nutrient information—total calories, calories from fat, total fat, saturated fat, trans fat, cholesterol, sodium, total carbohydrates, fiber, sugars, and protein—will have to be made available in writing on request.

In addition, covered establishments will also be required to post a statement on menus and menu boards about the availability of such additional written nutrition information. To be covered, an establishment must be a restaurant or similar retail food establishment, as defined in the final rule. In addition, such establishment must: (1) be part of a chain of 20 or more locations, (2) doing business under the same name, (3) offering for sale substantially the same menu items.

Examples of restaurant-type foods that are covered when sold by a facility that is part of a chain with 20 or more locations include:

Meals from sit-down restaurants

Foods purchased at drive-through windows

Take-out food, such as pizza

Foods, such as made-to-order sandwiches, ordered from a menu or menu board at a grocery store or delicatessen Foods you serve yourself from a salad or hot food bar Muffins at a bakery or coffee shop Popcorn purchased at a movie theater or amusement park A scoop of ice cream, milk shake or sundae from an ice cream store Hot dogs or frozen drinks prepared on site in a convenience or warehouse store Certain alcoholic beverages Foods not covered include:

Certain foods purchased in grocery stores or other similar retail food establishments that are typically intended for more than one person to eat and require additional preparation before consuming, such as pounds of deli meats, cheeses, or large-size deli salads.

For vending machines, the new standards require:

Disclosing calorie information of foods sold in vending machines operated by a person owning or operating 20 or more machines, subject to certain exceptions.

Calorie information may be placed on a sign (e.g., small placard, sticker, poster) near the article of food or selection button. Electronic or digital displays may also be used.

Posting of calorie information for foods sold from bulk vending machines (e.g., gumball machines, mixed nut machines).

Disclosing contact information of covered operators on the machines or otherwise with the required calorie declarations to enable FDA to contact operators for enforcement purposes.

The new FDA rules define "self-service food" as "restaurant or restaurant-type food that is available at a salad bar, buffet line, cafeteria line, or similar self-service facility and that is served by the customers themselves. Self-service food also includes self-service beverages," and "self-service food" as used herein is intended to have the same definition. "Self-service beverages," in turn, is intended to mean beverages intended for immediate human consumption. Thus, to the extent the new FDA rules require posting of calorie or other nutrition facts information for self-service food, then food and beverage dispensers of the type described herein are subject to the new rules.

The new FDA rules define "covered establishment" as "a restaurant or similar retail food establishment that is a part of a chain with 20 or more locations doing business under the same name (regardless of the type of ownership, e.g., individual franchises) and offering for sale substantially the same menu items, as well as a restaurant or similar retail food establishment that is registered to be covered under section 101.11(d) of the FD&C Act," and "covered establishment" as used herein is intended to have the same definition.

The new FDA rules define "vending machine" as "a self-service device that, upon insertion of a coin, paper currency, token, card, or key, or by optional manual operation, dispenses servings of food in bulk or in packages, or prepared by the machine, without the necessity of replenishing the device between each vending operation," and "vending machine" as used herein is intended to have the same definition.

The new FDA rules define a "vending machine operator" as a person(s) or entity that controls or directs the function of the vending machine, including deciding which articles of food are sold from the machine or the placement of the articles of food within the vending machine, and is compensated for the control or direction of the function of the vending machine, and "vending machine operator" as used herein is intended to have the same definition.

Moreover, section 101.11(b)(2)(iii)(A)(3)(iii) of the new FDA rules requires that, for self-service beverages, calorie declarations must be accompanied by the term "fluid ounces" and, if applicable, the description of the cup size (e.g., "small," "medium"). For example, calories could be declared as "small Orange Fizz (12 fluid ounces)—150 calories." Using the teachings disclosed herein, food and beverage dispensers may now readily display, either in real time, at the beginning, and/or at the end of a dispensing operation, for example, on a display monitor such as described herein, both the number of fluid ounces of the food or beverage dispensed or to be dispensed and the number of calories associated therewith.

Moreover, § 101.11(b)(2)(iii)(A)(3)(i) of the new FDA rules require that calories for self-service food and food on display be declared to the nearest 5-calorie increment up to and including 50 calories and to the nearest 10-calorie increment above 50 calories except that amounts less than 5 calories may be expressed as zero. The systems, apparatus and methods described herein and the aforementioned co-pending application may be effectively tailored to comply with such 5 and 10-calorie increments, for example, by displaying calorie information for a dispensed product in real time, incrementally, in 10-calorie increments as the food or beverage product is being dispensed.

The new FDA rules require that Nutrition Facts information must be available to consumers upon request. The most effective way to make such information available to consumers would be via a display or a label at the point of purchase, i.e., at a fountain beverage dispenser, a Freestyle-type dispensing machine, an ice cream dispenser, at a salad bar, etc. And, as consumers become more accustomed to using technologically sophisticated machines, such as the Freestyle dispensing machine, they may wish to request such information directly from such machines. According to another aspect of the disclosure, such machines may now be configured with a "Request Nutrition Facts Information" button, icon, or similar user interface or user prompt. Such information may be advantageously made available, for example, when the consumer makes a product selection. For example, in the case of a Freestyle-type dispenser, generally 1415 of FIG. 14, the dispenser display or user interface 1414 may be configured, upon a user pressing a product selection icon, such as a Coca-Cola beverage icon 1419, to display on the display 1414 a message and/or query intended to comply with the aforementioned new FDA requirements, i.e., notifying the consumer that Nutrition Facts information for the selected beverage are available, and further notifying the consumer that such Nutrition Facts may be displayed upon request on the display 1414 and/or printed out via a printing device such as previously described.

Figure 19:
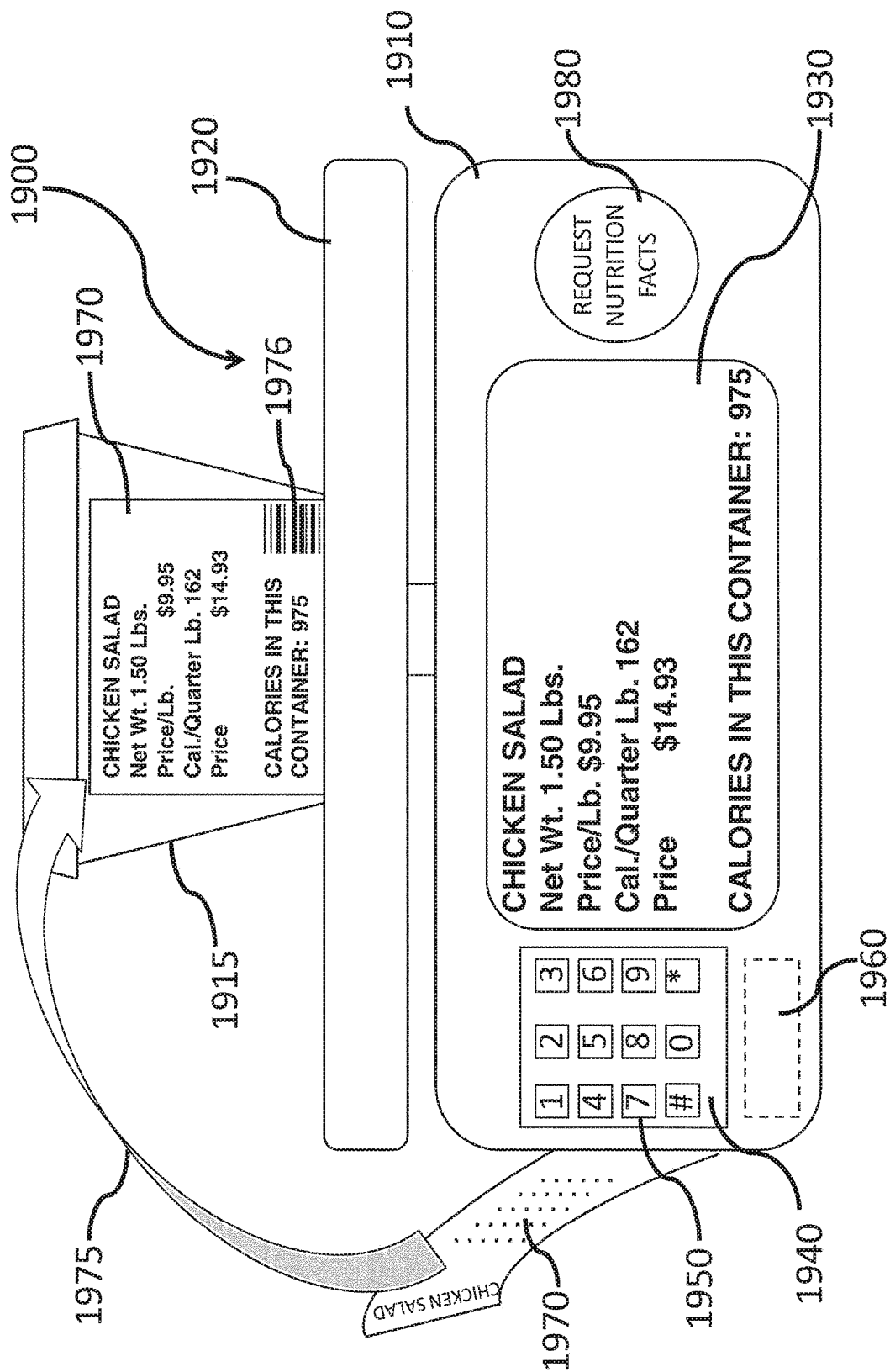
FIG. 19 is an illustrative embodiment of a system for posting calorie and other Nutrition Facts information at a point of sale and/or at a time when a consumer may have an opportunity to change his or her mind about either the type of product or quantity of product being ordered.

The teachings disclosed herein may thus enable covered establishments and consumers to more readily comply with and understand, respectively, the new FDA rules. An example is illustrated in FIG. 19. FIG. 19 illustrates a system, generally 1900 intended to enable a covered establishment to post calorie and other Nutrition Facts information at the point of sale and/or at a time when a consumer may have an opportunity to change his or her mind about either the type of product or quantity of product being ordered. Such consumer choice making is part and parcel of the new FDA rules, which require, for example, that a consumer of a covered vending machine be able to read calorie information prior to making a purchase. Thus, the calorie information must be prominently and clearly displayed such that the consumer has a fair opportunity to be informed about caloric information.

According to the embodiment of FIG. 19, the system 1900 may comprise a device 1910 which may comprise a vessel such as a food or beverage dispenser having weight and/or volume control/monitoring mechanisms, and/or may, for example in the case of solid food items, comprise a device separate from such a dispenser, and may comprise a weight or volume monitor, such as a weighing device or scale 1920, and a display panel or monitor 1930. While the display panel or monitor 1930 is illustrated as being integral with the device 1910 of system 1900, it will be readily appreciated that the display panel or monitor 1930 may comprise an electronic menu board or panel that is remote from the device 1910.

The device 1910 may further comprise a user interface, which may comprise, for example, a graphical user interface that may be part of the display panel or monitor 1930, such as the Coca-Cola Freestyle display, and/or may comprise a separate user interface 1940 which may be configured with one or more user inputs 1950. Alternatively, the user interface 1940 may comprise a mobile device communicatively coupled to the device 1910. The device 1910 may further be configured with a printer device 1960 as previously described, configured to print out a sign, label, or other information-bearing material 1970. In one aspect, the label 1970 may, as illustrated by the arrow 1975, be configured with an adhesive backing to permit the label 1970 to be applied to a container 1915. The label 1970 may further comprise a bar code or other indicia 1976 to enable the contents of the container 1915 to be scanned for checkout and payment.

The device 1910 may be further configured to communicate, for example, wirelessly, with a remote device or wearable device, as previously described. The device 1910 may further be configured with appropriate systems, software, microprocessors, databases, memory, etc., for example as schematically illustrated in FIG. 17.

The system 1900 of FIG. 19 may advantageously be used, for example, at a covered establishment. In one aspect, for example, where the covered establishment comprises a grocery store or restaurant salad bar, the system 1900 may be located in the vicinity of one or more food items, in this example, a self-service food such as chicken salad. A user may place an empty container 1915 on the device 1910, such as on a weighing device 1920. The weighing device 1920 may be configured to disregard the weight of the container 1915, or the container 1915 may be of insufficient weight to be measured by the weighing device 1920. Alternatively, the container 1915 may be weighed and the weight subtracted by the system 1900 once the consumer enters a product code as shall now be described. In this aspect, it should be noted that if ice or water is placed in the container 1915, this will not add to the calorie count of the resulting self-service food. In this aspect, the system 1900, as well as the other systems, i.e., 700, 1101, 1201 described herein may be configured to recognize when ice or water is placed in a container, and/or may be configured to dispense predetermined quantities of ice or water such that the weight thereof may be easily accounted for and disregarded during subsequent operations to determine calories, Nutrition Facts, etc. In this aspect, if the systems 700, 1101, 1201, 1900 may determine, based on a weighing device, that ice or water has been placed in a container, but that no calorie or Nutrition Facts information has been inputted, such systems may be configured to either default to treating such ingredients as ice or water, and/or may be configured to query a user if ice or water has been placed in the container.

The consumer may be prompted, for example, on the display panel or monitor 1930, or on the user interface 1940, to enter a code, such as a 4-digit code, for the food item of interest, for example, using the user inputs 1950 on the user interface 1940. Such code may be displayed proximate the food item, for example, as is customarily done for self-serve food items such as nuts and seeds, for example, at Whole Foods, where consumers write the product code on the bag into which the food product is placed for the checkout clerk to use in order to determine price at the time of checkout. Additionally or alternatively, the user interface 1940 may permit the user to enter the name of the food item, in this case, "chicken salad." As still another alternative, the user interface 1940 may comprise graphical user interface icons specific to each available food item proximate the device 1910.

The device 1910 may be configured, upon receiving the entered code or other food identification entry, to access a database displaying, for example, on the display panel or monitor 1930, such information as number of calories per serving for the selected item, i.e., "162 Cal per quarter pound," serving size, i.e., "one scoop," or "one quarter pound," price per unit of weight, i.e., $9.95 per pound, etc., to give the consumer an opportunity to change his or her mind about making the selection. Additionally or alternatively, the system 1900 may be configured to query the user if Nutrition Facts information for the selected food item, i.e., for which the code was entered, is desired. In one aspect, such query may be implied, for example, with an icon or button 1980 that the consumer may select either with or without being queried in order to display and/or print out Nutrition Facts information for the selected food product, for example on the display panel or monitor 1930 and/or on a label 1970, as previously described. In this way, a covered establishment may more conveniently and more efficiently comply with both the letter and the spirit of the new FDA rules, by making Nutrition Facts information more easily accessible to consumers, and by relieving crew servers, store managers, etc., of the need to stock, display, and respond to individual requests from consumers for such information.

In another aspect, the user interface 1940 may perform multiple functions. For example, the user interface 1940 may be configured to enable a user to enter a code or other identification to select a desired product, such as chicken salad. The user interface may be further configured to enable the user to enter the desired quantity of the desired product, for example, 1.5 pounds of chicken salad. The user interface 1940 may further be configured to enable a user to request Nutrition Facts information for the desired product. The system 1900 may be configured to prepare and dispense a Nutrition Facts label containing the Nutrition Facts information not merely for a standard serving size, as is conventional, but specific to the serving quantity placed in the container. Because the FDA only requires that calories for food and beverage products greater than 50 calories be displayed in 10-calorie increments, and most self-service food will in general be served in greater than 50 calorie quantities, the system 1900 may be configured to display calories in 10-calorie increments, provided FDA guidelines for doing so are met. Alternatively, the system 1900 may be configured to display calories in 5-calorie increments.

The system 1900 may thus be present in a covered establishment offering self-service food. The system 1900 may comprise a weight and/or volume measuring device 1920 configured to weigh, and/or determine a volume of, a selected quantity of the self-service food. The system may further comprise a display 1930 proximate the self-service food, and the system 1900 may further be configured to determine, based on the weight and/or volume of the selected quantity of the self-service food, calorie content of the selected quantity of the self-service food, and to display the calorie content, as well as other information such as price, quantity, calories per serving, etc., on the display 1930. The display 1930 may comprise an electronic, i.e., liquid crystal type display.

The display 1930 may be associated with one or more of a fountain (sometimes termed "legacy") beverage machine, a Freestyle-type dispensing machine (also intended to include Pepsi Spire dispensing machines), a frozen yogurt machine, a milkshake dispensing machine, a soft ice cream machine, a buffet, a cafeteria, and a salad bar. The display 1930 may be integral with and/or separate from such machines, buffets, cafeterias, or salad bars, but should be proximate to the self-service food in order to comply with the new FDA rules. The display 1930 may thus be mounted on a stanchion proximate the self-service food and/or may be mounted on a wall proximate such food. In another aspect, the display 1930 may be mounted on, and even flush with, a counter top for a hot food buffet, a cold salad bar, etc.

In another aspect, the system 1900 may be placed in a covered establishment offering self-service food, and the system 1900 may comprise an electronic display 1930 proximate the self-service food, a user interface 1940 configured to enable a user to select a desired self-service food, to display on the electronic display, upon a user selecting the desired self-service food, a calorie count for a predetermined serving size of the desired self-service food, to enable a user to request Nutrition Facts information for the desired self-service food, and to display the Nutrition Facts information on the electronic display and/or to dispense a Nutrition Facts label containing the Nutrition Facts information. The user interface may be further configured to enable a user to select a desired quantity of the self-service food, and the system 1900 may be further configured to determine, based on the selected quantity of the self-service food, calorie content for the desired quantity of the self-service food, and to display the calorie content on the electronic display 1930, for example, in 10-calorie increments.

Another aspect of the disclosure comprises a method, as illustrated in FIG. 20. At operation 2010, one aspect of the method may comprise the step of receiving, at a covered establishment, information indicative of a selected desired self-service food. For example, a user may input on a user interface such as interface 1940, information indicating that a desired product has been selected. The information indicative of a selected desired self-service food may be received via one or more of a coded input, i.e., via interface 1940, a graphical user interface, and a self-service food product selection button or icon, such as a Coca-Cola icon on a Freestyle dispenser. In another aspect, for example, a remote user may, via a laptop computer or handheld device, place an order received at a covered establishment, such as Pizza Hut, for a pizza to be picked up or delivered.

At operation 2020, the method may comprise the step of displaying, responsive to receiving the information indicative of the selected desired self-service food, on a display proximate the selected desired self-service food, calorie information for the selected desired self-service food. Such display may, for example, be proximate the selected food product, for example at a cold salad bar. But optionally, for example, in the case of the information indicative of the selected desired self-service food comprising a food order received remotely at the covered establishment, i.e., for take-out pizza, the displaying step may comprise transmitting to an intended recipient for displaying on a remote display of the intended recipient, a graphical representation of the selected desired self-service food, (i.e., a photograph representative of the pizza being ordered) and the calorie information for the desired self-service food, i.e., the calories per slice, per pizza, etc.

At operation 2030, the method may comprise transmitting information indicating that Nutrition Facts information for the desired self-service food is available upon request. This step may make compliance with the requirements of the new FDA rules easier for covered establishments, as previously described, as it will be far easier for covered establishments to store and retrieve, for example, electronic Nutrition Facts information, rather than brochures or pamphlets containing such information, which may need to be stored, ordered, reprinted, accessed by wait staff, etc. The transmitting information operation 2030 indicating that Nutrition Facts information for the self-service food is available upon request may comprises one or more of displaying such information on the display 1930, providing an audible or visual query as to whether the Nutrition Facts information is desired, or enabling or illuminating a request Nutrition Facts button or icon 1980. As to providing an audible query, it is noted that the new FDA rules discuss the possibility of providing audible cues for visually impaired consumers, and it is within the scope of the teachings herein to provide such audible cues both for providing calorie information and Nutrition Facts information to the visually impaired.

The method illustrated in FIG. 20 may further comprise, as optional step 2040, receiving quantity information indicative of a quantity of the selected desired self-service food, and based on the quantity information, determining a calorie count for the quantity of the selected desired self-service food, and displaying the calorie count for the quantity of the selected desired self-service food.

The method illustrated in FIG. 20 may further comprise, at operation 2050, the step of, responsive to receiving information indicative of a request for Nutrition Facts information for the self-service food, displaying a virtual Nutrition Facts label for the desired self-service food, or dispensing a Nutrition Facts label for the desired self-service food. Such virtual Nutrition Facts label may be displayed on the display 1930, or dispensed in printed form via the printer device 1960.

The purpose of the present disclosure is not to criticize or judge sellers and manufacturers of consumer products, governing bodies and regulators that enact laws and regulations concerning such products, or consumers for the personal decisions they make regarding the purchase, use or consumption of such products. Rather, the present disclosure is intended to provide a framework for implementing systems, methods, and apparatus that may serve as a vehicle for a reasonable compromise among: (1) consumer product sellers and manufacturers who wish to comply with both the letter and spirit of all applicable case precedent, laws, and regulations concerning their products, who wish to provide full, frank, and fair disclosure to consumers regarding the attributes of such products, and who wish to provide consumers greater opportunities for making informed choices regarding which products they purchase, use, and consume; (2) governing and regulating bodies who wish to fulfill their respective charters to advocate on behalf of, protect, and serve their constituencies, to regulate the health and safety aspects of the products such constituencies purchase, use, and consume, and to direct the manner in which such products are advertised or sold; and (3) consumers who wish to be empowered to make fully informed choices regarding the products they purchase, use, and consume, who wish to have greater opportunities to customize such products and choices, and who wish to be able to make such choices freely.

I claim:

1. A blender comprising:
a motorized housing having mounted thereto a bayonet-mounted container, the bayonet-mounted container configured to contain and blend a food or beverage product, and to yield a user customized blend of a food or beverage product for immediate consumption, the user customized blend comprising a blend of a first food or beverage product and a second food or beverage product;
a weighing apparatus engaged with the blender, the weighing apparatus comprising one or more pressure sensors, the weighing apparatus configured to determine the weight of a food or beverage product after the food or beverage product is placed in the bayonet-mounted container;
an input device configured to receive Nutrition Facts information specific to the first food or beverage product and the second food or beverage product via a transceiver that accesses a remote database, via coded indicia applied to the first food or beverage product and the second food or beverage product or packaging therefor, the coded indicia comprising machine-readable codes;
a microprocessor communicatively coupled with the input device and the weighing apparatus, the microprocessor configured to sum and parse the Nutrition Facts information specific to the first food or beverage product and the second food or beverage product, based on the weight of the first food or beverage product and the second food or beverage product, and the Nutrition Facts information specific to the first food or beverage product and the second food or beverage product accessed via the remote database, into a standardized Nutrition Facts label format;
and
an output device comprising a display on, or a printer within, the housing and communicatively coupled with the input device, the microprocessor, and the weighing apparatus, the output device configured to produce an output comprising a Nutrition Facts label specific to the user customized blend of a food or beverage product for immediate consumption in the standardized Nutrition Facts label format.

2. The blender of claim 1, wherein the input device is one of a bar code scanner, an RFID reader, a magnetic strip reader, or a food product recognition module associated with the blender and a mobile application.

3. The blender of claim 2, wherein the output device comprises the printer, and the output comprises a printed Nutrition Facts label.

4. The blender of claim 2, wherein the output device comprises the display configured to display the output, wherein the output comprises a virtual Nutrition Facts label.

5. The blender of claim 4, wherein the output further comprises a virtual Nutrition Facts label transmitted to a mobile device of a user.

6. The blender of claim 2, wherein the weighing apparatus comprises one or more piezoelectric transducers positioned beneath the motorized housing.

7. The blender of claim 3, wherein the printed Nutrition Facts label comprises a Nutrition Facts section and a receipt section, the receipt section comprising sales receipt information specific to the food or beverage product for immediate consumption.

8. The blender of claim 3, wherein the printed Nutrition Facts label comprises an adhesive backing.

9. The blender of claim 1 wherein the input device is configured to receive Nutrition Facts information specific to the first food or beverage product and the second food or beverage product via coded indicia applied to the first food or beverage product and the second food or beverage product or packaging therefor, via a mobile application, comprising a reading device configured to read the coded indicia.

10. A blender comprising:
a housing;
a blending container;
a reader configured to receive, via machine readable coded indicia, without accessing a weighing device, first data comprising a weight or a volume of a food or beverage product intended to be placed in the blending container, the reader further configured to receive second data comprising Nutrition Facts information specific to the food or beverage product intended to be placed in the blending container, the reader further configured to receive the first and second data via the readable coded indicia applied either to:
(a) the food or beverage product, or (b) to packaging containing the food or beverage product;
a microprocessor configured to sum and parse the first and second data into a standardized Nutrition Facts label format;
and
a display on the housing, wherein the display is configured to display a virtual Nutrition Facts label in the standardized Nutrition Facts label format, wherein the virtual Nutrition Facts label comprises Nutrition Facts information specific to a food or beverage product for immediate consumption blended by the blender, based on the net weight or the volume of the food or beverage product placed in the blending container.

11. The blender of claim 10, further comprising a printer within the housing, the printer configured to print and dispense a printed Nutrition Facts label corresponding to the virtual Nutrition Facts label.

12. The blender of claim 11, wherein the printed Nutrition Facts label comprises a graduated label applicable to a container and ingredient attribute indicator markings.

13. The blender of claim 10, wherein the reader comprises a scanner configured to scan coded indicia of at least a first ingredient and a second ingredient, the coded indicia comprising Nutrition Facts and a weight or volume specific to the first ingredient and the second ingredient, and further wherein the blender is configured to combine the first ingredient with the second ingredient to yield a food or beverage product for immediate consumption.

14. The blender of claim 13, wherein at least one of the first ingredient and the second ingredient comprises a packaged food or beverage comprising a package to which the coded indicia is applied.

15. The blender of claim 10, wherein the reader comprises a bar code scanner, and the readable coded indicia comprises a bar code.

16. The blender of claim 10 wherein the reader comprises a bar code scanner and the readable coded indicia comprises a bar code.

17. A blender comprising:
   a. a motorized housing that engages a rotor blade configured to process food and/or beverages within a bayonet-mounted blending container;
   b. the housing comprising a scanner configured to scan a code associated with a food or beverage ingredient intended to be placed within the bayonet-mounted blending container, via readable coded indicia applied either to:
      i. the food or beverage ingredient, or
      ii. to packaging containing the food or beverage ingredient;
   c. a processor configured to:
      i. determine completion of a blending operation of a first food or beverage ingredient and a second food or beverage ingredient placed within the blending container, the blending operation resulting in a blended food or beverage product for immediate consumption;
   and
      ii. determine, without accessing a weighing device, Nutrition Facts and weight data specific to the first food or beverage ingredient and the second food or beverage ingredient based on readable coded indicia associated with the first food or beverage ingredient and the second food or beverage ingredient subsequent to the readable coded indicia having been scanned by the scanner;
   and
      iii. determine resulting Nutrition Facts specific to the blended food or beverage product for immediate consumption;
   and
      iv. parse the resulting Nutrition Facts specific to the blended food or beverage product for immediate consumption into a Nutrition Facts label specific to the blended food or beverage product for immediate consumption in a standardized Nutrition Facts label format;
   and
   e. at least one of:
      i. a display on the blender configured to display a virtual Nutrition Facts label specific to the blended food or beverage product for immediate consumption in the standardized Nutrition Facts label format;
   or
      ii. a printer within the blender configured to print and dispense the Nutrition Facts label specific to the blended food or beverage product for immediate consumption in the standardized Nutrition Facts label format.

18. The blender of claim 17, wherein the blender further comprises at least one of:
   a. a user interface configured to enable a user of the blender to enter a weight or a volume, and Nutrition Facts data for, the food or beverage ingredient intended to be placed within the blending container; and
   b. an input device configured to enable the blender to communicate wirelessly with a handheld device of a user to enable communication a weight or a volume, and Nutrition Facts data for, the food or beverage ingredient intended to be placed within the blending container.

* * * * *